US010132799B2

(12) United States Patent
Belmant et al.

(10) Patent No.: US 10,132,799 B2
(45) Date of Patent: Nov. 20, 2018

(54) SCREENING OF CONJUGATED ANTIBODIES

(71) Applicants: Innate Pharma, Marseilles (FR); Paul Scherrer Institut, Villigen PSI (CH)

(72) Inventors: Christian Belmant, Six-Fours-lès-Plages (FR); Delphine Bregeon, Marseilles (FR); Patrick Dennler, Wettingen (CH); Eliane Fischer, Eglisau (CH); François Romagne, Marseilles (FR); Roger Schibli, Baden (CH); Laurent Gauthier, Marseilles (FR)

(73) Assignees: INNATE PHARMA, Marseilles (FR); PAUL SCHERRER INSTITUT, Villigen PSI (CH)

( * ) Notice: Subject to any disclaimer, the term of this patent is extended or adjusted under 35 U.S.C. 154(b) by 282 days.

(21) Appl. No.: 14/414,432

(22) PCT Filed: Jul. 10, 2013

(86) PCT No.: PCT/EP2013/064605
§ 371 (c)(1),
(2) Date: Jan. 12, 2015

(87) PCT Pub. No.: WO2014/009426
PCT Pub. Date: Jan. 16, 2014

(65) Prior Publication Data
US 2015/0346195 A1 Dec. 3, 2015

Related U.S. Application Data

(60) Provisional application No. 61/671,128, filed on Jul. 13, 2012.

(51) Int. Cl.
| | |
|---|---|
| *A61K 47/48* | (2006.01) |
| *C07K 16/00* | (2006.01) |
| *C07K 16/30* | (2006.01) |
| *C07K 19/00* | (2006.01) |
| *A61K 31/5517* | (2006.01) |
| *C07C 217/08* | (2006.01) |
| *C07C 223/02* | (2006.01) |
| *C07C 229/26* | (2006.01) |
| *C07C 233/62* | (2006.01) |
| *C07C 247/04* | (2006.01) |
| *C07C 323/12* | (2006.01) |
| *C07C 323/60* | (2006.01) |
| *C07D 225/08* | (2006.01) |
| *C07D 257/08* | (2006.01) |
| *C07D 277/06* | (2006.01) |
| *C07F 9/50* | (2006.01) |
| *C12N 9/10* | (2006.01) |
| *C12P 21/00* | (2006.01) |
| *G01N 33/68* | (2006.01) |
| *G01N 33/532* | (2006.01) |
| *G01N 33/50* | (2006.01) |
| *A61K 47/68* | (2017.01) |

(52) U.S. Cl.
CPC .......... *G01N 33/532* (2013.01); *A61K 47/68* (2017.08); *C07K 16/00* (2013.01); *G01N 33/5014* (2013.01); *G01N 33/6854* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 4,741,900 A | 5/1988 | Alvarez et al. |
| 4,816,567 A | 3/1989 | Cabilly et al. |
| 5,156,956 A | 10/1992 | Motoki et al. |
| 5,225,539 A | 7/1993 | Winter |
| 5,229,275 A | 7/1993 | Goroff |
| 5,252,469 A | 10/1993 | Andou et al. |
| 5,530,101 A | 6/1996 | Queen et al. |
| 5,565,332 A | 10/1996 | Hoogenboom et al. |
| 5,567,610 A | 10/1996 | Borrebaeck et al. |
| 5,573,905 A | 11/1996 | Lerner et al. |
| 5,585,089 A | 12/1996 | Queen et al. |
| 5,693,761 A | 12/1997 | Queen et al. |
| 5,693,762 A | 12/1997 | Queen et al. |
| 5,712,120 A | 1/1998 | Rodriguez et al. |
| 5,714,350 A | 2/1998 | Co et al. |
| 5,731,183 A | 3/1998 | Kobayashi et al. |
| 5,736,356 A | 4/1998 | Sano et al. |

(Continued)

FOREIGN PATENT DOCUMENTS

| | | |
|---|---|---|
| DE | 19907588 A1 | 8/2000 |
| EP | 0555649 A2 | 8/1993 |
| EP | 1859811 A1 | 11/2007 |
| JP | 2003199569 A | 7/2003 |
| WO | WO 1992/02190 | 1/1992 |
| WO | WO 1992/11018 | 7/1992 |
| WO | WO 1992/22583 | 12/1992 |
| WO | WO 1993/10102 | 5/1993 |
| WO | WO 1996/06931 | 3/1996 |
| WO | WO 1996/22366 | 7/1996 |
| WO | WO 1998/25929 A1 | 6/1998 |
| WO | WO 1999/02514 A2 | 1/1999 |
| WO | WO 1999/07692 A2 | 2/1999 |

(Continued)

OTHER PUBLICATIONS

Jeger et al., Angewandte Chemie, 2010; 49:9995-97.*

(Continued)

*Primary Examiner* — Julie Wu
(74) *Attorney, Agent, or Firm* — Knobbe Martens Olson & Bear LLP

(57) ABSTRACT

Provided is a method for the functionalization of immunoglobulins through the use of transglutaminase, including methods for screening functionalized antibodies for characteristics of interest, antibody compositions comprising a plurality of functionalized antibodies, and functionalized antibodies with rodent constant regions.

22 Claims, 17 Drawing Sheets

(56) References Cited

U.S. PATENT DOCUMENTS

| | | |
|---|---|---|
| 5,766,886 A | 6/1998 | Studnicka et al. |
| 5,770,196 A | 6/1998 | Studnicka |
| 5,777,085 A | 7/1998 | Co et al. |
| 5,821,123 A | 10/1998 | Studnicka |
| 5,821,337 A | 10/1998 | Carter et al. |
| 5,869,619 A | 2/1999 | Studnicka |
| 5,877,293 A | 3/1999 | Adair et al. |
| 5,886,152 A | 3/1999 | Nakatani et al. |
| 5,895,205 A | 4/1999 | Werner et al. |
| 5,929,212 A | 7/1999 | Jolliffe et al. |
| 6,054,297 A | 4/2000 | Carter et al. |
| 6,162,963 A | 12/2000 | Kucherlapati et al. |
| 6,180,370 B1 | 1/2001 | Queen et al. |
| 6,204,388 B1 | 3/2001 | Danishefsky et al. |
| 6,380,394 B1 | 4/2002 | Nicolaou et al. |
| 6,387,927 B1 | 5/2002 | Altmann et al. |
| 6,407,213 B1 | 6/2002 | Carter et al. |
| 6,548,640 B1 | 4/2003 | Winter |
| 6,632,927 B2 | 10/2003 | Adair et al. |
| 6,639,055 B1 | 10/2003 | Carter et al. |
| 6,750,325 B1 | 6/2004 | Jolliffe et al. |
| 6,797,492 B2 | 9/2004 | Daugherty et al. |
| 6,881,557 B2 | 4/2005 | Foote |
| 7,087,409 B2 | 8/2006 | Barbas, III et al. |
| 7,090,843 B1 | 8/2006 | Francisco et al. |
| 7,117,096 B2 | 10/2006 | Luo et al. |
| 7,135,174 B2 | 11/2006 | Corvalan et al. |
| 7,338,933 B2 | 3/2008 | DeFrees et al. |
| 7,378,091 B2 | 5/2008 | Gudas et al. |
| 7,393,648 B2 | 7/2008 | Rother et al. |
| 7,498,298 B2 | 3/2009 | Doronina et al. |
| 7,657,380 B2 | 2/2010 | Lazar et al. |
| 7,659,241 B2 | 2/2010 | Senter et al. |
| 7,763,736 B2 | 7/2010 | Sharpless et al. |
| 7,807,619 B2 | 10/2010 | Bertozzi et al. |
| 7,981,843 B2 | 7/2011 | Flynn et al. |
| 8,133,515 B2 | 3/2012 | Boons et al. |
| 9,340,615 B2 | 5/2016 | Maeda et al. |
| 9,427,478 B2 | 8/2016 | Bregeon et al. |
| 9,676,871 B2 | 6/2017 | Strop et al. |
| 9,717,803 B2 | 8/2017 | Bregeon et al. |
| 9,764,038 B2 | 9/2017 | Dennler et al. |
| 2002/0034765 A1 | 3/2002 | Daugherty et al. |
| 2002/0052028 A1 | 5/2002 | Santi et al. |
| 2002/0058286 A1 | 5/2002 | Danishefsky et al. |
| 2002/0062030 A1 | 5/2002 | White et al. |
| 2002/0102208 A1 | 8/2002 | Chinn et al. |
| 2002/0161201 A1 | 10/2002 | Filpula et al. |
| 2003/0153043 A1 | 8/2003 | Carr et al. |
| 2004/0253645 A1 | 12/2004 | Daugherty et al. |
| 2005/0026263 A1 | 2/2005 | Meares et al. |
| 2005/0238646 A1 | 10/2005 | Ledbetter et al. |
| 2005/0238649 A1 | 10/2005 | Doronina et al. |
| 2005/0256030 A1 | 11/2005 | Feng |
| 2006/0073137 A1 | 4/2006 | Adair et al. |
| 2006/0116422 A1* | 6/2006 | De Groot .......... A61K 47/4813 514/483 |
| 2007/0122408 A1 | 5/2007 | Barbas, III et al. |
| 2008/0038260 A1 | 2/2008 | Ponath et al. |
| 2009/0028856 A1 | 1/2009 | Chen et al. |
| 2010/0004431 A1 | 1/2010 | Bernett et al. |
| 2011/0184147 A1 | 7/2011 | Kamiya et al. |
| 2011/0256157 A1 | 10/2011 | Howard et al. |
| 2011/0305631 A1 | 12/2011 | Govindan et al. |
| 2012/0322686 A1 | 12/2012 | Lyon et al. |
| 2013/0122020 A1 | 5/2013 | Liu et al. |
| 2013/0189287 A1 | 7/2013 | Bregeon et al. |
| 2013/0230543 A1 | 9/2013 | Pons et al. |
| 2014/0088089 A1 | 3/2014 | Chari |
| 2014/0356385 A1 | 12/2014 | Dennler et al. |
| 2015/0284713 A1* | 10/2015 | Fischer .............. C12N 15/1065 506/9 |
| 2015/0346195 A1 | 12/2015 | Belmant et al. |
| 2016/0022833 A1 | 1/2016 | Bregeon et al. |
| 2016/0114056 A1 | 4/2016 | Bregeon et al. |
| 2016/0331842 A1* | 11/2016 | Bregeon ........... A61K 31/5517 |
| 2017/0313787 A1 | 11/2017 | Strop et al. |
| 2018/0071402 A1 | 3/2018 | Bregeon et al. |

FOREIGN PATENT DOCUMENTS

| | | |
|---|---|---|
| WO | WO 1999/58534 A2 | 11/1999 |
| WO | WO 1999/67252 A2 | 12/1999 |
| WO | WO 1999/67253 A2 | 12/1999 |
| WO | WO 2000/000485 A1 | 1/2000 |
| WO | WO 2000/037473 A1 | 6/2000 |
| WO | WO 2000/0044788 A1 | 8/2000 |
| WO | WO 2000/049019 A2 | 8/2000 |
| WO | WO 2000/049020 A2 | 8/2000 |
| WO | WO 2000/049021 A2 | 8/2000 |
| WO | WO 2000/057874 A1 | 10/2000 |
| WO | WO 2000/066589 A1 | 11/2000 |
| WO | WO 2000/071521 A1 | 11/2000 |
| WO | WO 2001/027308 A2 | 4/2001 |
| WO | WO 2001/064650 A2 | 9/2001 |
| WO | WO 2001/070716 A1 | 9/2001 |
| WO | WO 2001/073103 A2 | 10/2001 |
| WO | WO 2001/081342 A2 | 11/2001 |
| WO | WO 2001/092255 A2 | 12/2001 |
| WO | WO 2002/008440 A2 | 1/2002 |
| WO | WO 2002/014323 A2 | 2/2002 |
| WO | WO 2002/030356 A2 | 4/2002 |
| WO | WO 2002/032844 A2 | 4/2002 |
| WO | WO 2002/080846 A2 | 10/2002 |
| WO | WO 2002/083180 A1 | 10/2002 |
| WO | WO 2003/074053 A1 | 9/2003 |
| WO | WO 2004/014919 A1 | 2/2004 |
| WO | WO 2004/043493 A1 | 5/2004 |
| WO | WO 2004/043880 A2 | 5/2004 |
| WO | WO 2005/040219 A1 | 5/2005 |
| WO | WO 2005/070468 A2 | 8/2005 |
| WO | WO 2005/085251 A1 | 9/2005 |
| WO | WO 2007/008603 A1 | 1/2007 |
| WO | WO 2007/008848 A2 | 1/2007 |
| WO | WO 2007/020290 A1 | 2/2007 |
| WO | WO 2008/017122 | 2/2008 |
| WO | WO 2008/102008 A1 | 8/2008 |
| WO | WO 2009/067663 A1 | 5/2009 |
| WO | WO 2009/105969 A1 | 9/2009 |
| WO | WO 2010/115630 A1 | 10/2010 |
| WO | WO 2010/136598 A1 | 12/2010 |
| WO | WO 2011/023883 A1 | 3/2011 |
| WO | WO 2011/136645 A1 | 3/2011 |
| WO | WO 2011/085523 A1 | 7/2011 |
| WO | WO 2011/120053 A1 | 9/2011 |
| WO | WO 2011/130616 A1 | 10/2011 |
| WO | WO 2012/041504 A1 | 4/2012 |
| WO | WO 2012/059882 A2 | 5/2012 |
| WO | WO 2012/112687 A1 | 8/2012 |
| WO | WO 2013/092983 A2 | 6/2013 |
| WO | WO 2013/092998 A1 | 6/2013 |
| WO | WO 2013/177481 A1 | 11/2013 |
| WO | WO 2014/009426 A1 | 1/2014 |
| WO | WO 2014/072482 A1 | 5/2014 |
| WO | WO 2014/140300 A1 | 9/2014 |
| WO | WO 2014/202773 A1 | 12/2014 |

OTHER PUBLICATIONS

Starling et al. (Bioconjugate Chemistry, 1992, 3:315-322, abstract).*

Chari, Ravi V.J., "Targeted Cancer Therapy: Conferring Specificity to Cytotoxic Drugs", Acc of Chem Res, (Jan. 2008) 41(1):98-107.

Lhospice et al.,"Cite-specific conjugation of monomethyl auristatin E to Anti-CD30 antibodies improves their pharmacokinetics and therapeutic index in rodent models", Mol Pharmaceutics (2015) 12:1863-1871.

International Search Report and Written Opinion of the International Searching Authority dated Aug. 20, 2014 for International Application No. PCT/EP2014/063061 filed Jun. 20, 2014.

U.S. Response to Office Action filed Dec. 11, 2015 in U.S. Appl. No. 13/725,382, filed Dec. 21, 2012.

U.S. Office Action dated Feb. 25, 2016 in U.S. Appl. No. 13/725,382, filed Dec. 21, 2012.

(56) References Cited

OTHER PUBLICATIONS

U.S. Office Action dated Jan. 29, 2016 in U.S. Appl. No. 14/367,840, filed Jun. 20, 2014.
U.S. Office Action dated Oct. 8, 2015 in U.S. Appl. No. 14/582,040, filed Dec. 23, 2014.
Response to Office Action filed Dec. 8, 2015 in U.S. Appl. No. 14/582,040, filed Dec. 23, 2014.
U.S. Office Action dated Feb. 11, 2016 in U.S. Appl. No. 14/582,040, filed Dec. 23, 2014.
Response to Office Action filed Feb. 29, 2016 in U.S. Appl. No. 14/582,040, filed Dec. 23, 2014.
U.S. Office Action dated Sep. 16, 2015 in U.S. Appl. No. 13/883,535, filed May 3, 2013.
U.S. Response dated Nov. 16, 2015 in U.S. Appl. No. 13/883,535, filed May 3, 2013.
U.S. Office Action dated Dec. 30, 2015 in U.S. Appl. No. 13/883,535, filed May 3, 2013.
Baeuerle et al., "Bispecific T-cell engaging antibodies for cancer therapy", Cancer Res. (2009) 69(12):4941-4944.
Dosio et al., "Immunotoxins and Anticancer Drug Conjugate Assemblies: The Role of the Linkage between Components", Toxins (2011) 3:848-883.
Jackman et al., "Development of a two-part strategy to identify a therapeutic human bispecific antibody that inhibits IgE receptor signaling", J Biol Chem. (2010) 285(27):20850-20859.
Kamiya et al., "S-Peptide as a Potent Peptidyl Linker for Protein Cross-Linking by Microbial Transglutaminase from *Streptomyces mobaraensis*", Bioconj Chem. (2003) 14:351-357.
Pearson, William R., "Flexible sequence similarity searching with the FASTA3 program package", Methods Mol Biol. (2000) 132:185-219.
Plagmann et al., "Transglutaminase-catalyzed covalent multimerization of camelidae anti-human TNF single domain antibodies improves neutralizing activity", J Biotech. (2009) 142:170-178.
Nilsson et al., A synthetic IgG-binding domain based on stapylococcal protein A. Protein Eng. (1987) 1(2):107-113.
Strop et al., "Location Matters: Site of Conjugation Modulates Stability and Pharmacokinetics of Antibody Drug Conjugates", Chem Biol. (2013) 20(2):161-167.
Sung et al., "Functional glass surface displaying a glutamyl donor substrate for transglutaminase-mediated protein immobilization", Biotech J. (2010) (5):456-462.
Uhlén et al., Complete Sequence of the Staphylococcal Gene Encoding Protein A—A Gene Evolved Through Multiple Duplications. J Biol Chem. (1984) 259(3):1695-1702.
Yu et al., "Interaction between Bevacizumab and Murine VEGF-A: A Reassessment", Invest Ophtalmol Vis Sci. (Feb. 2008);49(2):522-527.
International Search Report dated Apr. 15, 2014 for International Application No. PCT/EP2013/073428 filed Nov. 8, 2013.
U.S. Office Action dated Feb. 27, 2015 in U.S. Appl. No. 13/725,382, filed Dec. 21, 2012.
U.S. Office Action dated Apr. 23, 2015 in U.S. Appl. No. 14/582,040, filed Dec. 23, 2014.
U.S. Preliminary Amendment dated May 3, 2013 in U.S. Appl. No. 13/883,535, filed May 3, 2013.
U.S. Office Action dated Dec. 19, 2014 in U.S. Appl. No. 13/883,535, filed May 3, 2013.
U.S. Second Preliminary Amendment dated Feb. 17, 2015 in U.S. Appl. No. 13/883,535, filed May 3, 2013.
Altschul et al., "Gapped BLAST and PSI-BLAST: A new generation of protein database search programs", Nucl Acids Res. (1997) 25(17): 3389-3402.
Altschul et al., "Basic Local Alignment Search Tool", J Mol Biol. (1990) 215:403-410.
Amersham Biosciences, Antibody Purification Handbook, (2002) Publication No. 18-1037-46, Edition AC, 112 pages.
Amsberry et al., "The Lactonization of 2'-Hydroxyhydrocinnamic Acid Amides: A Potential Prodrug for Amines", J. Org Chem (1990) 55:5867-5877.
Ando et al., "Purification and Characteristics of a Novel Transglutaminase Derived from Microorganisms", Agric Biol Chem. (1989) 53(10):2613-2617.
Ausubel et al. (Eds.) Current Protocols in Molecular Biology (1993) John Wiley & Sons, Inc., Table of Contents, 15 pages.
Bernard et al., "Cysteine analogs of recombinant barley ribosome inactivating protein form antibody conjugates with enhanced stability and potency in vitro", Bioconjugate Chem., (1994) 5(2):126-132.
Brabez et al., "Design, synthesis and biological studies of efficient multivalent melanotropin ligands: tools towards melanoma diagnosis and treatment", J Med Chem. (2011) 54(20):7375-7384.
Carillo et al., "The Multiple Sequence Alignment Problem in Biology", Siam J. Appl Math. (1988) 48(5):1073-1082.
Carter et al., "Improved oligonucleotide site-directed mutagenesis using M13 vectors", Nucl Acids Res. (1985) 13(12):4431-4443.
Carter et al., "Humanization of an anti-p185HER2 antibody for human cancer therapy", Proc Natl Acad Sci. USA (1992) 89:4285-4289.
Chapman, Andrew P., "PEGylated antibodies and antibody fragments for improved therapy: a review", Advan Drug Del Rev. (2002) 54:531-545.
Chothia et al., "Canonical Structures for the Hypervariable Regions of Immunoglobulins", J Mol Biol. (1987) 196:901-917.
Connolly et al., "In Vivo Inhibition of Fas Ligand-Mediated Killing by TR6, a Fas Ligand Decoy Receptor", J Pharmacol Exp Ther. (2001) 298(1):25-33.
De Pascalis et al., "Grafting of "Abbreviated" Complementarity-Determining Regions Containing Specificity-Determining Residues Essential for Ligand Contact to Engineer a Less Immunogenic Humanized Monoclonal Antibody", J Immunol. (2002) 169(6):3076-3084.
Dennler et al., Enzymatic antibody modification by bacterial transglutaminase. Bioconjugate Chemistry, (2013) 1045:205-215.
Dennler et al., Transglutaminase-based chemo-enzymatic conjugation approach yields homogeneous antibody-drug conjugates. Bioconjugate Chemistry, (2014) 25(3):569-578.
Devereux et al., "A comprehensive set of sequence analysis programs for the VAX", Nucl Acids Res. (1984) 12(1):387-395.
Doronina et al., "Development of potent monoclonal antibody Auristatin conjugates for cancer therapy", Nat Biotech. (2003) 21(7):778-784 & Erratum Nat Biotech. (2003) 21(8):941.
Doronina et al., "Enhanced activity of monomethylauristatin F through Monoclonal Antibody Delivery", Bioconjugate Chem. (2006) 17(1):114-124.
Edelman et al., "The Covalent Structure of an Entire γG Immunoglobulin Molecule", Proc Natl Acad. USA, (1969) 63:78-85.
Folk et al., "Polyamines as Physiological Substrates for Transglutaminases", J. Biol. Chem. (1980) 255(8):3695-3700.
GENBANK Reference Sequence NM_024003.2; "*Homo sapiens* L1 cell adhesion molecule (L1CAM), transcript variant 2, mRNA", May 4, 2013; 8 pages.
GENBANK Reference Sequence NM_024003.3; "*Homo sapiens* L1 cell adhesion molecule (L1CAM), transcript variant 2, mRNA", May 26, 2013; 10 pages.
GENBANK Reference Sequence NM_0764493.1; "Neural cell adhesion molecule L1 isoform 2 precursor [*Homo sapiens*]", May 26, 2014; 6 pages.
Gorman et al., "Transglutaminase Amine Substrates for Photochemical Labeling and Cleavable Cross-linking of Proteins", J Biol Chem. (1980) 255(3):1175-1180.
Green et al., "Antigen-specific human monoclonal antibodies from mice engineered with human Ig heavy and light chain YACs", Nature Gen. (1994) 7:13-21.
Gribskov et al., (Eds.) Sequence Analysis Primer; Stockton Press (1991); Table of Contents, 7 pages.
Griffin et al., (Eds.) Methods in Molecular Biology-24: Computer Analysis of Sequence Data; Part I & II; Humana Press, New Jersey (1994) Tables of Contents, 8 pages.
Griffiths et al., "Human anti-self antibodies with high specificity from phage display libraries", EMBO J. (1993) 12(2):725-734.

(56) References Cited

OTHER PUBLICATIONS

Griffiths et al., "Isolation of high affinity human antibodies directly from large synthetic repertoires", EMBO J. (1994) 13(14):3245-3260.
Grünberg et al. 2013. DOTA-functionalized polylysine: A high number of DOTA chelates positively influences the biodistribution of enzymatic conjugated anti-tumor antibody chCE7agl. Plos One, 8(4):e60350.
Hamblett et al., "Effects of Drug Loading on the Antitumor Activity of a Monoclonal Antibody Drug Conjugate", Clin Cancer Res. (2004) 10:7063-7070.
Harlow et al., (Eds.), Antibodies—A Laboratory Manual; Table of Contents, Cold Spring Harbor Laboratory Press, Cold Spring Harbor, NY (1988) TOC; 9 pages.
Hay et al., "A 2-nitroimidazole carbamate prodrug of 5-amino-1-(Chloromethyl)-3-[(5,6,7-Trimethoxyindol-2-YL)Carbonyl]-1,2-dihydro-3H-Benz[e]indole (amino-SECO-CBI-TMI) for use with ADEPT and GDEPT", Bioorg Med Chem Lttrs. (1999) 9:2237-2242.
Higuchi, Russell "Recombinant PCR" Chapter 22 in Part II of PCR Protocols, A Guide to Methods and Applications [Innis et al. (Eds.)], Academic Press, (1990) pp. 177-183.
Ho et al. Site-directed Mutagenesis by Overlap Extension Using the Polymerase Chain Reaction. Gene (1989) 77(1):51-59.
Hollinger et al., "Engineered antibody fragments and the rise of single domains", Nature Biotech. (2005) 23(9):1126-1136.
Ill et al., "Design and construction of a hybrid immunoglobulin domain with properties of both heavy and light chain variable regions", Prot Engineer. (1997) 10(8):949-957.
Ito et al A General Method for Introducing a Series of Mutations into Cloned DNA Using the Polymerase Chain Reaction. Gene (1991) 102(1):67-70.
Jakobovits et al., "Germ-line transmission and expression of a human-derived yeast artificial chromosome", Nature (1993) 362:255-258.
Jones et al., "Replacing the complementarity-determining regions in a human antibody with those from a mouse", Nature (1986) 321:522-525.
Josten et al., "Use of microbial transglutaminase for the enzymatic biotinylation of antibodies", J Immunol Meth. (2000) 240:47-54.
Junutula et al., "Site-specific conjugation of a cytotoxic drug to an antibody improves the therapeutic index", Nature Biotech (2008) 26(8):925-932.
Kabat et al., (Eds.) Sequences of Proteins of Immunological Interest, 5th Edition; (1991) Table of Contents; 11 pages.
Kämpfer et al., "A numerical classification of the genera Streptomyces and Streptoverticillium using miniaturized physiological tests", J Gen Microbiol. (1991) 137:1831-1891.
Kajiwara et al., "Expression of L1 Cell Adhesion Molecule and Morphologic Features at the Invasive Front of Colorectal Cancer", Anat Pathol. (2011) 136(1):138-144.
Kamiya et al., "Site-specific cross-linking of functional proteins by transglutamination", Enzy Micro Tech. (2003) 33:492-496.
Kingsbury et al., "A Novel Peptide Delivery System Involving Peptidase Activated Prodrugs as Antimicrobial Agents. Synthesis and Biological Activity of Peptidyl Derivatives of 5-Fluorouracil", J Med Chem. (1984) 27:1447-1451.
Knappik et al., "Fully Synthetic Human Combinatorial Antibody Libraries (HuCAL) Based on Modular Consensus Frameworks and CDRs Randomized with Trinucleotides", J Mol Biol. (2000) 296:57-86.
Knogler et al., "Copper-67 Radioimmunotherapy and Growth Inhibition by Anti-L1-Cell Adhesion Molecule Monoclonal Antibodies in a Therapy Model of Ovarian Cancer Metastasis", Clin Cancer Res (2007) 13(2):603-611.
Kuil et al., "ITAM-derived phosphopeptide-containing dendrimers as multivalent ligands for Syk tandem SH2 domain", Org Biomol Chem. (2009) 7:4088-4094.
Kunkel, Thomas A., "Rapid and efficient site-specific mutagenesis without phenotypic selection", Proc Natl Acad Sci USA (1985) 82:488-492.
Lesk, Arthur M. (Ed.) Computational Molecular Biology, Oxford University Press (1988); Table of Contents; 4 pages.
Lin et al., "Transglutaminase-catalyzed site-specific conjugation of small-molecule probes to proteins in vitro and on the surface of living cells", J Am Chem Soc. (2006) 128(14):4542-4543 (7pages).
Liu et al., "Identification of Active Site Residues in the "GyrA" Half of Yeast DNA Topoisomerase II", J Biol Chem. (1998) 273(32):20252-20260.
Lonberg et al., "Antigen-specific human antibodies from mice comprising four distinct genetic modifications", Nature (1994) 368:856-859.
Lonberg, Nils, "Human antibodies from transgenic animals", Nature Biotech. (2005) 23(9):1117-1125.
Lorand et al., "Specificity of Guinea Pig Liver Transglutaminase for Amine Substrates", Biochem. (1979) 18(9):1756-1765.
Lorand et al., "Transglutaminases: Cross-linking enzymes with pleiotropic functions", Nature (2003) 4:140-156.
Lyon et al., "Conjugation of Anticancer Drugs through Endogenous Monoclonal Antibody Cysteine Residues", Meth Enzymol. (2012) 502:123-138.
Maeda et al., "Susceptibility of human T-cell leukemia virus type I-infected cells to humanized anti-CD30 monoclonal antibodies in vitro and in vivo", Cancer Sci. (2010) 101(1):224-230.
McCafferty et al., "Phage antibodies: Filamentous phage displaying antibody variable domains", Nature (1990) 348:552-554.
Morrison et al., "Chimeric human antibody molecules: Mouse antigen-binding domains with human constant region domains", Proc Natl Acad Sci. USA (1984) 81:6851-6855.
Murthy et al., "Residue Gln-30 of Human Erythrocyte Anion Transporter is a Prime Site for Reaction with Intrinsic Transglutaminase" J Biolog Chem. (1994) 269(36):22907-22911.
Murthy et al., "Selectivity in the Post-Translational, Transglutaminase-dependent Acylation of Lysine Residues", Biochem. (2009) 48:2654-2660.
Pearson, William R., "Rapid and Sensitive Sequence Comparison with FASTP and FASTA", Meth Enzymol. (1990) 183(5):63-98.
Presta, Leonard G., "Antibody engineering", Curr Opin Struct Biol. (1992) 2:593-596.
Presta et al., "Humanization of an Antibody Directed Against IgE", J Immunol. (1993) 151(5):2623-2632.
Riechmann et al., "Reshaping human antibodies for therapy", Nature (1988) 332:323-327.
Rodrigues et al., "Synthesis and β-lactamase-mediated activation of a cephalosporin-taxol prodrug", Chem Biol. (1995) 2:223-227.
Roguska et al., "Humanization of murine monoclonal antibodies through variable domain resurfacing", Proc Natl Acad Sci. (1994) 91:969-973.
Sambrook et al., (Eds.) Molecular Cloning—A Laboratory Manual, [2nd Edition]; Cold Spring Harbor Laboratory Press, NY; (1989) Table of Contents, 30 pages.
Sambrook et al., (Eds.) Molecular Cloning—A Laboratory Manual, [3rd Edition]; vol. 1; Cold Spring Harbor Laboratory Press, NY; (2001); Table of Contents, 18 pages.
Sazinsky et al., "Aglycosylated immunoglobulin G1 variants productively engage activating Fc receptors", PNAS (2008) 105(51):20167-20172.
Sims et al., "A Humanized CD18 Antibody can block Function without Cell Destruction", J Immunol. (1993) 151:2296-2308.
Smith, Douglas W. (Ed.), Biocomputing—Informatics and Genome Projects, Academic Press, Inc. (1993) Table of Contents, 7 pages.
Suzuki et al., Glycopinion Mini-Review: N-Glycosylation/Deglycosylation as a Mechanism for the Post-Translational Modification/Remodification of Proteins. Glycoconjug J. (1995) 12:183-193.
Takazawa et al., Enzymatic Labeling of a Single Chain Variable Fragment of an Antibody With Alkaline Phosphates by Microbial Transglutaminase. Biotech Engin. (2004) 86(4):399-404.
Tan et al., "Superhumanized" Antibodies: Reduction of Immunogenic Potential by Complementarity-Determining Region Grafting with Human Germline Sequences: Application to an Anti-CD28. J Immunol. (2002) 169:1119-1125.

(56) References Cited

OTHER PUBLICATIONS

Tomlinson et al., The Repertoire of Human Germline VH Sequences Reveals about Fifty Groups of VH Segments with Different Hypervariable Loops. J Mol Biol. (1992) 227:776-798.
Vallette et al., Construction of Mutant and Chimeric Genes Using the Polymerase Chain Reaction. Nuc Acids Res. (1989) 17(2):723-733.
Verhoeyen et al., Reshaping Human Antibodies: Grafting an Antilysozyme Activity. Science (1988) 239:1534-1536.
Von Heinje, Gunnar [Ed.] "Sequence Analysis in Molecular Biology—Treasure Trove or Trivial Pursuit", 1987, Academic Press [TOC Only].
Wakankar et al., Analytical Methods for Physicochemical Characterization of Antibody Drug Conjugates. Landes Biosci. (2011) 3(2):161-172.
Wängler et al., "Antibody-Dendrimer Conjugates: The Number, Not the Size of the Dendrimers, Determines the Immunoreactivity" Bioconjugate Chem. (2008) (19)4:813-820.
Ward et al., Binding Activities of a Repertoire of Single Immunoglobulin Variable Domains Secreted From *Escherichia coli*. Nature (1989) 341:544-546.
Wells et al., Cassette Mutagenesis: An Efficient Method for Generation of Multiple Mutations at Defined Sites. Gene (1985) 34(2-3):315-323.
Xu et al., "Characterization of intact antibodydrug conjugates from plasma/serum in vivo by affinity capture capillary liquid chromatography mass spectrometry", Anal Biochem. (2011) 412(1): 56-66.
Yurkovetskiy et al., Synthesis of a Macromolecular Camptothecin Conjugate with Dual Phase Drug Release. Mol Pharm. (2004) 1(5):375-382.
Zoller et al., "Oligonucleotide-directed mutagenesis using M13-derived vectors: an efficient and general procedure for the production of point mutations in any fragment of DNA", Nucl Acids Res. (1982) 10(20):6487-6500.
Zoller et al., "Oligonucleotide-directed mutagenesis of DNA fragments cloned into M13 vectors", Methods Enzymol. (1983) 100:468-500.
International Search Report dated Apr. 23, 2013 for International Application No. PCT/EP2012/076631 filed Dec. 21, 2012.
International Search Report dated Feb. 5, 2014 for International Application No. PCT/EP2012/076606 filed Dec. 21, 2012.
International Search Report and Written Opinion dated Sep. 24, 2014 for International Application No. PCT/EP2014/063064 filed Jun. 20, 2014, 16 pages.
U.S. Appl. No. 61/410,840, filed Nov. 5, 2010.
U.S. Appl. No. 61/553,917, filed Oct. 31, 2011.
U.S. Appl. No. 61/579,908, filed Dec. 23, 2011.
U.S. Appl. No. 61/661,569, filed Jun. 19, 2012.
U.S. Appl. No. 61/671,122, filed Jul. 13, 2012.
U.S. Appl. No. 61/671,128, filed Jul. 13, 2012.
U.S. Appl. No. 61/837,932, filed Jun. 21, 2013.
Jeger, Simone. 2009. Site-specific conjugation of tumour-targeting antibodies using transglutaminase. *Dissertation submitted to ETH Zurich*, 140 pages.
Jeger et al. 2010. Site-specific and stoichiometric modification of antibodies by bacterial transglutaminase. *Angewandte Chemie International Edition, Wiley VCH*, 49(51):9995-9997.
Jeger et al. 2010. Site-specific and stoichiometric modification of antibodies by bacterial transglutaminase—Supporting Information. *Angewandte Chemie International Edition, Wiley VCH*, 46 pages.
Mindt et al. 2008. Modification of different IgG1 antibodies via glutamine and lysine using bacterial and human tissue transglutaminase. *Bioconjugate Chemistry*, 19(1):271-278.
International Search Report dated Jan. 31, 2014 for International Application No. PCT/EP2013/064605 filed Jul. 10, 2014, 6 pages.
Golay et al., "Mechanism of action of therapeutic monoclonal antibodies: Promises and pitfalls of in vitro and in vivo assays", Arch Biochem Biophys (2012) 526:146-153.
Gregson et al., "Linker Length Modules DNA Cross-Linking Reactivity and Cytotoxic Potency of C8/C8' Ether-linked C2-exo-Unsaturated Pyrrolo[2,1-c][1,4]benzodiazepine (PBD) Dimers", J Med Chem (2004) 47:1161-1174.
Hay et al., "Clinical development success rates for investigational drugs", Nat Biotech. (Jan. 2014) 32(1):40-51.
Hu et al., "Rational design of transglutaminase substrate peptides for rapid enzymatic formation of hydrogels", J Am Chem Soc. (Nov. 2003) 125(47):14298-14299.
Jeffrey et al., "Development and Properties of beta-Glucuronide Linkers for Monoclonal Antibody-Drug Conjugates", Bioconj Chem. (2006) 17:831-840.
Jubala et al., "CD20 Expression in Normal Canine B Cells and in Canine non-Hodgkin Lymphoma", Vet Pathol. (2005) 42:368-476.
Kamal et al., "Synthesis of 1,2,3-triazole-linked pyrrolobenzodiazepine conjugates employing 'click' chemistry: DNA-binding affinity and anticancer activity", Bioorg Med Chem Lett. (Feb. 2008) 18(4):1468-1473.
Moses et al., "The growing applications of click chemistry", Chem Soc Rev. (Aug. 2007) 36(8):1249-1262.
Stancovski et al., "Mechanistic aspects of the opposing effects of monoclonal antibodies to the ERBB2 receptor on tumor growth", Proc Nati Acad Sci USA. (Oct. 1991) 88(19):8691-8695.
International Search Report dated Jun. 25, 2014 for International Application No. PCT/EP2014/055140 filed Mar. 14, 2014.
U.S. Response to Office Action filed May 28, 2015 in U.S. Appl. No. 13/725,382, filed Dec. 21, 2012.
U.S. Office Action dated Aug. 13, 2015 in U.S. Appl. No. 13/725,382, filed Dec. 21, 2012.
U.S. Response to Office Action filed May 20, 2015 in U.S. Appl. No. 14/582,040, filed Dec. 23, 2014.
U.S. Pre-Interview Communication dated Jul. 2, 2015 in U.S. Appl. No. 14/582,040, filed Dec. 23, 2014.
U.S. Response to Pre-Interview Communication filed Jul. 31, 2015 in U.S. Appl. No. 14/582,040, filed Dec. 23, 2014.
Agard et al., "A Strain-Promoted [3+2] Azide-Alkyne Cycloaddition for Covalent Modification of Biomolecules in Living Systems", J Am Chem Soc Comm. (2004) 126:15046-15047.
U.S. Response to Office Action filed May 23, 2016 in U.S. Appl. No. 13/725,382, filed Dec. 21, 2012.
U.S. Office Action dated Aug. 8, 2016 in U.S. Appl. No. 13/725,382, filed Dec. 21, 2012.
U.S. Response to Office Action filed Nov. 9, 2016 in U.S. Appl. No. 13/725,382, filed Dec. 21, 2012.
U.S. Notice of Allowance dated Mar. 28, 2017 in U.S. Appl. No. 13/725,382, filed Dec. 21, 2012.
U.S. Notice of Allowability/Examiner's Amendment dated Apr. 28, 2017 in U.S. Appl. No. 13/725,382, filed Dec. 21, 2012.
U.S.Response to Office Action filed Mar. 25, 2016 in U.S. Appl. No. 14/367,840, filed Jun. 20, 2014.
U.S. Office Action dated Jun. 17, 2016 in U.S. Appl. No. 14/367,840, filed Jun. 20, 2014.
U.S. Response to Office Action filed Nov. 14, 2016 in U.S. Appl. No. 14/367,840, filed Jun. 20, 2014.
U.S. Office Action dated Jan. 31, 2017 in U.S. Appl. No. 14/367,840, filed Jun. 20, 2014.
U.S. Response to Office Action filed Apr. 28, 2017 in Application No. 14/367,840, filed Jun. 20, 2014.
U.S. Notice of Allowance dated May 16, 2017 in U.S. Appl. No. 14/367,840, filed Jun. 20, 2014.
U.S. Notice of Allowance dated Jun. 6, 2016 in U.S. Appl. No. 14/582,040, filed Dec. 23, 2014.
Preliminary Amendment dated Jan. 9, 2017 in U.S. Appl. No. 15/214,331, filed Jul. 19, 2016.
U.S. Office Action dated Feb. 28, 2017 in U.S. Appl. No. 14/441,157, filed May 6, 2015.
U.S. Response to Office Action filed Apr. 26, 2017 in U.S. Appl. No. 14/441,157, filed May 6, 2015.
U.S. Office Action dated Mar. 28, 2017 in U.S. Appl. No. 14/775,647, filed Sep. 11, 2015.
U.S.Response to Office Action filed Jun. 28, 2017 in U.S. Appl. No. 14/775,647, filed Sep. 11, 2015.
U.S. Office Action dated Mar. 31, 2017 in U.S. Appl. No. 14/898,693, filed Dec. 15, 2015.

(56) References Cited

OTHER PUBLICATIONS

U.S. Response to Office Action filed Jun. 29, 2017 in U.S. Appl. No. 14/898,693, filed Dec. 15, 2015.
U.S. Response dated May 2, 2016 in U.S. Appl. No. 13/883,535, filed May 3, 2013.
U.S. Office Action dated Jul. 5, 2016 in U.S. Appl. No. 13/883,535, filed May 3, 2013.
U.S. Response dated Sep. 1, 2016 in U.S. Appl. No. 13/883,535, filed May 3, 2013.
U.S. Notice of Allowance dated Feb. 8, 2017 in U.S. Appl. No. 13/883,535, filed May 3, 2013.
U.S. Rule 312 Amendment dated Apr. 3, 2017 in U.S. Appl. No. 13/883,535, filed May 3, 2013.
Alley et al., "Antibody-drug conjugates: targeted drug delivery for cancer", Curr Opin Chem Biol. (2010) 14:529-537.
International ImMunoGeneTics Information Systems, "MCT Scientific Chart" (downloaded from the web Aug. 20, 2017) URL: http://www.imgt.org/IMGTScientificChart/Numbering/Hu_IGHGnber.html; 4 pages.
U.S. Office Action dated Oct. 19, 2017 in U.S. Appl. No. 14/898,693, filed Dec. 15, 2015.
U.S. Preliminary Amendment dated Jul. 19, 2017 in U.S. Appl. No. 15/654,585, filed Jul. 19, 2017.
U.S. Office Action dated Sep. 19, 2017 in U.S. Appl. No. 14/441,157, filed May 6, 2015.
U.S. Office Action dated Aug. 22, 2017 in U.S. Appl. No. 14/775,647, filed Sep. 11, 2015.
U.S. Response to Office Action filed Nov. 21, 2017 in U.S. Appl. No. 14/775,647, filed Sep. 11, 2015.
U.S. Divisional Application/Preliminary Amendment dated May 11, 2017 in U.S. Appl. No. 15/593,259, filed May 11, 2017.
U.S. Response to Office Action dated Jan. 19, 2018 in U.S. Appl. No. 14/898,693, filed Dec. 15, 20115.

\* cited by examiner

SCREENING OF CONJUGATED ANTIBODIES

CROSS-REFERENCE TO RELATED APPLICATIONS

This application is the U.S. National Phase of Application No. PCT/EP2013/064605 entitled "SCREENING OF CONJUGATED ANTIBODIES" filed Jul. 10, 2013, which designated the United States and this application claims the benefit of U.S. Provisional Application No. 61/671,128 filed Jul. 13, 2012, which is incorporated herein by reference in its entirety, including any drawings.

FIELD OF THE INVENTION

The present invention relates to a method for the functionalization of immunoglobulins.

BACKGROUND

Immunoglobulins conjugated to a drug of interest, generally known as antibody drug conjugates (ADCs), are a promising area of therapeutic research. Recent developments in ADC technology have focused on linker technology that provides for intracellular cleavage or more recently, non-cleavable linkers that provide greater in vivo stability and reduced toxicity. The feasibility of an ADC approach, however, is not only depend on linker technologies and drugs, but also on the cellular target, and moreover upon the particular antibody to which a drug is linked. Antibodies may bind antigens in different ways, e.g. giving rise to different profiles of internalization, or antibodies may bind to epitopes present on non-targeted tissues. As a consequence, it is generally believed that each antibody must be examined separately. Evaluating large numbers of antibodies for their suitability for ADC approaches is difficult because antibodies must be conjugated to drugs in a stoichiometric manner such that the effect of the antibody (e.g. epitope specificity, affinity, etc.) can be separated from the effect of the drug. Screening of antibodies suitable for further development as ADCs therefore remains an expensive and time-consuming process.

In view of the foregoing, there remains a need in the art for methods to assess which combination of antibody, linker and drug structure are best suited for a particular application.

SUMMARY OF THE INVENTION

The present invention arises, inter alia, from the development of an approach to make use of transglutaminase (TGase)-mediated conjugation to overcome difficulties in conjugation of drugs to immunoglobulins (referred to interchangeably with "antibodies"), and from the provision of TGase-mediated conjugation approaches that permit the uniform stoichiometric modification of different antibody species (having different amino acid sequences in their respective heavy and light chains) on their constant regions, and moreover without modification of variable regions. Provided are approaches that are particularly advantageous when conjugating larger drugs, hydrophobic drugs or charged drugs.

In one aspect, the present disclosure provides a site-specific labeling and functionalization approach that is particularly useful for functionalizing immunoglobulins with drugs or other moieties of interest, such that different immunoglublins species can be conjugated to a moiety of interest and compared to one another in such conjugated form. Comparison of different antibody species enables antibodies to be screened for a property of interest in conjugated form, for example for use in internalizing into and/or killing a cell, for labeling a cell, for increasing the stability (e.g. in serum, in aqueous solution, in a pharmaceutical formulation) of an antibody, etc. This presents advantages over classical methods of selecting antibodies suitable for use in a drug conjugate which typically involve basing development decisions on affinity, internalization or other criteria that are determined when the antibody is in non-conjugated form.

In one aspect, the present disclosure provides a method (e.g. a method for producing and/or evaluating an antibody), comprising providing a first and a second antibody each comprising at least one acceptor glutamine residue (e.g. one, two acceptor glutamines) in a constant region, wherein said second antibody differs from said first antibody in its variable region amino acid sequence; reacting said first and second antibody (separately or in the same container) with a lysine-based linker, in the presence of a TGase, under conditions sufficient to obtain a first and a second antibody each conjugated to a lysine-based linker. Optionally the method further comprises evaluating (e.g. comparing) the conjugated first and a second antibody for a characteristic of interest (e.g. toxicity to a target cell, cancer treatment efficacy, advantageous pharmaceutical properties such as (low) levels of aggregation or aggregattes, (high) levels of physicochemical stability, etc.). In one embodiment, the antibody comprises a heavy chain constant region of rodent origin (originating from a mammal of the order rodentia), for example a mouse, hamster or rat. In one embodiment, the antibody comprises a heavy chain constant region of human origin (e.g. a chimeric, human or humanized antibody).

In one embodiment, the first and a second antibody are each conjugated to a lysine-based linker comprising a moiety-of-interest (Z) by reacting the antibody with a lysine-based linker comprising a moiety-of-interest (Z) (e.g. a linker of Formula Ic).

In one embodiment, a first and a second antibody are each conjugated to a lysine-based linker comprising a moiety-of-interest (Z) by:
(i) reacting the antibody (i.e. the first and the second antibody) with a lysine-based linker comprising a reactive group (R) (e.g. a compound of Formula Ia or Ib) to obtain an antibody conjugated to such lysine-based linker comprising a reactive group (R) (e.g. an antibody of Formula II), and
(ii) further reacting the resulting antibody of step (i) (e.g. an antibody of Formula II) with a compound comprising: (a) a reactive group (R') that reacts with reactive group (R) on the lysine based linker, and (b) a moiety-of-interest (Z) (e.g., a compound of Formula III),
whereby a first and a second antibody each conjugated to a lysine-based linker comprising a moiety-of-interest (Z) is obtained (e.g. a first and a second antibody of Formula IV).

Preferably, the first and second antibody samples in steps a) and b) are reacted in separate containers.

In one embodiment, step (ii) comprises: immobilizing the resulting antibody of step (i) on a solid support to provide a sample comprising immobilized antibodies, reacting the sample comprising immobilized antibodies with a compound comprising: (a) a reactive group (R') that reacts with reactive group (R) on the lysine based linker, and (b) a moiety-of-interest (Z) (e.g., a compound of Formula III), and eluting the antibodies to provide an antibody sample comprising antibodies conjugated to a lysine-based linker comprising a moiety-of-interest (Z) (e.g. an antibody of Formula IV).

In one embodiment, the disclosure provides a method for making, evaluating and/or screening antibodies, comprising the steps of:

a) providing a first and second antibody sample each comprising a plurality of antibodies comprising at least one acceptor glutamine residue in a constant region, wherein the first and second antibody-containing samples differ from one another with respect to antibody quantity and/or antibody sequence (e.g. variable region sequence, CDR sequence(s)), wherein substantially all of the antibody present in the first sample is of the same sequence and substantially all of the antibody present in the second sample is of the same sequence; and b) reacting each of said first and second antibody sample with a lysine-based linker, in the presence of a TGase, under conditions sufficient such that antibodies in such first and second antibody samples are conjugated to a lysine-based linker.

Preferably, the first and second antibody samples in step b) are reacted in separate containers.

Optionally, the first and second antibody samples are specific for the same antigen.

Optionally, the conjugated antibodies obtained in step b) are conjugated to a moiety-of-interest (Z) via said lysine-based linker.

In one embodiment, step b) comprises: reacting each of said first and second antibody sample with a lysine-based linker comprising a moiety-of-interest (Z) (e.g. a linker of Formula Ic), in the presence of a TGase, under conditions sufficient such that antibodies in such first and second antibody samples are conjugated to a lysine-based linker comprising a moiety-of-interest (Z).

In one embodiment, step b) comprises:

(i) reacting each of said first and second antibody sample with a lysine-based linker comprising a reactive group (R) (e.g. a compound of Formula Ia or Ib) such that antibodies in such first and second antibody samples are conjugated to such lysine-based linker comprising a reactive group (R) (e.g. an antibody of Formula II), and (ii) further reacting the resulting first and second antibody samples of step (i) (e.g. an antibody of Formula II) with a compound comprising: (a) a reactive group (R') that reacts with reactive group (R) on the lysine based linker, and (b) a moiety-of-interest (Z) (e.g., a compound of Formula III), whereby the resulting antibodies in such first and second antibody samples are conjugated to a lysine-based linker comprising a moiety-of-interest (Z) is obtained (e.g. an antibody of Formula IV).

In one embodiment, step (ii) comprises: immobilizing the resulting first and second antibody samples of step (i) on a solid support to provide a first and second sample comprising immobilized antibodies, reacting the first and second sample comprising immobilized antibodies with a compound comprising: (a) a reactive group (R') that reacts with reactive group (R) on the lysine based linker, and (b) a moiety-of-interest (Z) (e.g., a compound of Formula III), optionally recovering any unreacted compound and re-introducing such recovered compound to the solid support for reaction with immobilized antibodies, and eluting the antibody conjugates to provide a first and second antibody sample comprising antibodies conjugated to a lysine-based linker comprising a moiety-of-interest (Z) (e.g. an antibody of Formula IV).

Preferably, step b) comprises: reacting each of said first and second antibody sample with a lysine-based linker of Formula Ia or Ib, in the presence of a TGase, under conditions sufficient such that antibodies of Formula II comprising a reactive moiety (R) are obtained, and further reacting the antibodies of Formula II to obtain antibodies of Formula IV comprising a moiety-of-interest (Z). Preferably, the antibodies of Formula II are reacted with a compound of Formula III to obtain antibodies of Formula IV comprising a moiety-of-interest (Z). In one embodiment, step b) comprises: reacting each of said first and second antibody sample with a lysine-based linker of Formula Ia or Ib, in the presence of a TGase, under conditions sufficient such that antibodies of Formula II comprising a reactive moiety (R) are obtained, immobilizing the resulting first and second antibody samples comprising antibodies of Formula II on a solid support to provide a first and second sample comprising immobilized antibodies, further reacting the first and second sample comprising immobilized antibodies with to obtain antibodies of Formula IV comprising a moiety-of-interest (Z). Preferably, the first and second sample comprising immobilized antibodies are reacted with a compound of Formula III to obtain antibodies of Formula IV comprising a moiety-of-interest (Z).

Preferably, in any the methods or compositions of the disclosure, an antibody sample comprising a plurality of antibody conjugates is obtained, wherein the antibodies have a uniform ratio of functionalized acceptor glutamines:antibody.

When the first and second antibody samples (e.g. in step b) are reacted in separate containers, separate first and second antibody samples having a uniform ratio of functionalized acceptor glutamines:antibody are obtained. Such compositions are useful in antibody screening, and the first and second compositions can be compared, for example, for use in further development of therapeutic and/or diagnostic applications. Optionally, at least 70%, 80%, 90%, 95%, 98% or 99% of the antibodies in said first and second antibody samples obtained have the same number of functionalized acceptor glutamine residues (Q) per antibody. Optionally, at least 70%, 80%, 90%, 95%, 98% or 99% of the antibodies in said first and second antibody samples obtained in step (b) have no more or no less than (m) functionalized acceptor glutamine residues (Q) per antibody, wherein m is an integer, e.g. m=1, 2, 3 or 4. Optionally, the first and second antibody samples obtained in step (b) each comprise a plurality of antibodies of Formula II or IV, wherein at least 70%, 80%, 90%, 95%, 98% or 99% of the antibodies in the composition have the same number of functionalized acceptor glutamine residues (Q) per antibody and at least 70%, 80%, 80%, 90%, 95%, 98% or 99% of the antibodies in the composition have the same q, r and z values.

When the first and second antibody samples (e.g. in step b) are reacted in the same container, a composition comprising both first and second antibody samples having a uniform ratio of functionalized acceptor glutamines:antibody are obtained. Such compositions are useful in applications where two or more antibodies are to be conjugated to a moiety of interest (e.g. a polyclonal antibody composition). Such antibodies may be directly useful in therapeutic and/or diagnostic applications, for example, to treat a cancer, an infectious disease or an autoimmune or inflammatory disorder.

In one embodiment the disclosure therefore provides a composition of a plurality of first and a plurality of second antibodies each comprising at least one acceptor glutamine residue in a constant region, wherein said second antibodies differ from said first antibodies in their variable region amino acid sequence and wherein substantially all (e.g. at least 90%, 95%, 98% or 99%) the antibodies in the composition comprise a functionalized acceptor glutamine on a heavy chain constant region (e.g. on a CH2 domain). Preferably, in any the methods or compositions of the disclosure, a composition of a plurality of antibody conjugates is obtained wherein the antibodies have a homogeneous ratio of functionalized acceptor glutamines:antibody. In one embodiment the disclosure provides a composition of a plurality of first and a plurality of second antibodies of Formula II or IV, each comprising at least one acceptor glutamine residue in a constant region, wherein said second antibodies differs from said first antibodies in their variable region amino acid sequence and wherein at least 70%, 80%. 85%, 90%, 95%, 98% or 99% of the antibodies in the composition have the same number of functionalized acceptor glutamine residues (Q) (e.g., a functionalized acceptor glutamine of Formula II or IV) per antibody. Preferably at least 70%, 80%. 85%, 90%, 95%, 98% or 99% of the antibodies in the composition have no more or no less than (m) functionalized acceptor glutamine residues (Q) per antibody, wherein m is an integer, e.g. m=1, 2, 3 or 4. Optionally, at least 70%, 80%, 90%, 95%, 98% or 99% of the antibodies in the composition have the same q, r and z values. It can be specified that the antibodies will share the same —NH—(C)$_n$—X, L, V, V', Y, Y', R, RR' and/or Z moieties.

In one aspect the disclosure provides a composition of a plurality of first and a plurality of second antibodies each comprising at least one acceptor glutamine residue in a constant region, wherein said second antibodies differ from said first antibodies in their variable region amino acid sequence (e.g. a plurality tetrameric or full-length antibodies), wherein the antibodies are linked (covalently) to a moiety of interest (Z), preferably via a linker, wherein the composition is characterized by a mean Z:antibody ratio (e.g. mean DAR) of close to 2 (e.g., between 1.5 and 2.0, or between 1.7 and 2.0, between 1.8 and 2.0, or between 1.9 and 2.0) less than 10%, less than 5%, less than 2% or less than 1% of the antibodies in the composition comprise more than two moieties of interest (Z) per antibody. Preferably the composition is substantially free of antibodies having more than 2 moieties of interest per antibody.

In one aspect the disclosure provides a composition of a plurality of first and a plurality of second antibodies each comprising at least one acceptor glutamine residue in a constant region, wherein said second antibodies differ from said first antibodies in their variable region amino acid sequence (e.g. a plurality tetrameric or full-length antibodies), wherein the antibodies are linked (covalently) to a moiety of interest (Z), preferably via a linker, wherein the antibodies have a mean Z:antibody ratio (e.g. mean DAR) of at least 1.5, 1.6, 1.7 or 1.8. Optionally, less than 10%, less than 5%, less than 2% or less than 1% of the antibodies in the composition comprise more than two moieties of interest (Z) per antibody. Preferably, less than 25%, 20%, 15% or preferably 10% of the antibodies in the composition comprise less than two moieties of interest (Z) per antibody.

In one aspect the disclosure provides a composition of a plurality of first and a plurality of second antibodies each comprising at least one acceptor glutamine residue in a constant region, wherein said second antibodies differ from said first antibodies in their variable region amino acid sequence (e.g. a plurality tetrameric or full-length antibodies), wherein the antibodies are linked (covalently) to a moiety of interest (Z), preferably via a linker, wherein:

the antibodies have a mean Z:antibody ratio (e.g. mean DAR) of at least 1.5, 1.6, 1.7 or 1.8,
optionally, less than 10%, less than 5%, or less than 2% of the antibodies comprise more than two functionalized acceptor glutamines per antibody, and
less than 25%, 20%, 15% or preferably 10% of the antibodies comprise less than two moieties of interest (Z) per antibody.

Optionally, in any of the embodiments of the disclosure, the antibodies are linked to said moiety of interest (Z) via one functionalized acceptor glutamine (e.g. a functionalized acceptor glutamine of Formula II or IV) on each heavy chain of the antibody. Optionally, at least 70%, 80%. 85%, 90%, 95%, 98% or 99% of the antibodies in the composition comprise one functionalized acceptor glutamine (e.g. a functionalized acceptor glutamine of Formula II or IV) on each heavy chain.

In one aspect the disclosure provides a composition of a plurality of first and a plurality of second antibodies each comprising at least one acceptor glutamine residue in a constant region, wherein said second antibodies differ from said first antibodies in their variable region amino acid sequence (e.g. a plurality tetrameric or full-length antibodies), wherein the antibodies are linked (covalently) to a moiety of interest (Z), preferably via a linker, wherein the composition is characterized by a mean Z:antibody ratio (e.g. mean DAR) of close to 4 (e.g., between 3.0 and 4.0, or between 3.5 and 4.0, or between 3.6 and 4.0) wherein less than 10%, less than 5%, or less than 2% of the antibodies comprise more than four functionalized acceptor glutamines per antibody. Preferably, the composition is substantially free of antibodies having more than 4 moieties of interest (Z) per antibody.

In one aspect the disclosure provides a composition of a plurality of first and a plurality of second antibodies each comprising at least one acceptor glutamine residue in a constant region, wherein said second antibodies differ from said first antibodies in their variable region amino acid sequence (e.g. a plurality tetrameric or full-length antibodies), wherein the antibodies are linked to a moiety of interest (Z), preferably via a linker, wherein the antibodies have a mean Z:antibody ratio (e.g. mean DAR) of at least 3.2, 3.4, 3.5 or 3.6. Optionally, less than 10%, less than 5%, or less than 2% of the antibodies comprise more than four functionalized acceptor glutamines per antibody.

Preferably the antibodies in the compositions are linked to said moiety of interest (Z) on each of two functionalized acceptor glutamines (e.g. a functionalized acceptor glutamine of Formula II or IV) on each heavy chain of the antibody. Optionally, the antibodies are linked to said moiety of interest (Z) via two functionalized acceptor glutamines (e.g. a functionalized acceptor glutamine of Formula II or IV) on each heavy chain of the antibody. Optionally, at least 70%, 80%, 85%, 90% of the antibodies in the composition comprise two functionalized acceptor glutamines (e.g. a functionalized acceptor glutamine of Formula II or IV) on each heavy chain.

Optionally, in any of the embodiments of the disclosure, the method further comprises a step (c): evaluating antibodies from said first and second antibody sample obtained in step (b) for a characteristic of interest. Optionally, said step of evaluating antibodies for a characteristic of interest comprises evaluating antibodies for one or more properties selected from the group consisting of: binding to an antigen of interest, binding to an Fc receptor, Fc-domain mediated effector function(s), agonistic or antagonistic activity at a polypeptide to which the antibody, ability to cause the death of a cell expressing the antigen of interest, stability in vitro or in vivo, and susceptibility to aggregate in solution.

Optionally, the method further comprises a step (c): evaluating antibodies from said first and second antibody sample obtained in step (b) for their suitability for use as an antibody-drug conjugate. Optionally, said step of evaluating antibodies for suitability of the antibodies for use as an antibody-drug conjugate comprises evaluating the antibodies for their ability to cause the death of a cell expressing the antigen of interest.

In one embodiment, the antibodies in the first and second antibody samples are specific for the same antigen (e.g. a (poly)peptide, carbohydrate, polymer, biological target, cancer antigen, bacterial antigen, viral antigen).

In one aspect, the method is a method for evaluating (e.g. screening) antibodies that bind to a predetermined antigen of interest (e.g. a (poly)peptide, carbohydrate, polymer, biological target, cancer antigen, or bacterial antigen, viral antigen).

In one aspect, the present disclosure provides a method for identifying an antibody suitable for use in an antibody-drug conjugate, comprising the steps of:

a) providing a first antibody (or first antibody sample) specific for an antigen of interest, the first antibody comprising at least one acceptor glutamine residue in a constant region, reacting said antibody with a lysine-based linker of Formula Ic, in the presence of a TGase, under conditions sufficient such that the antibody is conjugated to a lysine-based linker comprising a moiety-of-interest (Z) (e.g. an antibody of Formula IV), or b) providing a second antibody (or second antibody sample) specific for said antigen of interest, the second antibody comprising at least one acceptor glutamine residue in a constant region, wherein said second antibody differs from said first antibody in its amino acid sequence (e.g. variable region amino acid sequence), and reacting said antibody with a lysine-based linker of Formula Ic, in the presence of a TGase, under conditions sufficient such that the first and second antibodies are conjugated to a lysine-based linker comprising a moiety-of-interest (Z) (e.g. an antibody of Formula IV); and c) evaluating said first and second antibodies for their suitability for use as an antibody-drug conjugate, optionally wherein the antibodies are evaluated for their ability to cause the death of a cell expressing the antigen of interest.

In one aspect, the present disclosure provides a method for identifying an antibody suitable for use in an antibody-drug conjugate, comprising the steps of:

a) providing a first antibody (or first antibody sample) specific for an antigen of interest, the first antibody comprising at least one acceptor glutamine residue in a constant region, reacting said antibody with a lysine-based linker of Formula Ia or Ib, in the presence of a TGase, under conditions sufficient such that antibodies of Formula II are obtained, and further reacting the antibodies of Formula II to obtain antibodies of Formula IV comprising a cytotoxic moiety Z, and b) providing a second antibody (or second antibody sample) specific for said antigen of interest, the second antibody comprising at least one acceptor glutamine residue in a constant region, wherein said second antibody differs from said first antibody in its amino acid sequence (e.g. variable region amino acid sequence), and reacting said antibody with a lysine-based linker of Formula Ia or Ib, in the presence of a TGase, under conditions sufficient such that antibodies of Formula II are obtained, and further reacting the antibodies of Formula II to obtain antibodies of Formula IV comprising a cytotoxic moiety Z; and c) evaluating said first and second antibodies for their suitability for use as an antibody-drug conjugate, optionally wherein the antibodies are evaluated for their ability to cause the death of a cell expressing the antigen of interest.

Preferably, the antibodies of Formula II are reacted with a compound of Formula III to obtain antibodies of Formula IV.

In one aspect of any of the embodiments herein, the first and second antibody-containing samples differ from one another with respect to antibody quantity and/or antibody sequence, wherein substantially all of the antibody present in the first sample is of the same sequence and substantially all of the antibody present in the second sample is of the same sequence.

In one aspect of any of the embodiments herein, the antibodies or antibody samples are provided in the form of unpurified hybridoma supernatant, e.g. from rat or a mouse origin following immunization of such rat or mouse. Optionally, the hybridoma supernatant comprises unquantified antibody produced from a plurality of hybridoma clones, wherein the plurality of samples vary with respect to antibody quantity and antibody sequence provided that, in a majority of the plurality of the samples, substantially all of the antibody present in each sample is from a single hybridoma clone.

The present approach provides for antibody compositions that have uniform conjugated acceptor glutamine:antibody stoichiometry that enables a direct comparison of different antibodies.

In one aspect of any of the embodiments herein, the antibodies comprise a human heavy and/or light chain constant region. Optionally the antibodies are tetrameric or full-length antibodies. Optionally, the antibodies comprise one acceptor glutamine residue in a heavy chain constant region. Optionally, the antibodies comprise more than one acceptor glutamine residue in a heavy chain constant region.

Preferably the heavy chain constant region has the amino acid sequence of a naturally occurring human heavy chain constant region (e.g., is not a glutamine-engineered antibody).

Preferably, each of the first and second antibodies are free of N-linked glycosylation (i.e. on residues N297 of the heavy chain) prior to their reaction with a lysine based linker. Optionally, steps (a) and (b) each comprise a step of treating said antibody to remove N-linked glycosylation prior to their reaction with a lysine based linker of Formula I.

The conjugation of lysine-based linker with the first or second antibody occurs on one or more acceptor glutamine residues present in the antibody outside of the antigen combining site. The lysine-based linker may comprise any suitable moiety of interest, for example a drug or diagnostic moiety, a moiety that improves the pharmacokinetic properties, or a reactive moiety that can subsequently be reacted with a compound comprising a drug or diagnostic moiety. The present approach provides for antibody compositions that have uniform conjugated acceptor glutamine:antibody stoichiometry that enables a direct comparison of different antibodies.

In one embodiment, the first and second antibodies are deglycosylated (i.e. no glycosylation on the residue at position 297 (EU numbering) of the heavy chain) prior to the step of reacting antibodies in the presence of a TGase in steps a) and/or b). In one embodiment, the methods comprise a step of deglycosylating said first and second antibodies (i.e. to remove glycosylation on the residue at position 297 (EU numbering) of the heavy chain) prior to the step of reacting antibodies in the presence of a TGase in step a) and/or c). In one embodiment, the first and second antibodies differ in the amino acid sequence of their heavy and light chains. In one embodiment, the first and second antibodies differ in the amino acid sequence of their heavy and light chains and bind to the same biological target (e.g. a polypeptide).

In one embodiment, the first and second antibodies differ in the amino acid sequence of their heavy and light chain variable regions (or CDRs).

In one embodiment, the first and second antibodies differ in the amino acid sequence of their heavy and light chain constant regions. In one embodiment, the first and second antibodies have heavy chains of different isotypes. In one embodiment, the first and second antibodies differ in the amino acid sequence of their heavy chain constant regions and have heavy chains of the same isotypes.

In one embodiment, the disclosure provides a method for evaluating (e.g. comparing) a biological target, e.g. for suitability for targeting by an antibody, wherein the first and second antibodies differ in the amino acid sequence of their heavy and light chains variable regions and bind to a different biological target. A determination that a first antibody is improved for a property of interest, e.g. a biological activity, indicates that the biological target (i.e. antigen) recognized by such first antibody is a suitable or better biological target than the biological target recognized by the second antibody.

In one embodiment, the disclosure provides a method for evaluating a particular antibody amino acid sequence or an epitope on a biological target, e.g. for suitability for targeting by an antibody, wherein the first and second antibodies differ in the amino acid sequence of their heavy and light chain variable regions and bind the same biological target. The antibodies may have different binding characteristics, e.g. binding affinity, on or off rates, differing ability to trigger internalization of the antibody/receptor complex. The antibodies may optionally further bind to a different epitopic site on the biological target. A determination that a first antibody is improved for a property of interest, e.g. a biological activity, may indicate that the epitope (the epitope on a biological target) recognized by such first antibody is a suitable biological target or a better biological target than the epitope (e.g., the epitope on the same biological target) recognized by the second antibody.

Optionally, the method comprises at least 3, 4, 5, 10, 20, 50 or 100 further steps a') and b') such that a larger number of antibodies are included in the method of evaluation. Optionally, the method further comprises selecting an antibody from said first and second (or further) antibody which has an improved characteristic of interest. Optionally, the method further comprises producing a quantity of said selected antibody.

In one embodiment, the antibodies have human framework sequences in their variable regions (i.e. the antibodies are human or humanized antibodies).

In one aspect, the step of providing an antibody or sample of antibodies comprises generating a plurality (e.g. a library, collection) of candidate antibodies that bind an antigen of interest, wherein said plurality comprises a first and a second antibody, optionally wherein said step of generating candidate antibodies comprises immunizing animal(s) with an antigen of interest or generating or selecting from a combinatorial libraries of immunoglobulins to generate a plurality of candidate antibodies that bind the antigen of interest.

An acceptor glutamine at position 295 will be naturally present in all human antibody gamma isotypes, which together with a method of conjugation permits stoichiometric conjugation and direct screening of different antibodies a variety of drug or other components. In one embodiment, the disclosure provides an antibody (of human origin) conjugated on an acceptor glutamine residue to a moiety-of-interest via a lysine-based linker, wherein the acceptor glutamine is present within the CH2 domain, preferably at position 295 (Kabat numbering). The antibody will preferably be a IgG1, IgG2, IgG3 or IgG4 antibody, preferably comprising a naturally occurring CH2 amino acid sequence or constant region sequence. In another embodiment, the antibody will be a glutamine-engineered antibody in which one or more glutamines is introduced or removed (e.g. by substitution with a different amino acid) from a heavy chain constant region.

An acceptor glutamine at position 288 or 290 (EU numbering) will be naturally present in murine antibody gamma 1, 2a and 2b isotypes. The disclosure relates in one embodiment to a method for conjugating a moiety of interest (Z) to an antibody having a non-human heavy chain constant region, comprising the steps of:

a) providing an antibody comprising a heavy chain constant region of rodent origin (e.g. murine, rat), for example an antibody having an acceptor glutamine residue within the heavy chain constant region); and b) reacting said antibody with a linking reagent comprising a primary amine (e.g. a lysine-based linker) and a moiety of interest, in the presence of a transglutaminase enzyme capable of causing the formation of a covalent bond between the acceptor glutamine residue and the linking reagent (at the primary amine of the linking reagent), under conditions sufficient to obtain an antibody comprising an acceptor glutamine residue linked (covalently) to the linking reagent. Optionally, the step of providing an antibody in section (a) comprises immunizing a rodent (e.g. mouse, rat) with an antigen, and obtaining an antibody from such rodent.

In one embodiment, said heavy chain constant region comprises an acceptor glutamine at position 288 or 290 (EU numbering)

In one embodiment, the moiety of interest is a moiety (Z) that improves the pharmacokinetic properties, a therapeutic moiety, or diagnostic moiety.

In one embodiment, the moiety of interest is an organic compound that is electrically negatively charged, hydrophobic and/or that has a molecular weight of at least 400 g/mol, 500 g/mol, 600 g/mol, 700 g/mol, 800 g/mol, 900 g/mol, 1000 g/mol or 2000 g/mol; optionally the moiety of interest (Z) is an anticancer agent selected from the group consisting of taxanes, anthracyclines, camptothecins, epothilones, mytomycins, combretastatins, vinca alkaloids, nitrogen mustards, maytansinoids, calicheamycins, duocarmycins, tubulysins, dolastatins and auristatins, enediynes, amatoxins, pyrrolobenzodiazepines, ethylenimines, radioisotopes, therapeutic proteins and peptides, and toxins or fragments thereof.

In one embodiment, said moiety of interest of step (b) is a reactive group (R), optionally a protected reactive group and the method further comprises a step (c): reacting the composition comprising a plurality of antibodies obtained in step (b), optionally immobilized on a solid support, with a compound comprising (i) a moiety (Z) that improves pharmacokinetic properties, a therapeutic moiety or a diagnostic moiety, and (ii) a reactive group (R') capable of reacting with reactive group R, under conditions sufficient to obtain a composition comprising antibodies comprising an acceptor glutamine linked to a moiety (Z) via said linking reagent, The disclosure relates in one embodiment to an antibody having a heavy chain constant region of rodent origin (e.g. murine, rat) wherein the constant region comprises an acceptor glutamine functionalized with a linking reagent. In one embodiment, the acceptor glutamine is an acceptor glutamine of Formulae Ia, Ib, Ic, II, or IV (e.g. IVa or IVb). In one embodiment, the constant region or antibody is of murine IgG1, IgG2a or IgG2b isotype.

In one embodiment provided is an antibody or antibody fragment comprising a heavy chain constant region of rodent origin (e.g. murine, rat) having a functionalized acceptor glutamine residue (e.g. in a CH2 domain, at residue 288 or 290 (EU numbering)), the functionalized acceptor glutamine residue having Formula IVa,

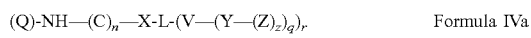
Formula IVa or a pharmaceutically acceptable salt or solvate thereof, wherein:

Q is a glutamine residue present in a heavy chain constant region of the antibody or antibody fragment;

$(C)_n$ is a substituted or unsubstituted alkyl or heteroalkyl chain, optionally wherein any carbon of the chain is substituted with an alkoxy, hydroxyl, alkylcarbonyloxy, alkyl-S—, thiol, alkyl-C(O)S—, amine, alkylamine, amide, or alkylamide;

n is an integer selected from among the range of 2 to 20;

X is NH, O, S, absent, or a bond;

L comprises a linear framework of 5 to 30 carbon atoms optionally substituted at one or more atoms;

r is an integer selected from among 1, 2, 3 or 4;

q is an integer selected from among 1, 2, 3 or 4;

z is an integer selected from among 1, 2, 3 or 4; and

V is independently absent, a bond or a continuation of a bond, a non-cleavable moiety or a conditionally-cleavable moiety;

Y is independently absent, a bond or a continuation of a bond, or a spacer system which is comprised of 1 or more spacers; and Z is a moiety that improves pharmacokinetic properties, a therapeutic moiety or a diagnostic moiety. Optionally, Z is an organic compound that is electrically negatively charged, hydrophobic and/or that has a molecular weight of at least 400 g/mol. Optionally, Z is a detectable moiety (e.g. a diagnostic moiety, a detectable label, a fluorescent moiety).

In one embodiment provided is an antibody or antibody fragment comprising a heavy chain constant region of rodent origin (e.g. murine, rat) having a functionalized acceptor glutamine residue (e.g. in a CH2 domain, at residue 288 or 290 (EU numbering)), the functionalized acceptor glutamine residue having Formula IVb,

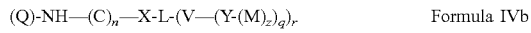
Formula IVb or a pharmaceutically acceptable salt or solvate thereof, wherein:

Q is a glutamine residue present in an antibody or antibody fragment;

$(C)_n$ is a substituted or unsubstituted alkyl or heteroalkyl chain, optionally wherein any carbon of the chain is substituted with a alkoxy, hydroxyl, alkylcarbonyloxy, alkyl-S—, thiol, alkyl-C(O)S—, amine, alkylamine, amide, or alkylamide;

n is an integer selected from among the range of 2 to 20;

X is NH, O, S, absent, or a bond;

L is independently absent, a bond or a continuation of a bond, or a carbon comprising framework of 1 to 200 atoms substituted at one or more atoms, optionally, wherein the carbon comprising framework comprises a linear framework of 3 to 30 carbon atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

r is an integer selected from among 1, 2, 3 or 4;

q is an integer selected from among 1, 2, 3 or 4;

z is an integer selected from among 1, 2, 3 or 4;

V is independently absent, a bond or a continuation of a bond, a non-cleavable moiety or a conditionally-cleavable moiety;

Y is independently absent, a bond or a continuation of a bond, or a spacer system which is comprised of 1 or more spacers;

M is independently: R or $(RR')\text{-}L'\text{-}(V'\text{---}(Y'\text{---}(Z)_{z'})_{q'})_{r'}$, wherein R is a reactive moiety;

(RR') is an addition product between R and a complementary reactive moiety R';

L' is independently absent, a bond or a continuation of a bond, or a carbon comprising framework of 1 to 200 atoms substituted at one or more atoms, optionally, wherein the carbon comprising framework comprises a linear framework of 3 to 30 carbon atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

V' is independently absent, a bond or a continuation of a bond, a non-cleavable moiety or a conditionally-cleavable moiety;

Y' is independently absent, a bond or a continuation of a bond, or a spacer system which is comprised of 1 or more spacers;

Z is independently a reactive group, a moiety that improves the pharmacokinetic properties, a therapeutic or diagnostic moiety, and each Z is directly coupled to either Y or V when Y is absent, or L when both Y and V are absent; and z', q' and r' are each independently an integer selected from among 1, 2, 3 or 4.

In one embodiment, provided is a composition comprising a plurality of such antibodies or antibody fragments comprising a heavy chain constant region of rodent origin with a functionalized acceptor glutamine residue. In one embodiment, the plurality of antibodies in the composition substantially all have the same variable region amino acid sequence. In one embodiment, the plurality of antibodies in the composition comprises antibodies having different variable region amino acid sequences. In one embodiment, the plurality of antibodies in the composition are obtained by immunizing a rodent (e.g. a mouse, a rat) with an antigen. Optionally, at least 70%, 80%, 85%, 90% of the antibodies in the composition comprise one functionalized acceptor glutamine (e.g. a functionalized acceptor glutamine of Formula II or IV) on each heavy chain.

As presented herein, the glutamine residue is part of the immunoglobulin and the lysine-based linker is part of the moiety that is conjugated to the glutamine residue on the immunoglobulin. The primary amino group is preferably separated by at least five (CH$_2$)— groups or a spacer of equal length from the moiety-of-interest. The antibodies of the disclosure are created through use of a linking reagent that can be attached, by the action of a TGase, to a polypeptide at a glutamine residue (Q) within the sequence of the polypeptide, for example an antibody (Ab). The linking reagent comprises a lysine derivative (Lys), or a functional equivalent thereof, that is connected to at least one reactive group. In one embodiment, a moiety-of-interest (Z) can be attached to the linking reagent. In one embodiment, a plurality of reactive groups, preferably non-complementary reactive groups, can be attached to the linking reagent. The reactive group is preferably a functionality that is insensitive to water but selectively undergoes a very high conversion addition reaction with a complementary reagent. The functional equivalent of a lysine derivative comprises a 2 to 20 carbon chain, or a functional equivalent thereof, with an aminomethylene (H$_2$NCH$_2$) group or a protected H$_2$NCH$_2$ group that can be derived from the aminomethylene positioned at one or more ends of the carbon chain. The functional equivalent of the carbon chain is a chain of 3 to 20 atoms where one or more non-terminal atoms can be other than carbon, for example oxygen, sulfur, nitrogen, or other atoms. The oxygen, sulfur, or nitrogen atom can be of an ether, ester, thioether, thioester, amino, alkylamino, amido or alkylamido functionality within the carbon chain.

One exemplary functional equivalent of the carbon chain is an oligo (ethylene oxide) chain. The functionality within the carbon chain can be included to couple the reactive group to the H$_2$NCH$_2$ group or protected H$_2$NCH$_2$ group. The carbon chain, or its functional equivalent, can be substituted or unsubstituted. The substituents can be alkyl groups, aryl groups, alkyl aryl groups, carboxylic acid groups, amide groups, hydroxy groups, or any other groups that do not compete with the amino group for, or inhibit, conjugation with a glutamine residue of the protein. Typically, when a substituent is present, its presence is in a convenient starting material, such as the carboxylic acid group of lysine, from which the lysine derivative results. The aminomethylene end of a carbon chain is necessarily included in the linking reagent.

Starting materials for the functional equivalent of lysine can be an α,ω-diaminoalkane, for example, 1,2-diaminoethane, 1,3-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, 1,11-diaminoundecane, or 1,12-diaminododecane. Other starting materials for the functional equivalent of a lysine derivative can be α,ω-diamino oligo (ethylene oxide), for example, H$_2$N(CH$_2$CH$_2$O)$_x$CH$_2$CH$_2$NH$_2$ where x is 1 to about 6. The α,ω-diamino oligo (ethylene oxide) can be a single oligomer or it can be a mixture of oligomers where x defines an average size. An exemplary protected H$_2$NCH$_2$ is the tert-butylcarbamate protected amine of tert-butyl N-(5-aminopentyl)carbamate (N-Boc-cadaverine).

In one embodiment, an antibody described herein can comprise an acceptor glutamine residue (Q), wherein the antibody is conjugated (i.e., covalently attached) via said acceptor glutamine residue (Q) to one or more moieties-of-interest (Z) through a linker that comprises a NH—(C)$_n$— moiety, optionally wherein the linker further comprises a RR' moiety, a V (or V') moiety, and/or a Y (or Y') moiety.

Optionally, in any embodiment herein (e.g. Formulae I to IV), (C)$_n$ is a substituted or unsubstituted alkyl or heteroalkyl chain, optionally wherein any carbon of the chain is substituted with an alkoxy, hydroxyl, alkylcarbonyloxy, alkyl-S—, thiol, alkyl-C(O)S—, amine, alkylamine, amide, or alkylamide. Optionally, in any embodiment herein (e.g. Formulae I to IV), (C)$_n$ is a substituted or unsubstituted carbon chain having an unsubstituted carbon adjacent to NH, wherein any carbon of the chain, preferably other than the carbon adjacent to the NH, is optionally substituted with a O, N or S atom of an ether, ester, thioether, thioester, amine, alkylamine, amide, or alkylamide.

Optionally, in any embodiment herein (e.g. Formulae I to IV), the linking reagent comprises a linking moiety (L). Optionally, in any embodiment herein, L is a bond or a carbon comprising framework of 1 to 200 atoms substituted at one or more atoms, optionally wherein the carbon comprising framework is a linear hydrocarbon, a symmetrically or asymmetrically branched hydrocarbon monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process. Optionally, in any embodiment herein, L is independently absent, a bond or a continuation of a bond, or a carbon comprising framework of 5 to 200 atoms substituted at one or more atoms, optionally, wherein the carbon comprising framework comprises a linear framework of 5 to 30 carbon atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process.

In one embodiment, an antibody described herein can comprise a functionalized acceptor glutamine residue (Q) having Formula IV, below, (Q)-NH—(C)$_n$—X-L-(V—(Y-(M or Z)$_z$)$_q$)$_r$     Formula IV where:
Q is glutamine residue present in an antibody;
(C)$_n$ is a substituted or unsubstituted alkyl or heteroalkyl chain, optionally wherein any carbon of the chain is substituted with an alkoxy, hydroxyl, alkylcarbonyloxy, alkyl-S—, thiol, alkyl-C(O)S—, amine, alkylamine, amide, or alkylamide;
n is an integer selected from among the range of 2 to 20;
X is NH, O, S, or absent;
L is independently absent, a bond or a continuation of a bond, or a carbon comprising framework of 5 to 200 atoms substituted at one or more atoms, optionally, wherein the carbon comprising framework comprises a linear framework of 5 to 30 carbon atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

r is an integer selected from among 1, 2, 3 or 41 to 4;
q is an integer selected from among 1, 2, 3 or 41 to 4;
z is an integer selected from among 1, 2, 3 or 41 to 4; and
V is independently absent, a non-cleavable moiety or a conditionally-cleavable moiety, optionally following prior conditional transformation, which can be cleaved or transformed by a chemical, photochemical, physical, biological, or enzymatic process (e.g. cleavage of V ultimately leading to release of one or more moieties subsequently or ultimately linked to V, for example a Z moiety). In some embodiments, V is, preferably, a di-, tri-, tetra-, or oligopeptide as described below in the section entitled "The V Moiety";

Y is independently absent, being a bond or a continuation of a bond if V is a bond or continuation of a bond, or a spacer system (e.g., a self-eliminating spacer system or a non-self-elimination spacer system) which is comprised of 1 or more spacers;

Z is a moiety-of-interest; and

M is independently: R or (RR')-L'(V'—(Y'—(Z)$_z$)$_{q'}$)$_{r'}$, wherein each of L', V', Y', z', q', and r' are as defined in Formula III, Z is a moiety-of-interest, optionally a moiety that improves the pharmacokinetic properties, or a therapeutic moiety or a diagnostic moiety, R is as defined in Formula I and wherein each (RR') is an addition product between an R of Formula I and its complementary R' of formula III (see, for example, FIG. 1 and FIG. 2). RR' is preferably an addition product of a: thio-maleimide (or haloacetamine) addition, for example, a N,S-disubstituted-3-thio-pyrrolidine-2,5-dione; Staudinger ligation, for example, a N,3- or N,4-substituted-5-dipenylphosphinoxide-benzoic amide; Huisgen 1,3-cycloaddition (click reaction), for example, a N,S-disubstituted-3-thio-pyrrolidine-2, 5-dione, 1,4-disubstituted-1,2,3-triazole, 3,5-disubstituted-isooxazole, or 3,5-disubstituted-tetrazole; Diels-Alder cycloaddition adduct, for example the 2,4-cycloaddition product between an O or N-substituted-5-norbornene-2-carboxylic ester or amide, N-substituted-5-norbornene-2,3-dicarboxylic imide, O or N-substituted-7-oxonorbornene-5-carboxylic ester or amide, or N-substituted-7-oxonorbornene-5,6-dicarboxylic imide and a 9-substituted anthracene or 3-substituted 1,2,4,5-tetrazine; or any high yield selective amidation or imidization reaction. Some reactions and the corresponding RR' reaction products are illustrated in FIGS. 1 and 2.

Optionally, Formula IV will comprise V or V' (but not both V and V'). Optionally, Formula IV will comprise Y or Y' (but not both Y and Y').

In one embodiment, any antibody (e.g., a murine, rat, human or humanized antibody or any antibody comprising an acceptor glutamine in a heavy chain constant region), can be characterized as comprising a functionalized acceptor glutamine residue (Q) having Formula II (e.g. an intermediate product).

It will be appreciated that Formula II and IV can for convenience also be expressed as (Ab)-NH—(C)$_n$—X-L-(V—(Y—(R)$_z$)$_q$)$_r$, (Ab)-NH—(C)$_n$—X-L-(V—(Y-(M)$_z$)$_q$)$_r$ and (Ab)-NH—(C)$_n$—X-L-(V—(Y—(Z)$_z$)$_q$)$_r$, respectively, where (Ab) is an immunoglobulin (Ab) is conjugated via a glutamine (Q) residue to an NH of the linking reagent (e.g the compound of Formula I).

In any of Formulas herein, q, q', r and r' may optionally be specified to represent degree of branching or polymerization.

In Formula IV, the total number of R or Z moieties per antibody is preferably from about 1 to about 16. An example includes a composition comprising a plurality of antibody compounds of Formula IV, wherein substantially each antibody of such plurality has 1, 2, 3, 4, 5, 6, 8, 10, 12, 14 or 16 moieties Z per antibody. In one embodiment, the antibody of Formula II or IV has one, two or four functionalized acceptor glutamine residue and z=1, q=1 and r=1. In one embodiment, the antibody of Formula II or IV has one, two or four functionalized acceptor glutamine residues and z=2, 3 or 4, q=1 and r=1. In one embodiment, the antibody of Formula II or IV has one, two or four functionalized acceptor glutamine residue and z=1, 2, 3 or 4, q=2 and r=1. In one embodiment, the antibody of Formula II or IV has one, two or four functionalized acceptor glutamine residue and z=1, 2, 3 or 4, q=1 and r=2. In one embodiment provided is an antibody composition in which Z (e.g. drug) loading per antibody is uniform.

In one embodiment the antibody is a full-length antibody. In another embodiment, antibody is an antibody fragment or derivative, e.g. a Fv, Fab, Fab', F (ab')2 or a nanobody, domain antibody, single domain antibody or a "dAb". In one embodiment, the fragment or derivative (e.g. a Fab, Fab', F (ab')2 comprises a CH1 (e.g., comprising a hinge region) and/or CH2 domain or a portion thereof, wherein the CH2 comprises an acceptor glutamine residue. Optionally, said glutamine residue is at the C terminus of the heavy and/or light chain. In one embodiment, the fragment or derivative (e.g. a Fv, Fab, Fab', F (ab')2, nanobody, domain antibody, single domain antibody or "dAb") comprises a peptide tag comprising an acceptor glutamine residue (e.g. wherein the tag is fused to a variable region of the fragment).

Reference to "Formulas I", "Formula II", "Formula III" or "Formula IV", unless the context clearly indicates otherwise, designates all compounds derived from such Formulas I to IV, including e.g., Formula I includes reference to Ia, Ib and/or Ic, Formula IV includes IVa and IVb.

Any of the methods described herein can further be characterized as comprising any step described in the application, including notably in the "Detailed Description of the Invention"). Further provided is an antibody obtainable by any of present methods. Further provided are pharmaceutical or diagnostic formulations of the antibodies of the present invention. Further provided are methods of using an antibody in a method of treatment or diagnosis. The disclosure of U.S. application Ser. No. 13/725,385 filed on Dec. 21, 2012, and entitled "Enzymatic Conjugation of Polypeptides" is hereby incorporated by reference in its entirety.

These and additional advantageous aspects and features may be further described elsewhere herein.

DETAILED DESCRIPTION OF THE INVENTION

Introduction

Figure 1:
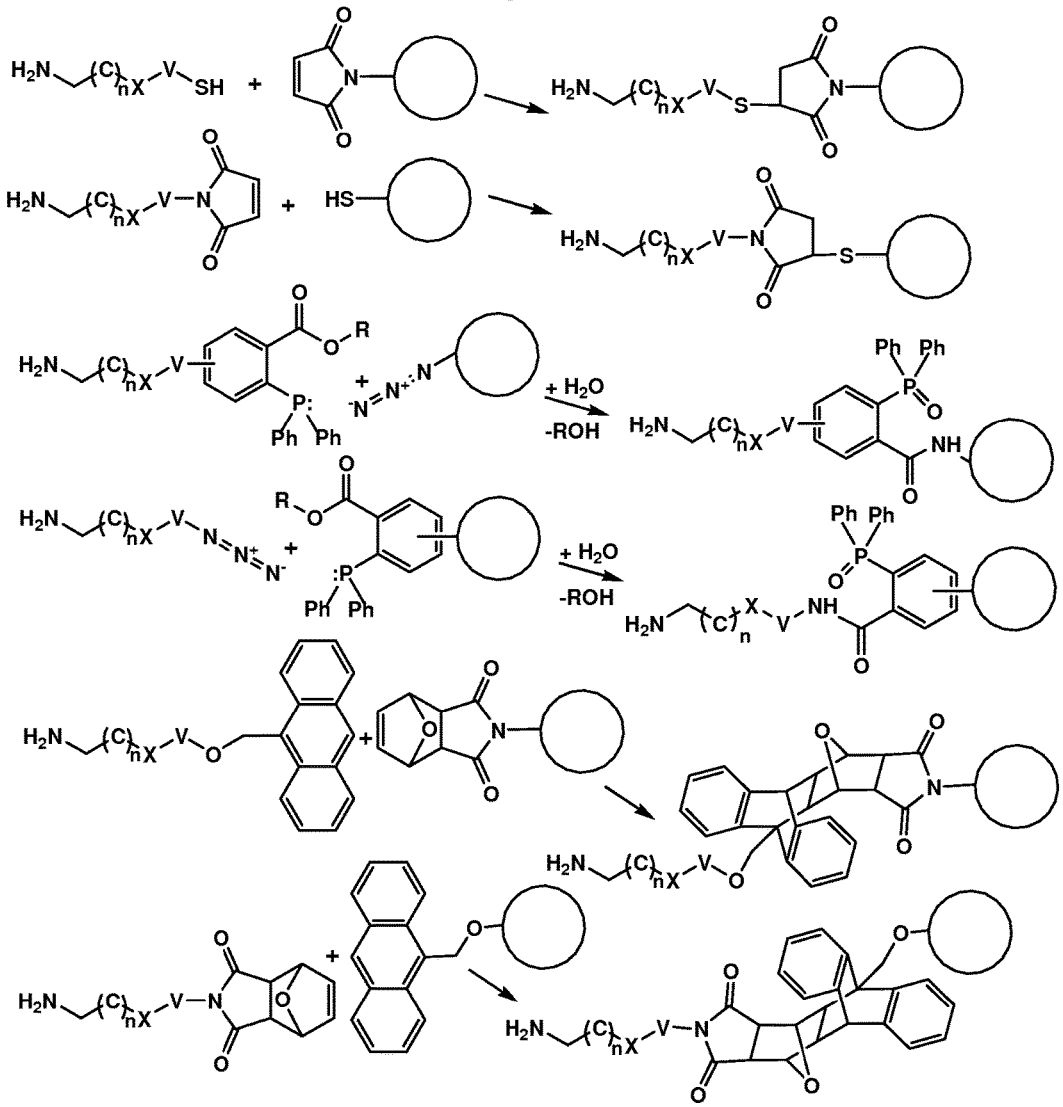
FIG. 1 shows reaction schemes for thio-maleimide additions, Staudinger ligations, and Diels-Alder cycloadditions, where reactive groups of linking reagents having a single reactive functionality combine with complementary reactive group attached to a therapeutic or diagnostic moiety.

According to the methods described herein, the functionalization of antibodies is site-specific and occurs via, respectively between a lysine or lysine-like moiety and an acceptor glutamine residue of an antibody by transglutaminase.

The inventors now present a convenient method for screening a plurality of different antibodies conjugated to a moiety-of-interest without the need to make modifications in the antibodies primary sequence, or to otherwise modify or derivatize the antibodies, prior to such conjugation. The method enables a screening protocol where different antibodies can be directly conjugated and then compared for bioactivity or other properties of interest. The method also enables the production of a composition of conjugated antibodies wherein antibodies are contained in the same container for conjugation, or in different containers but without the need to separately identify new reaction conditions for the site-specific functionalization of immunoglobulins. The enzymatic activity of the transglutaminase family catalyzes an acyl transfer reaction between the γ-carboxamide groups of peptide-bound glutamine residues and various primary amines or ε-amino groups of lysine residues, thus forming isopeptidic bonds which are stable and resistant to chemical, enzymatic, and physical degradation. The function of TGases can be described as incorporation of alkylamine derivatives into specific glutamine residues or vice versa.

Definitions

As used in the specification, "a" or "an" may mean one or more. As used in the claim(s), when used in conjunction with the word "comprising", the words "a" or "an" may mean one or more than one.

Where "comprising" is used, this can preferably be replaced by "consisting essentially of", more preferably by "consisting of".

The term "transglutaminase", used interchangeably with "TGase" or "TG", refers to an enzyme capable of cross-linking proteins through an acyl-transfer reaction between the γ-carboxamide group of peptide-bound glutamine and the s-amino group of a lysine or a structurally related primary amine such as amino pentyl group, e.g. a peptide-bound lysine, resulting in a ε-(γ-glutamyl)lysine isopeptide bond. TGases include, inter alia, bacterial transglutaminase (BTG) such as the enzyme having EC reference EC 2.3.2.13 (protein-glutamine-γ-glutamyltransferase).

The term "acceptor glutamine", when referring to an amino acid residue of an antibody, means glutamine residue that, under suitable conditions, is recognized by a TGase and can be cross-linked by a TGase through a reaction between the glutamine and a lysine or a structurally related primary amine such as amino pentyl group. The acceptor glutamine is typically a surface-exposed glutamine residue.

The term "antibody" herein is used in the broadest sense and specifically includes full-length monoclonal antibodies, polyclonal antibodies, multispecific antibodies (e.g., bispecific antibodies), and antibody fragments, so long as they exhibit the desired biological activity. Various techniques relevant to the production of antibodies are provided in, e.g., Harlow, et al., ANTIBODIES: A LABORATORY MANUAL, Cold Spring Harbor Laboratory Press, Cold Spring Harbor, N.Y., (1988).

An "antibody fragment" comprises a portion of a full-length antibody, preferably antigen-binding or variable regions thereof. Examples of antibody fragments include Fab, Fab', F(ab)$_2$, F(ab')$_2$, F(ab)$_3$, Fv (typically the VL and VH domains of a single arm of an antibody), single-chain Fv (scFv), dsFv, Fd fragments (typically the VH and CH1 domain), and dAb (typically a VH domain) fragments; VH, VL, VhH, and V-NAR domains; minibodies, diabodies, triabodies, tetrabodies, and kappa bodies (see, e.g., Ill et al., Protein Eng 1997; 10: 949-57); camel IgG; IgNAR; and multispecific antibody fragments formed from antibody fragments, and one or more isolated CDRs or a functional paratope, where isolated CDRs or antigen-binding residues or polypeptides can be associated or linked together so as to form a functional antibody fragment. Various types of antibody fragments have been described or reviewed in, e.g., Holliger and Hudson, Nat Biotechnol 2005; 23, 1126-1136; WO2005040219, and published U.S. Patent Applications 20050238646 and 20020161201.

The term "antibody derivative", as used herein, comprises a full-length antibody or a fragment of an antibody, preferably comprising at least antigen-binding or variable regions thereof, wherein one or more of the amino acids are chemically modified, e.g., by alkylation, PEGylation, acylation, ester formation or amide formation or the like. This includes, but is not limited to, PEGylated antibodies, cysteine-PEGylated antibodies, and variants thereof.

A "humanized" antibody is a human/non-human chimeric antibody that contains a minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit, or non-human primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, a humanized antibody will comprise substantially all of at least one, and typically two, variable domains, in which all or substantially all of the hypervariable loops correspond to those of a non-human immunoglobulin and all or substantially all of the FR residues are those of a human immunoglobulin sequence. The humanized antibody can optionally also comprise at least a portion of an immunoglobulin constant region (Fc), typically that of a human immunoglobulin.

The term "hypervariable region" when used herein refers to the amino acid residues of an antibody that are responsible for antigen binding. The hypervariable region generally comprises amino acid residues from a "complementarity-determining region" or "CDR" (e.g. residues 24-34 (L1), 50-56 (L2) and 89-97 (L3) in the light-chain variable domain and 31-35 (H1), 50-65 (H2) and 95-102 (H3) in the heavy-chain variable domain; Kabat et al. 1991) and/or those residues from a "hypervariable loop" (e.g. residues 26-32 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol 1987; 196:901-917). Typically, the numbering of amino acid residues in this region is performed by the method described in Kabat et al., supra. Phrases such as "Kabat position", "variable domain residue numbering as in Kabat" and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

By "framework" or "FR" residues as used herein is meant the region of an antibody variable domain exclusive of those regions defined as CDRs. Each antibody variable domain framework can be further subdivided into the contiguous regions separated by the CDRs (FR1, FR2, FR3 and FR4).

By "constant region" of an antibody as defined herein is meant the region of the antibody that is encoded by one of the light or heavy chain immunoglobulin constant region genes. By "constant light chain" or "light chain constant region" as used herein is meant the region of an antibody encoded by the kappa (Ckappa) or lambda (Clambda) light chains. The constant light chain typically comprises a single domain, and as defined herein refers to positions 108-214 of Ckappa, or Clambda, wherein numbering is according to the EU index (Kabat et al., 1991, Sequences of Proteins of Immunological Interest, 5th Ed., United States Public Health Service, National Institutes of Health, Bethesda). By "constant heavy chain" or "heavy chain constant region" as used herein is meant the region of an antibody encoded by the mu, delta, gamma, alpha, or epsilon genes to define the antibody's isotype as IgM, IgD, IgG, IgA, or IgE, respectively. For full length IgG antibodies, the constant heavy chain, as defined herein, refers to the N-terminus of the CH1 domain to the C-terminus of the CH3 domain, thus comprising positions 118-447, wherein numbering is according to the EU index.

By "Fab" or "Fab region" as used herein is meant the polypeptide that comprises the VH, CH1, VL, and CL immunoglobulin domains. Fab may refer to this region in isolation, or this region in the context of a full length antibody, antibody fragment or Fab fusion protein, or any other antibody embodiments as outlined herein.

By "Fv" or "Fv fragment" or "Fv region" as used herein is meant a polypeptide that comprises the VL and VH domains of a single antibody.

By "Fc" or "Fc region", as used herein is meant the polypeptide comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cγ2 and Cγ3 and the hinge between Cγ1 and Cγ2. Although the boundaries of the Fc region may vary, the human IgG heavy chain Fc region is usually defined to comprise residues C226, P230 or A231 to its carboxyl-terminus, wherein the numbering is according to the EU index. Fc may refer to this region in isolation, or this region in the context of an Fc polypeptide, as described below. By "Fc polypeptide" as used herein is meant a polypeptide that comprises all or part of an Fc region. Fc polypeptides include antibodies, Fc fusions, isolated Fcs, and Fc fragments.

By "full length antibody" as used herein is meant the structure that constitutes the natural biological form of an antibody, including variable and constant regions. For example, in most mammals, including humans and mice, the full length antibody of the IgG isotype is a tetramer and consists of two identical pairs of two immunoglobulin chains, each pair having one light and one heavy chain, each light chain comprising immunoglobulin domains VL and CL, and each heavy chain comprising immunoglobulin domains VH, Cγ1, Cγ2, and Cγ3. In some mammals, for example in camels and llamas, IgG antibodies may consist of only two heavy chains, each heavy chain comprising a variable domain attached to the Fc region.

By "variable region" as used herein is meant the region of an antibody that comprises one or more Ig domains substantially encoded by any of the VL (including Vkappa and Vlambda) and/or VH genes that make up the light chain (including kappa and lambda) and heavy chain immunoglobulin genetic loci respectively. A light or heavy chain variable region (VL and VH) consists of a "framework" or "FR" region interrupted by three hypervariable regions referred to as "complementarity determining regions" or "CDRs". The extent of the framework region and CDRs have been precisely defined, for example as in Kabat (see "Sequences of Proteins of Immunological Interest," E. Kabat et al., U.S. Department of Health and Human Services, (1983)), and as in Chothia. The framework regions of an antibody, that is the combined framework regions of the constituent light and heavy chains, serves to position and align the CDRs, which are primarily responsible for binding to an antigen.

By "amino acid modification" herein is meant an amino acid substitution, insertion, and/or deletion in a polypeptide sequence. The preferred amino acid modification herein is a substitution. By "amino acid modification" herein is meant an amino acid substitution, insertion, and/or deletion in a polypeptide sequence. By "amino acid substitution" or "substitution" herein is meant the replacement of an amino acid at a given position in a protein sequence with another amino acid. For example, the substitution Y50W refers to a variant of a parent polypeptide, in which the tyrosine at position 50 is replaced with tryptophan. A "variant" of a polypeptide refers to a polypeptide having an amino acid sequence that is substantially identical to a reference polypeptide, typically a native or "parent" polypeptide. The polypeptide variant may possess one or more amino acid substitutions, deletions, and/or insertions at certain positions within the native amino acid sequence.

"Conservative" amino acid substitutions are those in which an amino acid residue is replaced with an amino acid residue having a side chain with similar physicochemical properties. Families of amino acid residues having similar side chains are known in the art, and include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

An "isolated" molecule is a molecule that is the predominant species in the composition wherein it is found with respect to the class of molecules to which it belongs (i.e., it makes up at least about 50% of the type of molecule in the composition and typically will make up at least about 70%, at least about 80%, at least about 85%, at least about 90%, at least about 95%, or more of the species of molecule, e.g., peptide, in the composition). Commonly, a composition of an antibody molecule will exhibit 98%, 98%, or 99% homogeneity for antibody molecules in the context of all present peptide species in the composition or at least with respect to substantially active peptide species in the context of proposed use.

The term "reactive moiety" herein refers to a moiety that can be coupled with another moiety without prior activation or transformation.

The term "protecting group" refers to a group that temporarily protects or blocks, i e., intended to prevent from reacting, a functional group, e.g, an amino group, a hydroxyl group, or a carboxyl group, during the transformation of a first molecule to a second molecule.

The phrase "moiety that improves the pharmacokinetic properties", when referring to a compound (e.g. an antibody) refers to a moiety that changes the pharmacokinetic properties of the one or more moieties Z in such a way that a better therapeutic or diagnostic effect can be obtained. The moiety can for example increase the water solubility, increase the circulation time, or reduce immunogenicity.

The phrase "linking group" refers to a structural element of a compound that links one structural element of said compound to one or more other structural elements of said same compound.

The phrase "a number representing degree of branching" is used to denote that the subscript number next to a closing bracket represents how many units of the moiety within the brackets are attached to the moiety directly to the left of the corresponding opening bracket. For example, $A\text{-}(B)_b$ with b being a number representing a degree of branching means that b units B are all directly attached to A This means that when b is 2, the formula reduces to B-A-B.

The phrase "a number representing degree of polymerization" is used to denote that the subscript number next to a closing bracket represents how many units of the moiety within the brackets are connected to each other. For example, $A\text{-}(B)_1$, with b being a number representing a degree of polymerization means that when b is 2, the formula reduces to A-B-B.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

As used herein, "alkyl" refers to a straight or branched hydrocarbon chain that comprises a fully saturated (no double or triple bonds) hydrocarbon group. The alkyl group may have, for example, 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, the term "heteroalkyl" refers to a straight or branched alkyl group that contains one or more heteroatoms, that is, an element other than carbon (including but not limited to oxygen, sulfur, nitrogen, phosphorus) in place of one or more carbon atoms.

Whenever a group is described as being "substituted" that group substituted with one or more of the indicated substituents. If no substituents are indicated, it is meant that the indicated "substituted" group may be substituted with one or more group(s) individually and independently selected from alkyl, alkenyl, alkynyl, cycloalkyl, cycloalkenyl, cycloalkynyl, heteroalkyl, aryl, heteroaryl, heteroalicyclyl, aralkyl, heteroaralkyl, (heteroalicyclyl)alkyl, hydroxy, alkoxy, aryloxy, acyl, mercapto, alkylthio, arylthio, cyano, halogen, thiocarbonyl, carbamyl, thiocarbamyl, amido, sulfonamido, sulfonamido, carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, and protected derivatives thereof.

Where the number of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

Producing Antibodies

Antibodies may be produced by a variety of techniques known in the art. Typically, they are produced by immunization of a non-human animal, preferably a mouse, with an immunogen comprising a polypeptide, or a fragment or derivative thereof, typically an immunogenic fragment, for which it is desired to obtain antibodies (e.g. a human polypeptide). The step of immunizing a non-human mammal with an antigen may be carried out in any manner well known in the art for stimulating the production of antibodies in a mouse (see, for example, E. Harlow and D. Lane, Antibodies: A Laboratory Manual, Cold Spring Harbor Laboratory Press, Cold Spring Harbor, N.Y. (1988), the entire disclosure of which is herein incorporated by reference). Other protocols may also be used as long as they result in the production of B cells expressing an antibody directed to the antigen used in immunization. Lymphocytes from a non-immunized non-human mammal may also be isolated, grown in vitro, and then exposed to the immunogen in cell culture. The lymphocytes are then harvested and the fusion step described below is carried out. For preferred monoclonal antibodies, the next step is the isolation of splenocytes from the immunized non-human mammal and the subsequent fusion of those splenocytes with an immortalized cell in order to form an antibody-producing hybridoma. The hybridoma colonies are then assayed for the production of antibodies that specifically bind to the polypeptide against which antibodies are desired. The assay is typically a colorimetric ELISA-type assay, although any assay may be employed that can be adapted to the wells that the hybridomas are grown in. Other assays include radioimmunoassays or fluorescence activated cell sorting. The wells positive for the desired antibody production are examined to determine if one or more distinct colonies are present. If more than one colony is present, the cells may be re-cloned and grown to ensure that only a single cell has given rise to the colony producing the desired antibody. After sufficient growth to produce the desired monoclonal antibody, the growth media containing monoclonal antibody (or the ascites fluid) is separated away from the cells and the monoclonal antibody present therein is purified. Purification is typically achieved by gel electrophoresis, dialysis, chromatography using protein A or protein G-Sepharose, or an anti-mouse Ig linked to a solid support such as agarose or Sepharose beads (all described, for example, in the Antibody Purification Handbook, Biosciences, publication No. 18-1037-46, Edition AC, the disclosure of which is hereby incorporated by reference).

Additionally, a wide range of antibodies are available in the scientific and patent literature, including DNA and/or amino acid sequences, or from commercial suppliers. Examples of antibodies include antibodies that recognize an antigen expressed by a target cell that is to be eliminated, for example a proliferating cell or a cell contributing to a pathology. Examples include antibodies that recognize tumor antigens, microbial (e.g. bacterial) antigens or viral antigens. Other examples include antigens present on immune cells that are contributing to inflammatory or autoimmune disease, including rejection of transplanted tissue (e.g. antigens present on T cells (CD4 or CD8 T cells).

Antibodies will typically be directed to a pre-determined antigen. As used herein, the term "bacterial antigen" includes, but is not limited to, intact, attenuated or killed bacteria, any structural or functional bacterial protein or carbohydrate, or any peptide portion of a bacterial protein of sufficient length (typically about 8 amino acids or longer) to be antigenic. Examples include gram-positive bacterial antigens and gram-negative bacterial antigens. The bacterial antigen may be derived from a bacterium selected from the group consisting of *Helicobacter* species, in particular *Helicobacter pyloris*; *Borelia* species, in particular *Borelia burgdorferi*; *Legionella* species, in particular *Legionella pneumophilia*; *Mycobacterias* species, in particular *M. tuberculosis, M. avium, M. intracellulare, M. kansasii, M. gordonae*; *Staphylococcus* species, in particular *Staphylococcus aureus*; *Neisseria* species, in particular *N. gonorrhoeae, N. meningitidis*; *Listeria* species, in particular *List-* eria monocytogenes; Streptococcus species, in particular S. pyogenes, S. agalactiae; S. faecalis; S. bovis, S. pneumonias; anaerobic Streptococcus species; pathogenic Campylobacter species; Enterococcus species; Haemophilus species, in particular Haemophilus influenzue; Bacillus species, in particular Bacillus anthracis; Corynebacterium species, in particular Corynebacterium diphtheriae; Erysipelothrix species, in particular Erysipelothrix rhusiopathiae; Clostridium species, in particular C. perfringens, C. tetani; Enterobacter species, in particular Enterobacter aerogenes, Klebsiella species, in particular Klebsiella 1S pneumoniae, Pasturella species, in particular Pasturella multocida, Bacteroides species; Fusobacterium species, in particular Fusobacterium nucleatum; Streptobacillus species, in particular Streptobacillus moniliformis; Treponema species, in particular Treponema pertenue; Leptospira; pathogenic Escherichia species; and Actinomyces species, in particular Actinomyces israelli.

As used herein, the term "viral antigen" includes, but is not limited to, intact, attenuated or killed whole virus, any structural or functional viral protein, or any peptide portion of a viral protein of sufficient length (typically about 8 amino acids or longer) to be antigenic. Sources of a viral antigen include, but are not limited to viruses from the families: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bunyaviridae (e.g., Hantaan viruses, bunya viruses, phleboviruses and Nairo viruses); Arenaviridae (hemorrhagic fever viruses); Reoviridae (e.g., reoviruses, orbiviruses and rotaviruses); Bornaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g., African swine fever virus); and unclassified viruses (e.g., the agent of delta hepatitis (thought to be a defective satellite of hepatitis B virus), Hepatitis C; Norwalk and related viruses, and astroviruses). Alternatively, a viral antigen may be produced recombinantly.

As used herein, the terms "cancer antigen" and "tumor antigen" are used interchangeably and refer to antigens that are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal trans- locations. Still other cancer antigens can be encoded by viral genes such as those carried on RNA and DNA tumor viruses.

The cancer antigens are usually normal cell surface antigens which are either over-expressed or expressed at abnormal times. Ideally the target antigen is expressed only on proliferative cells (preferably tumour cells), however this is rarely observed in practice. As a result, target antigens are usually selected on the basis of differential expression between proliferative and healthy tissue. Antibodies have been raised to target specific tumour related antigens including: Cripto, CD4, CD20, CD30, CD19, CD33, Glycoprotein NMB, CanAg, Her2 (ErbB2/Neu), CD56 (NCAM), CD22 (Siglec2), CD33 (Siglec3), CD79, CD138, CD171, PSCA, PSMA (prostate specific membrane antigen), BCMA, CD52, CD56, CD80, CD70, E-selectin, EphB2, Melanotransferin, Mud 6 and TMEFF2. Examples of cancer antigens also include B7-H3, B7-H4, B7-H6, PD-L1, MAGE, MART-1/Melan-A, gp100, adenosine deaminase-binding protein (ADAbp), cyclophilin b, colorectal associated antigen (CRC)-C017-1A/GA733, carcinoembryonic antigen (CEA) and its immunogenic epitopes CAP-1 and CAP-2, etv6, aml1, prostate specific antigen (PSA), T-cell receptor/CD3-zeta chain, MAGE-family of tumor antigens, GAGE-family of tumor antigens, BAGE, RAGE, LAGE-1, NAG, GnT-V, MUM-1, CDK4, MUC family, VEGF, VEGF receptors, PDGF, TGF-alpha, EGF, EGF receptor, a member of the human EGF-like receptor family such as HER-2/neu, HER-3, HER-4 or a heterodimeric receptor comprised of at least one HER subunit, gastrin releasing peptide receptor antigen, Muc-1, CA125, αvß3 integrins, α5ß1 integrins, αIIbß3-integrins, PDGF beta receptor, SVE-cadherin, IL-8, hCG, IL-6, IL-6 receptor, IL-15, α-fetoprotein, E-cadherin, α-catenin, ß-catenin and γ-catenin, p120ctn, PRAME, NY-ESO-1, cdc27, adenomatous polyposis coli protein (APC), fodrin, Connexin 37, Ig-idiotype, p15, gp75, GM2 and GD2 gangliosides, viral products such as human papillomavirus proteins, imp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, and c-erbB-2, although this is not intended to be exhaustive.

Human antibodies may also be produced by using, for immunization, transgenic animals that have been engineered to express a human antibody repertoire (Jakobovitz et Nature 362 (1993) 255), or by selection of antibody repertoires using phage display methods. For example, a Xeno-Mouse (Abgenix, Fremont, Calif.) can be used for immunization. A XenoMouse is a murine host that has had its immunoglobulin genes replaced by functional human immunoglobulin genes. Thus, antibodies produced by this mouse or in hybridomas made from the B cells of this mouse, are already humanized. The XenoMouse is described in U.S. Pat. No. 6,162,963, which is herein incorporated in its entirety by reference.

In one aspect of any of the embodiments herein, the antibodies or antibody samples are provided for TGase-mediated coupling in the form of unpurified hybridoma supernatant. Optionally, the hybridoma supernatant comprises unquantified antibody produced from a plurality of hybridoma clones, wherein the plurality of samples vary with respect to antibody quantity and antibody sequence provided that, in a majority of the plurality of the samples, substantially all of the antibody present in each sample is from a single hybridoma clone.

It will be appreciated that antibodies can also be provided in purified and/or modified form following immunization and identification or cells producing an antibody of interest. DNA encoding an antibody of interest can be placed in an appropriate expression vector for transfection into an appropriate host. The host is then used for the recombinant production of the antibody, or variants thereof, such as a humanized version of that monoclonal antibody, active fragments of the antibody, chimeric antibodies comprising the antigen recognition portion of the antibody, or versions comprising a detectable moiety.

In certain embodiments, the DNA of a hybridoma or other cell producing an antibody can be modified prior to insertion into an expression vector, for example, by substituting the coding sequence for human heavy- and light-chain constant domains in place of the homologous non-human sequences (e.g., Morrison et al., PNAS pp. 6851 (1984)), or by covalently joining to the immunoglobulin coding sequence all or part of the coding sequence for a non-immunoglobulin polypeptide. In that manner, "chimeric" or "hybrid" antibodies are prepared that have the binding specificity of the original antibody. Typically, such non-immunoglobulin polypeptides are substituted for the constant domains of an antibody.

Humanized antibodies are typically specific chimeric immunoglobulins, immunoglobulin chains or fragments thereof (such as Fv, Fab, Fab', F (ab') 2, "dab", or other antigen-binding subsequences of antibodies) which contain minimal sequence derived from the murine immunoglobulin. For the most part, humanized antibodies are human immunoglobulins (recipient antibody) in which residues from a complementary-determining region (CDR) of the recipient are replaced by residues from a CDR of the original antibody (the parent or donor antibody) while maintaining the desired specificity, affinity, and capacity of the original antibody. The CDRs of the parent antibody, some or all of which are encoded by nucleic acids originating in a non-human organism, are grafted in whole or in part into the beta-sheet framework of a human antibody variable region to create an antibody, the specificity of which is determined by the engrafted CDRs. The creation of such antibodies is described in, e.g., WO 92/11018, Jones, 1986, Nature 321: 522-525, Verhoeyen et al., 1988, Science 239:1534-1536.

Wild-type full-length IgG antibodies of human isotype will possess a conserved acceptor glutamine at residue 295 of the heavy chain which when in non-glycosylated form will be accessible to a TGase and therefore reactive with a compound of Formula I in the presence of a TGase, under suitable conditions, to form a conjugate from the antibody and the compound of Formula II. The antibody will lack glycosylation at the asparagine at residue 297 of the heavy chain.

In one embodiment, the antibodies or antibody samples that are provided comprise a constant region and/or Fc region of human origin, optionally a human IgG1, IgG2, IgG3 or IgG4 isotype. Optionally the antibodies or antibody samples that are provided comprise a more than one human IgG1, IgG2, IgG3 or IgG4 isotype, i.e. antibody samples are of different isotypes. In one embodiment, the antibodies or antibody samples comprise a wild-type (naturally occurring) human heavy and/or light chain constant region sequence (representing a full-length human constant region or a fragment thereof, e.g. a contiguous sequence of at least 20, 50, 60, 75 or 100 amino acid residues of a human constant region). Preferably the antibodies or antibody samples comprise a human heavy and/or light chain constant region (e.g. a full-length heavy and/or light chain human constant region) that is at least 95, 98, or 99% identical to a naturally occurring human constant region sequence. Optionally the constant region further comprises one or more (e.g. 2, 3, 4, 5 or more) amino acid substitution(s), optionally wherein said substitution(s) is the replacement of an amino acid residue by a glutamine. Optionally, the wild-type constant region sequence comprises one or more single amino acid substitutions. Optionally, the wild-type constant region sequence comprises one or more amino acid substitutions, wherein all the substitutions are naturally occurring amino acids. Preferably the wild-type constant region sequence is free of an enzymatic recognition tag, i.e. a sequence of 2, 3, 4, 5 or more residues specifically recognized by an enzyme, for example an enzyme that conjugates a moiety of interest to an antibody, a formylglycine-generating enzyme, a sortase, etc.

While it will be advantageous to screen antibodies directly without modification, additional or alternative sites reactive with a compound of Formula I in the presence of a TGase can optionally be created by engineering the antibodies, for example to explore and compare efficacy where more than one glutamine is conjugated on each heavy chain. The compounds include glutamine engineered antibodies where one or more amino acids of a wild-type or parent antibody are replaced with (substituted by) a glutamine amino acid, or where a glutamine residue, optionally together with other amino acid residues, is introduced or added to a wild-type or parent antibody (e.g. wherein the glutamine residue is added to an antibody fragment).

It should be noted that a single site mutation that provides a glutamine that is accessible to a TGase may yield more than one engineered glutamine residue that can be conjugated if the antibody comprises more than one engineered chain. For example, a single site mutation will yield two engineered glutamine residues in a tetrameric IgG due to the dimeric nature of the IgG antibody. The engineered glutamine residues will be in addition to any acceptor glutamine already present in an antibody, if any. The glutamine amino acid residues that are reactive, in the presence of a TGase under suitable conditions, with a compound of Formula I may be located in the heavy chain, typically in the constant domain.

In one embodiment, the asparagine at amino acid position 297 (EU Index of Kabat (1991)) of a human heavy chain constant region is substituted with a glutamine or other non-asparagine residue. The antibody will have a constant region with a N297Q substitution (a N297Q variant antibody). An antibody having a N297Q substitution and a glutamine at residue 295 (EU Index of Kabat (1991)) will therefore have two acceptor glutamines and thus two conjugation sites per heavy chain. In tetrameric form will therefore have four conjugates per antibody. An antibody with a non-asparagine residue will have one conjugation sites per heavy chain, and two conjugates per full length tetrameric antibody.

Such antibody will also have the advantage that no enzymatic deglycosylation step is needed prior to reaction with TGase since such antibody will naturally lack glycosylation.

Glutamine engineered antibodies can be prepared by a variety of methods which include, but are not limited to, isolation from a natural source (in the case of naturally occurring amino acid sequence variants), preparation by site-directed (or oligonucleotide-mediated) mutagenesis (Carter (1985) et al Nucleic Acids Res. 13:4431-4443; Kunkel et al (1987) Proc. Natl. Acad. Sci. USA 82:488; Liu et al (1998) J. Biol. Chem. 273:20252-20260), PCR mutagenesis (Higuchi, (1990) in PCR Protocols, pp. 177-183, Academic Press; Ito et al (1991) Gene 102:67-70; Bernhard et al (1994) Bioconjugate Chem. 5: 126-132; and Vallette et al (1989) Nuc. Acids Res. 17:723-733) and cassette mutagenesis (Wells et al (1985) Gene 34:315-323) of an earlier prepared DNA encoding the polypeptide. Mutagenesis protocols, kits, and reagents are commercially available, e.g. QuikChange® Multi Site-Direct Mutagenesis Kit (Stratagene, La Jolla, Calif.). Single mutations are also generated by oligonucleotide directed mutagenesis using double stranded plasmid DNA as template by PCR based mutagenesis (Sambrook and Russel, (2001) Molecular Cloning: A Laboratory Manual, 3rd edition; Zoller et al (1983) Methods Enzymol. 100:468-500; ZoDer, M J. and Smith, M. (1982) Nucl. Acids Res. 10:6487-6500). Variants of recombinant antibodies may be constructed also by restriction fragment manipulation or by overlap extension PCR with synthetic oligonucleotides. Mutagenic primers encode the cysteine codon replacement(s). Standard mutagenesis techniques can be employed to generate DNA encoding such mutant cysteine engineered antibodies (Sambrook et al Molecular Cloning, A Laboratory Manual. Cold Spring Harbor Laboratory Press, Cold Spring Harbor, N.Y., 1989; and Ausubel et al Current Protocols in Molecular Biology, Greene Publishing and Wiley-Interscience, New York. N.Y., 1993).

Antibodies may be chemically synthesized using known oligopeptide synthesis methodology or may be prepared and purified using recombinant technology. In vitro protein synthesis may be performed using manual techniques or by automation.

Fragments and derivatives of antibodies (which are encompassed by the term "antibody" or "antibodies" as used in this application, unless otherwise stated or clearly contradicted by context), can be produced by techniques that are known in the art. "Fragments" comprise a portion of the intact antibody, generally the antigen binding site or variable region. Examples of antibody fragments include Fab, Fab', Fab'-SH, F(ab')2, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific antibodies formed from antibody fragments. Included, inter alia, are a nanobody, domain antibody, single domain antibody or a "dAb".

The DNA of a hybridoma producing an antibody may be modified so as to encode a fragment. The modified DNA is then inserted into an expression vector and used to transform or transfect an appropriate cell, which then expresses the desired fragment.

The fragment will comprise a variable region domain that will generally be covalently attached to at least one, two or more glutamine residue covalently linked through a —NH—$(C)_n$—X-L moiety (and optionally further a V and/or Y moiety, optionally further an R or RR' moiety, to a moiety-of-interest Z, e.g. a polymer molecule, a drug, a radioactive moiety. The variable region will comprise hypervariable region or CDR sequences, and FR sequences.

The location of the glutamine residue may be varied according to the size and nature of the antibody fragment required. Thus, in one extreme example an acceptor glutamine residue to be conjugated to a lysine-based linker of Formula I may be attached directly to a C-terminal amino acid of the variable region domain. This may be for example the C-terminus of a VH or VL chain as described above. If desired, in this example, further amino acids, including further acceptor glutamine residues, may be covalently linked to the C-terminus of the first glutamine residue. In one example, a peptide "tag" comprising one or more non-glutamine residues followed by an acceptor glutamine residue (the acceptor glutamine residue is C-terminal to the non-glutamine residue in the tag) is attached directly to a C-terminal amino acid of the variable region domain. In one example, a peptide "tag" comprising one or more glutamine residues followed by one or more non-glutamine residues (the non-glutamine residues are C-terminal to the glutamine residue in the tag) is attached directly to a C-terminal amino acid of the variable region domain. A peptide tag can be of any suitable length, e.g a tag may comprise between 2 and 50, preferably 2 and 20 or 2 and 10 amino acid residues.

In practice however, it is generally preferable that the variable region domain is covalently attached at a C-terminal amino acid to at least one other antibody domain or a fragment thereof which contains, or is attached to one or more acceptor glutamine residues. Thus, for example where a VH domain is present in the variable region domain this may be linked to an immunoglobulin CH1 domain or a fragment thereof. Similarly a VL domain may be linked to a CK domain or a fragment thereof. In this way for example the fragment according may be a Fab fragment wherein the antigen binding domain contains associated VH and VL domains covalently linked at their C-termini to a CH1 and CK domain respectively. The CH1 domain may be extended with further amino acids, for example to provide a hinge region domain as found in a Fab' fragment, or to provide further domains, such as antibody CH2 and CH3 domains. In one example, a polypeptide "tag" comprising one or a plurality (e.g. 2, 3, 4, 5, 6) non-glutamine residues followed by a glutamine residue (the glutamine residue is C-terminal to the non-glutamine residue in the tag) is attached directly to a C-terminal amino acid of a full or truncated CH1, CH2 or CH3 domain, or to a C-terminal amino acid of a full or truncated CK domain. In one example, a polypeptide "tag" comprising one or more glutamine residues followed by one or more non-glutamine residues (the non-glutamine residues are C-terminal to the glutamine residue in the tag) is attached directly to a C-terminal amino acid of a full or truncated CH1, CH2 or CH3 domain, or to a C-terminal amino acid of a full or truncated CK domain.

An antibody fragment may have a monomeric variable region domain and comprise an immunoglobulin heavy (VH) or light (VL) chain variable domain, or is dimeric and contains VH-VH, VH-VL or VL-VL dimers in which the VH and VL chains are non-covalently associated or covalently coupled, wherein the fragment (i.e. the VL and/or VH) is covalently linked through a —NH—$(C)_n$—X-L moiety (and optionally further a V and/or Y moiety, optionally further L', V', Y', and (RR')moieties, to a moiety-of-interest Z, e.g. a polymer molecule, a drug, a radioactive moiety. Preferably each VH and/or VL domain is covalently attached at a C-terminal amino acid to at least one other antibody domain or a fragment thereof.

In one embodiment, a monovalent antibody fragment comprises a heavy chain and a light chain, wherein: said heavy chain consists of a VH domain covalently linked at its C-terminus to a CH1 domain; said light chain consists of a VL domain, which is complementary to the VH domain, covalently linked at its C-terminus to a CL domain; said CH1 domain comprises (e.g., the CH1 is extended) to provide a hinge domain which comprises a glutamine residue; and the glutamine residue in the hinge domain is covalently linked through a —NH—(C)$_n$—X-L moiety. In another embodiment, a monovalent antibody fragment comprises a heavy chain and a light chain, wherein: said heavy chain consists of a VH domain covalently linked at its C-terminus to a CH1 domain; said light chain consists of a VL domain, which is complementary to the VH domain, covalently linked at its C-terminus to a CL domain; said CL domain comprises (e.g., the CL is extended) to provide a hinge domain which comprises a glutamine residue; and the glutamine residue in the hinge domain is covalently linked through a —NH—(C)$_n$—X-L moiety.

In one embodiment, the antibody fragment is linked through a —NH—(C)$_n$—X-L moiety to a polymer (e.g. a PEG-comprising molecule).

A plurality of antibody-containing samples are thus provided thus and can then be conjugated to a moiety of interest (Z) and screened for a characteristic of interest. The phrase "a plurality of samples" refers to two or more samples. Because the methods provided herein are ideally suited for high throughput screening, in one aspect, the methods are performed simultaneously on at least tens or at least hundreds of samples. One of the strengths of the methods provided herein is that conjugation will be limited to acceptor glutamines in constant regions which can be readily defined, either because antibodies naturally contain a defined number of sites (e.g. one site per heavy chain in all antibodies of human isotype) or because antibodies are provided in a format where antibodies are engineered to contain the desired number of sites. In one aspect, the samples vary with respect to antibody quantity and with respect to antibody sequence. For example, in one aspect, a first sample will comprise a first antibody at a first quantity and a second sample will comprise a second antibody at a second quantity. The first and second quantities will vary and the first and second antibodies will vary. In embodiments wherein it is desirable to compare antibodies that target the same antigen, the antibodies will immunospecifically bind to the same antigen. For purpose of clarification, the phrase "wherein the plurality of samples vary with respect to antibody quantity and antibody sequence" does not require that all of the samples within a plurality of samples vary with respect to antibody quantity and antibody sequence, only that there is certain level of heterogeneity between samples. Although there is a variance in antibody sequence (e.g., a first sample will contain a different antibody than a second sample), it is preferable that a single sample contain one antibody, i.e., that the antibody present in a single sample is of the same sequence. The phrase "substantially all of the antibody present in a single sample is of the same sequence" reflects the preference that a single sample contain one antibody with the recognition that, in some samples, there may be some contamination with another antibody. Preferably, in those samples that have some contamination with another antibody, there is less than 30%, preferably less than 20%, preferably less than 15%, more preferably less than 10%, and even more preferably less than 5%, less than 4%, or less than 3% of contamination with another antibody. In preferred embodiments, the majority of antibody-containing samples (greater that 50% of samples and even more preferably greater than 60%, greater than 70%, greater than 75%, or even greater than 80% of the samples) in a plurality of antibody-containing samples contain one antibody with no or minor amounts of contamination with another antibody (e.g., less than 15%, preferably even less than 10% or less than 5% contamination with another antibody). In some preferred embodiments, a majority of the antibody-containing samples will comprise antibodies that immunospecifically bind to the same antigen.

Lysine-Based Linkers

The antibodies and antibody samples will be conjugated to a moiety-of-interest via a linking reagent that can be attached, by the action of a TGase, at an acceptor glutamine residue (Q) within the sequence of the antibody (Ab). The antibodies in the antibody samples will typically be conjugated to a moiety of interest (Z) such as a drug or diagnostic compound, however the antibodies may also be retained as intermediates which are conjugated to a reactive group (R), preferably a protected reactive group. Such antibodies can be used for further reactions subsequently. Thus, the linking reagent used will depend on the particular screening strategy used.

In one embodiment the linking reagent comprises a lysine derivative (Lys), or a functional equivalent thereof, that is connected to at least one moiety of interest (Z). In another embodiment, a two-step (or multi-step) strategy is used to attach moieties of interest in a stoichiometric fashion, in which the linking reagent comprises a lysine derivative (Lys), or a functional equivalent thereof, that is connected to a reactive group (R). In one embodiment, a plurality of reactive groups, preferably non-complementary reactive groups, can be attached to the linking reagent. The reactive group is preferably a functionality that is insensitive to water but selectively undergoes a very high conversion addition reaction with a complementary reagent.

The functional equivalent of a lysine derivative comprises a 2 to 20 carbon chain, or a functional equivalent thereof, with an aminomethylene ($H_2NCH_2$) group or a protected $H_2NCH_2$ group that can be derived from the aminomethylene positioned at one or more ends of the carbon chain. The functional equivalent of the carbon chain is a chain of 3 to 20 atoms where one or more non-terminal atoms can be other than carbon, for example oxygen, sulfur, nitrogen, or other atoms. The oxygen, sulfur, or nitrogen atom can be of an ether, ester, thioether, thioester, amino, alkylamino, amido or alkylamido functionality within the carbon chain.

One exemplary functional equivalent of the carbon chain is an oligo (ethylene oxide) chain. The functionality within the carbon chain can be included to couple the reactive group to the $H_2NCH_2$ group or protected $H_2NCH_2$ group. The carbon chain, or its functional equivalent, can be substituted or unsubstituted. The substituents can be alkyl groups, aryl groups, alkyl aryl groups, carboxylic acid groups, amide groups, hydroxy groups, or any other groups that do not compete with the amino group for, or inhibit, conjugation with a glutamine residue of the protein. Typically, when a substituent is present, its presence is in a convenient starting material, such as the carboxylic acid group of lysine, from which the lysine derivative results. The aminomethylene end of a carbon chain is necessarily included in the linking reagent.

Starting materials for the functional equivalent of lysine can be an α,ω-diaminoalkane, for example, 1,2-diaminoethane, 1,3-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, 1,11-diaminoundecane, or 1,12-diaminododecane. Other starting materials for the functional equivalent of a lysine derivative can be α,ω-diamino oligo (ethylene oxide), for example, $H_2N(CH_2CH_2O)_xCH_2CH_2NH_2$ where x is 1 to about 6. The α,ω-diamino oligo (ethylene oxide) can be a single oligomer or it can be a mixture of oligomers where x defines an average size. An exemplary protected $H_2NCH_2$ is the tert-butylcarbamate protected amine of tert-butyl N-(5-aminopentyl)carbamate (N-Boc-cadaverine).

The linking reagent comprising an R group for use in a multi-step method, a pharmaceutically acceptable salt or solvate thereof, or a protein conjugated linking reagent can have the general Formula Ia or Ib.

Formula Ia (having an R group) is shown below:

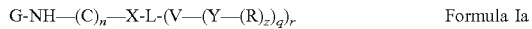

Formula Ia where: G is an H, amine protecting group, or upon conjugation, an immunoglobulin (Ab) or other protein attached via an amide bond;

$(C)_n$ is a substituted or unsubstituted alkyl or heteroalkyl chain, optionally wherein any carbon of the chain is substituted with an alkoxy, hydroxyl, alkylcarbonyloxy, alkyl-S—, thiol, alkyl-C(O)S—, amine, alkylamine, amide, or alkylamide; n, the length of the carbon chain, is an integer selected from among the range of 2- to 20, preferably 3 to 6 (e.g. a linear carbon chain of 2 to 20 atoms, preferably 3 to 6 atoms);

X is NH, O, S, or absent;

L is independently absent, a bond or a continuation of a bond, or a carbon comprising framework of 5 to 200 atoms substituted at one or more atoms, optionally, wherein the carbon comprising framework comprises a linear framework of 5 to 30 carbon atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

r is an integer selected from among 1, 2, 3 or 4;
q is an integer selected from among 1, 2, 3 or 4; and
z is an integer selected from among 1, 2, 3 or 4;

V is independently absent, being a bond or a continuation of a bond if L is a bond, a non-cleavable moiety or a conditionally-cleavable moiety, optionally following prior conditional transformation, which can be cleaved or transformed by a chemical, photochemical, physical, biological, or enzymatic process (e.g. cleavage of V ultimately leading to release of one or more moieties subsequently or ultimately linked to V, for example a Z moiety). In some embodiments, V is, preferably, a di-, tri-, tetra-, or oligo-peptide as described below in the section entitled "The V Moiety";

Y is independently absent, being a bond or a continuation of a bond if V is a bond or continuation of a bond, or a spacer system (e.g., a self-eliminating spacer system or a non-self-elimination spacer system) which is comprised of 1 or more spacers; and R is a reactive moiety, preferably a moiety comprising an unprotected or protected thiol, maleimide, a halo-acetamide, a halo-acetamide (e.g. bromo-acetamide, iodo-acetamide, cloro-acetamide), o-phoshenearomatic ester, azide, fulminate, alkyne, cyanide, anthracene, 1,2,4,5-tetrazine, norbornene, other stained or otherwise electronically activated alkene or, optionally, a protected or unprotected amine when X is absent and L, V, or Y is other than a bond or a continuation of a bond. In an alternative embodiment R is a reactive moiety, preferably a moiety comprising an unprotected or protected thiol, an unprotected or protected amine, maleimide, halo-acetamide, o-phoshenearomatic ester, azide, fulminate, alkyne, cyanide, anthracene, 1,2,4,5-tetrazine, norbornene, other stained or otherwise electronically activated alkene. Optionally, R is not an amine when n=5 and X, L, V and Y are absent. Optionally, R is not an amine when n=4 and X, L, V and Y are absent.

When more than one R group is present in a compound of the formula, the R groups will preferably be compatible such that no R group is a complementary reagent to any other R group. The L group can be a carbon comprising framework, where L is a linear hydrocarbon, a symmetrically or asymmetrically branched hydrocarbon, monosaccharide, disaccharide, linear or branched oligosaccharide (asymmetrically branched or symmetrically branched), other natural oligomer, dimer, trimer, or higher oligomer (linear asymmetrically branched or symmetrically branched) resulting from any chain-growth or step-growth polymerization process, wherein L has r, q, and/or z sites of attachment for the respective V, Y, and R groups, where r and q represent the degree of branching or polymerization. The sites of attachment can comprise a bond or comprise a functional group selected from an alkene, alkyne, ether, thioether, ester, thioester, amine, amide, alkylamide, or other functional group readily generated by a condensation or addition reaction.

The linkers of Formula Ia can be reacted with an antibody, in the presence of a TGase, to produce an antibody of Formula II.

In Formula I and II, the linking group L links the aminopeptidyl moiety $-NH-(C)_n-X$ to the reactive group R, optionally through one or more V and/or Y moieties where present. L may be a bond connecting V, Y or R directly to the aminopeptidyl moiety. In another aspect, however, L is a linking group that functionally links or spaces the one or more moieties V and/or Y reactive moiety R. In Formula I and II, spacing may make the reactive moiety R more accessible to the reaction partner, for example when the reactive moiety is present on a lysine-based linker and coupled to the antibody and then brought into contact with a reaction partner. In antibodies comprising a functionalized acceptor glutamine of Formula IV spacing may provide for a better accessibility of V, which in the case of enzymatic cleavage or transformation of V, may improve the rate at which V is transformed and/or cleaved.

The compound of Formula Ia can optionally be reacted with a reaction partner (e.g a compound of Formula III) to create pre-assembled linker intermediates. A functionalized lysine-based linker that can be conjugated to an antibody can thus also have the structure of Formula Ib:

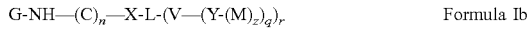

Figure 2:
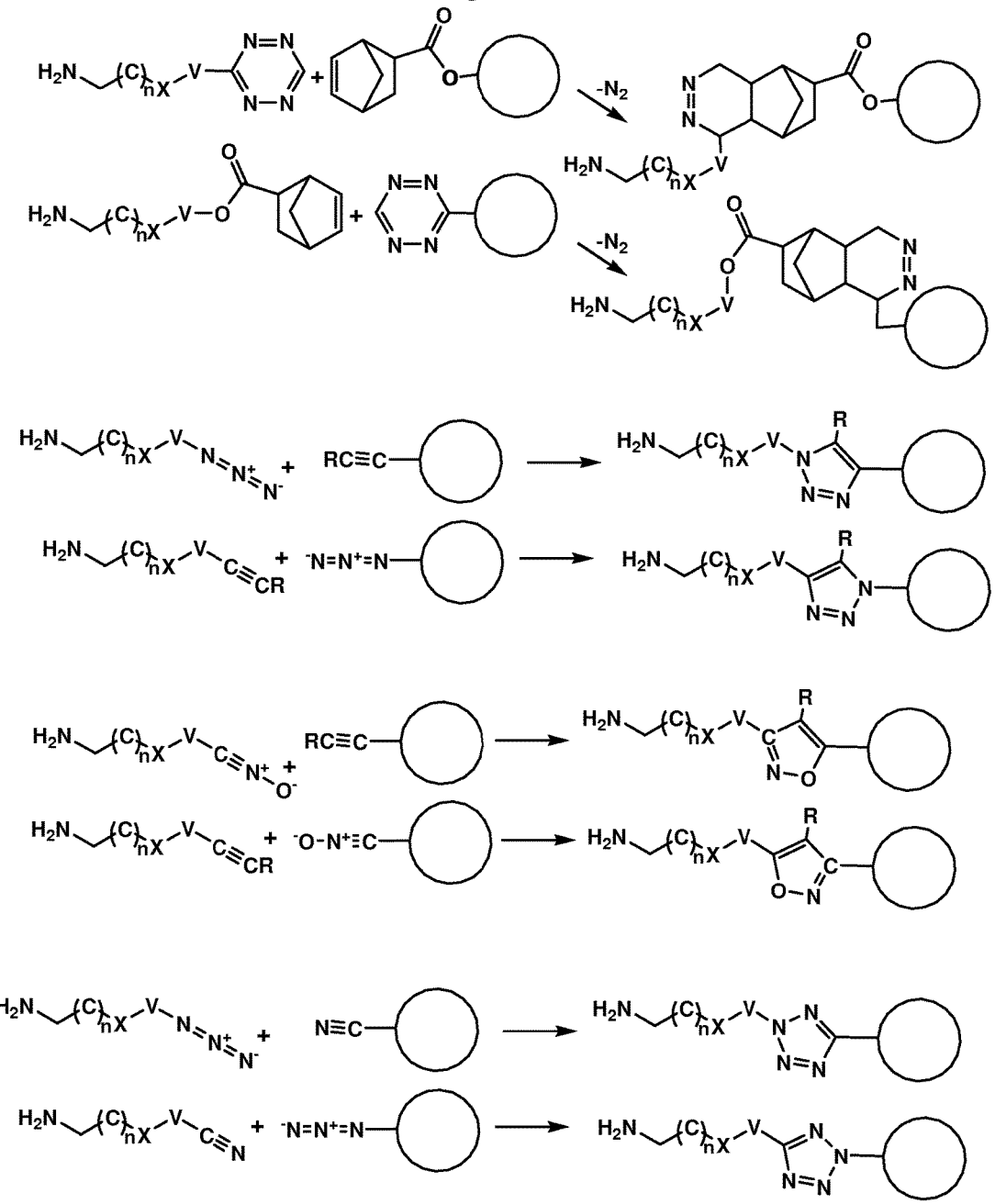
FIG. 2 shows reaction schemes for Diels-Alder cycloadditions and click reactions where the reactive groups of linking reagents combine with complementary reactive group attached to an agent including a therapeutic, diagnostic, or other moiety.

Formula Ib wherein each of G, C, n, X, L, V, Y, z, q, and r are as defined in Formula Ia, and M is independently: R or (RR')-L'-(V'—(Y'—(Z)$_{z'}$)$_{q'}$)$_{r'}$, wherein each of L', V', Y', z', q', and r' are as defined in Formula III, R is as defined in Formula I and wherein each (RR') is an addition product between an R of Formula I and its complementary R' of formula III (see, for example, FIG. 1 and FIG. 2). Thus, RR' can be an addition product of a: thio-maleimide (or halo-acetamide) addition, for example, a N,S-disubstituted-3-thio-pyrrolidine-2,5-dione; Staudinger ligation, for example, a N,3- or N,4-substituted-5-dipenylphosphinoxide-benzoic amide; Huisgen 1,3-cycloaddition (click reaction), for example, a N,S-disubstituted-3-thio-pyrrolidine-2,5-dione, 1,4-disubstituted-1,2,3-triazole, 3,5-disubstituted-isooxazole, or 3,5-disubstituted-tetrazole; Diels-Alder cycloaddition adduct, for example the 2,4-cycloaddition product between an O or N-substituted-5-norbornene-2-carboxylic ester or amide, N-substituted-5-norbornene-2,3-dicarboxylic imide, O or N-substituted-7-oxonorbornene-5-carboxylic ester or amide, or N-substituted-7-oxonorbornene-5,6-dicarboxylic imide and a 9-substituted anthracene or 3-substituted 1,2,4,5-tetrazine; or any high yield selective amidation or imidization reaction. Some reactions and the corresponding RR' reaction products are illustrated in FIGS. 1 and 2.

Optionally, a compound will comprise V or V' (but not both V and V'). Optionally, a compound will comprise Y or Y' (but not both Y and Y').

The linkers of Formula Ib can be reacted with an antibody, in the presence of a TGase and under suitable conditions, to produce an antibody comprising a functionalized acceptor glutamine of Formula IV.

In the simplest form, however, a compound of Formula Ic can be reacted with an antibody:

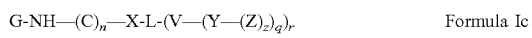

G-NH—(C)$_n$—X-L-(V—(Y—(Z)$_z$)$_q$)$_r$  Formula Ic wherein each of G, C, n, X, L, V, Y, z, q, and r are as defined in Formula Ia, and Z is a moiety-of-interest as described herein.

A compound may contain more than one L moiety. Any L' moiety can be defined in the same way as a L moiety. The L moieties may or may not be the same. The linking group L may be a water-soluble moiety or contain one or more water-soluble moieties, such that L contributes to the water solubility of a compound of formula (I)-(VI). An L may also be a moiety or contain one or more moieties that reduce(s) aggregation, which may or may not be a moiety/moieties that also increase(s) the water solubility.

L may be for example a linear linker or a branched linker. In one aspect, the L moiety is branched, optionally further a dendritic structure, so that it can be connected to at least two, three, four or more V, Y or R moieties (or Z where applicable). Each V-Y moiety is however only attached once to an L moiety. Branching can occur at one or more branching atoms that may for example be carbon, nitrogen, silicon, or phosphorus.

When the lysine-based linker comprises branching in L, the number of branches in L that are connected to V and/or Y will generally be prepared so as to equal the total number of branches available for reaction. That is, in preparing the lysine-based linker, chemical conversion will preferably be carried to completion, thereby maintaining the controlled stoichiometry offered by the site-specific TGase-mediated conjugation approach. Thus, preferably, when L is branched, compounds will be functionalized such that each L, V or Y is connected to a R moiety, such that the components of the mixture of antibodies (or the lysine-based linker during preparation) substantially all have the same r value. For example, it can be specified that 90%, 95%, 98% of the antibodies or the lysine-based linker have the same r value. In one embodiment, L is a linear linker. In another embodiment, L is a branched linker.

The Reactive Moiety R

R is a reactive moiety, for example a moiety comprising an unprotected or protected bioorthogonal-reaction compatible reactive group, for example an unprotected or protected thiol, epoxide, maleimide, haloacetamide, o-phoshenearomatic ester, azide, fulminate, sulfonate ester, alkyne, cyanide, amino-thiol, carbonyl, aldehyde, generally any group capable of oxime and hydrazine formation, 1,2,4,5-tetrazine, norbornene, other stained or otherwise electronically activated alkene, a substituted or unsubstituted cycloalkyne, generally any reactive groups which form via bioorthogonal cycloaddition reaction a 1,3- or 1,5-disubstituted triazole, any diene or strained alkene dienophile that can react via inverse electron demand Diels-Alder reaction, a protected or unprotected amine, a carboxylic acid, an aldehyde, or an oxyamine.

When more than one R group is present in a compound of the formula, the R groups will preferably be compatible such that no R group is a complementary reagent to any other R group. The L, V and/or Y groups of formulae I-IV can have r, q, and/or z sites of attachment for the respective V, Y, and R groups, where r and q represent the degree of branching or polymerization. The sites of attachment can comprise a bond or comprise a functional group selected from an alkene, alkyne, ether, thioether, ester, thioester, amine, amide, alkylamide, or other functional group readily generated by a condensation or addition reaction.

The reactive group of the linking reagent can for example chosen to undergo thio-maleimide (or haloacetamide) addition, Staudinger ligation, Huisgen 1,3-cycloaddition (click reaction), or Diels-Alder cycloaddition with a complementary reactive group attached to an agent comprising a therapeutic moiety, a diagnostic moiety, or any other moiety for a desired function.

Optionally, two or more compatible reactive groups can be attached to the linking reagent.

In one embodiment, the reactive group is a haloacetamide, (e.g. bromo-acetamide, iodo-acetamide, cloro-acetamide). Such reactive groups will be more stable in vivo (and in serum) compared with maleimide groups.

In one embodiment, the reactive group is a reagent capable of undergoing a "click" reaction. For example a 1,3-dipole-functional compound can react with an alkyne in a cyclization reaction to form a heterocyclic compound, preferably in the substantial absence of added catalyst (e.g., Cu(I)). A variety compounds having at least one 1,3-dipole group attached thereto (having a three-atom pi-electron system containing 4 electrons delocalized over the three atoms) can be used to react with the alkynes disclosed herein. Exemplary 1,3-dipole groups include, but are not limited to, azides, nitrile oxides, nitrones, azoxy groups, and acyl diazo groups.

Examples include o-phosphenearomatic ester, an azide, a fulminate, an alkyne (including any strained cycloalkyne), a cyanide, an anthracene, a 1,2,4,5-tetrazine, or a norbornene (or other strained cycloalkene).

In one embodiment, R is a moiety having a terminal alkyne or azide; such moieties are described for example in U.S. Pat. No. 7,763,736, the disclosure of which is incorporated herein by reference. Suitable reaction conditions for use of copper (and other metal salt) as catalysts of click-reactions between terminal alkynes and azides are provided in U.S. Pat. No. 7,763,736.

In one embodiment, R is a substituted or unsubstituted cycloalkyne. Cycloalkynes, including heterocyclic compounds, will preferably be used in linking reagents in which an L group is present, preferably wherein L is an alkyl or heteroalkyl chain of 3-30, optionally 5-30 or 5-15 linear carbon atoms, optionally substituted at one or more atoms. Optionally, L is a (CH$_2$—CH$_2$—O)$_{1-24}$ group or a (CH$_2$)$_{x1}$—(CH$_2$—O—CH$_2$)$_{1-24}$—(CH$_2$)$_{x2}$—, wherein x1 and x2 are independently an integer selected among the range of 0 to 20. As shown herein, presence of an L group enables high TGase-mediated coupling when cycloalkynes are used.

Cycloalkynes, including specific compounds, are described for example in U.S. Pat. No. 7,807,619, the disclosure of which is incorporated herein by reference.

In some embodiments, a cycloalkyne may be a compound of Formula A:

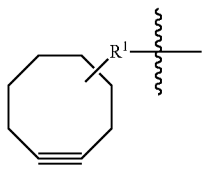

Formula A where:

R¹ is selected from a carbonyl, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone, and a halosulfonyl;

R¹ can be at any position on the cyclooctyne group other than at the two carbons joined by the triple bond.

In some embodiments, the modified cycloalkyne is of Formula A, wherein one or more of the carbon atoms in the cyclooctyne ring, other than the two carbon atoms joined by a triple bond, is substituted with one or more electron-withdrawing groups, e.g., a halo (bromo, chloro, fluoro, iodo), a nitro group, a cyano group, a sulfone group, or a sulfonic acid group. Thus, e.g., in some embodiments, a subject modified cycloalkyne is of Formula B:

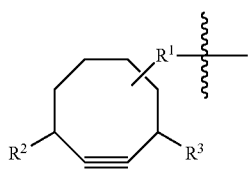

Formula B where:

each of $R^2$ and $R^3$ is independently: (a) H; (b) a halogen atom (e.g., bromo, chloro, fluoro, iodo); (c) —W—$(CH_2)_n$-Z (where: n is an integer from 1-4 (e.g., n=1, 2, 3, or 4); W, if present, is O, N, or S; and Z is nitro, cyano, sulfonic acid, or a halogen); (d) —$(CH_2)_n$—W—$(CH_2)_m$—$R^4$ (where: n and m are each independently 1 or 2; W is O, N, S, or sulfonyl; if W is O, N, or S, then $R^4$ is nitro, cyano, or halogen; and if W is sulfonyl, then $R^4$ is H); or (e) —$(CH_2)_n$—$R^4$ (where: n is an integer from 1-4 (e.g., n=1, 2, 3, or 4); and $R^4$ is nitro, cyano, sulfonic acid, or a halogen); and R¹ is selected from a carbonyl, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone and a halosulfonyl. R¹ can be at any position on the cyclooctyne group other than at the two carbons linked by the triple bond.

In one embodiment, R is a substituted or unsubstituted heterocyclic strained alkyne. Cycloalkynes, including specific compounds, are described for example in U.S. Pat. No. 8,133,515, the disclosure of which is incorporated herein by reference. In one embodiment, the alkyne is of the Formula C:

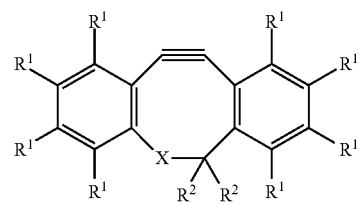

Formula C wherein:

each R¹ is independently selected from the group consisting of hydrogen, halogen, hydroxy, alkoxy, nitrate, nitrite, sulfate, and a $C_1$-$C_{10}$ alkyl or heteroalkyl;

each R² is independently selected from the group consisting of hydrogen, halogen, hydroxy, alkoxy, nitrate, nitrite, sulfate, and a $C_1$-$C_{10}$ organic group; X represents N—$R^3R^4$, NH—$R^4$, CH—N—$OR^4$, C—N—$NR^3R^4$, $CHOR_4$, or $CHNHR_4$; and each R³ represents hydrogen or an organic group and R⁴ represents linking moiety C (or $(C)_n$) of a linker. In one embodiment, R or R' is a DBCO (dibenzycyclooctyl) group below:

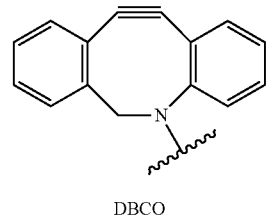 [SMILES: *N1Cc2ccccc2C#Cc2ccccc21 ; "DBCO"]

DBCO

Alkynes such as those described herein above can be reacted with at least one 1,3-dipole-functional compound (e.g., embodied as an R' moiety in a compound of Formula III) in a cyclization reaction to form a heterocyclic compound, preferably in the substantial absence of added catalyst (e.g., Cu(I)). A wide variety compounds having at least one 1,3-dipole group attached thereto (having a three-atom pi-electron system containing 4 electrons delocalized over the three atoms) can be used to react with the alkynes disclosed herein. Exemplary 1,3-dipole groups include, but are not limited to, azides, nitrile oxides, nitrones, azoxy groups, and acyl diazo groups.

The reactive moiety R is connected to L, or when present, V or Y, and is able to react with a suitable functional group (R') on a reaction partner, e.g. a complementary reagent of Formula III which undergoes a high conversion addition reaction when brought into contact with a reactive moiety R. When reactive moiety R is present in an antibody of Formula II, the reaction results in formation of an antibody of Formula IV. In this reaction, the moieties R and R' are transformed into the moiety (RR'). Any R' moiety can be defined in the same way as a R moiety, so long as R and R' are complementary when used in moieties that are to be reacted together.

A compound may contain more than one reactive moiety R. The R moieties may or may not be the same.

FIG. 1 shows reaction schemes for thio-maleimide additions, Staudinger ligations, and Diels-Alder cycloadditions, where reactive groups of linking reagents having a single reactive functionality combine with complementary reactive group attached to a therapeutic or diagnostic moiety.

FIG. 2 shows reaction schemes for Diels-Alder cycloadditions and click reactions where the reactive groups of linking reagents combine with complementary reactive group attached to an agent including a therapeutic, diagnostic, or other moiety.

It should be understood that, although not illustrated in FIGS. 1 and 2, the $H_2NCH_2$ group of the linking reagent may have undergone reaction with the glutamine residue of a protein (e.g. antibody) prior to the high conversion addition reaction or that the aminomethylene may be in a protected state. Alternatively, in other embodiments, the $H_2NCH_2$ group of the linking reagent will not have undergone reaction with the glutamine residue of a protein (e.g. antibody) prior to the high conversion addition reaction or that the aminomethylene may be in a protected state; in this case the linking reagent and reaction partner can be used to conveniently form various combinations of linkers having different V, Y, and/or Z moieties that are ready to conjugate to an antibody.

Figure 3:
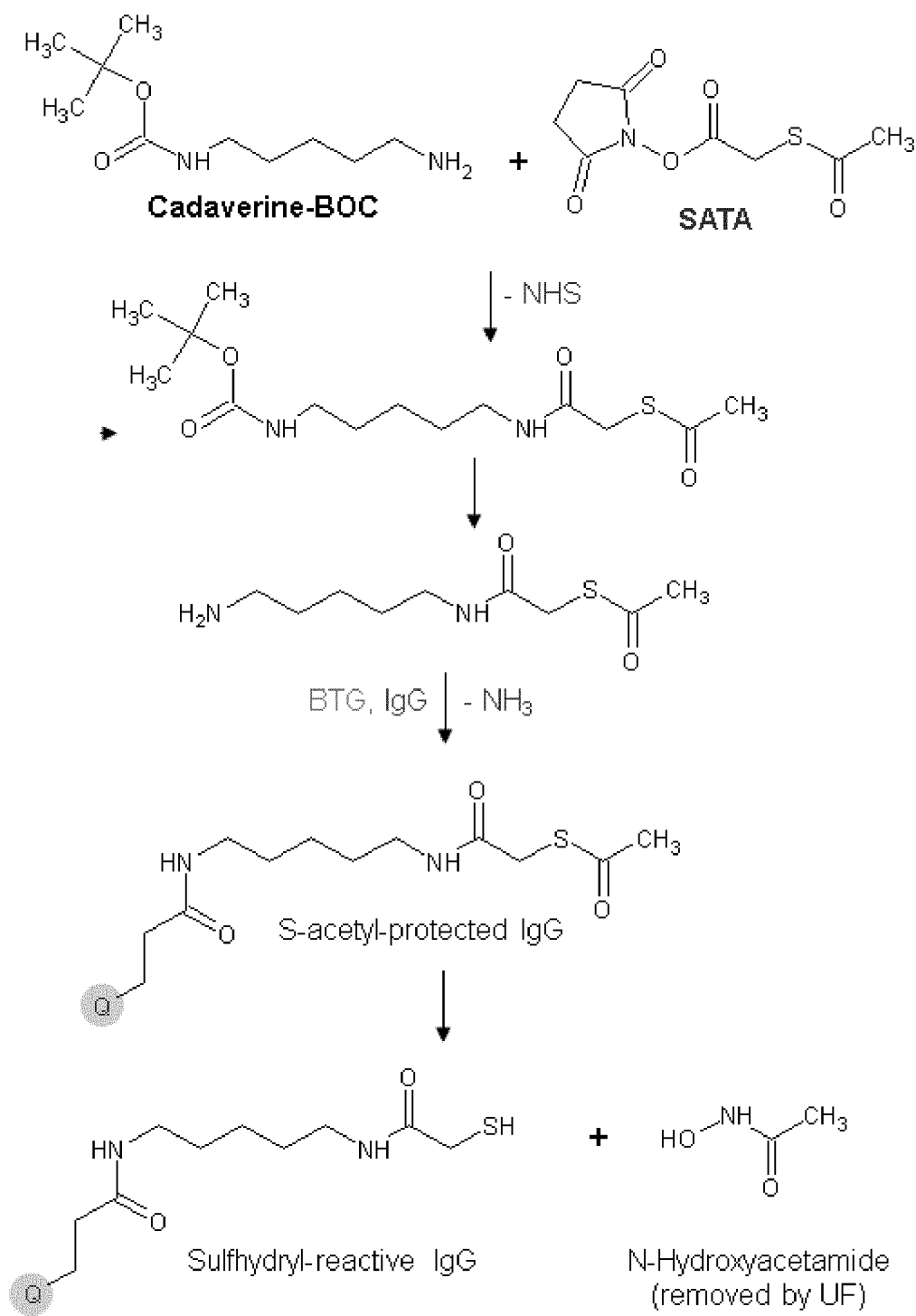
FIG. 3 shows the preparation of an exemplary linking reagent, and its conjugation with a protein, where: V and Y are absent, R is a thiol (sulfhydryl) reactive group that is ultimately generated from the S-acetyl protected thiol, $SC(O)CH_3$; r is 0; q is 0; z is 1; L is the two carbon comprising framework $C(O)CH_2$; X is NH; $(C)_n$ is $(CH_2)_5$; and G is transformed from the $(H_3C)_3COC(O)$ protecting group to H and ultimately to the amide upon conjugation of a glutamine residue of a protein.
Figure 4:
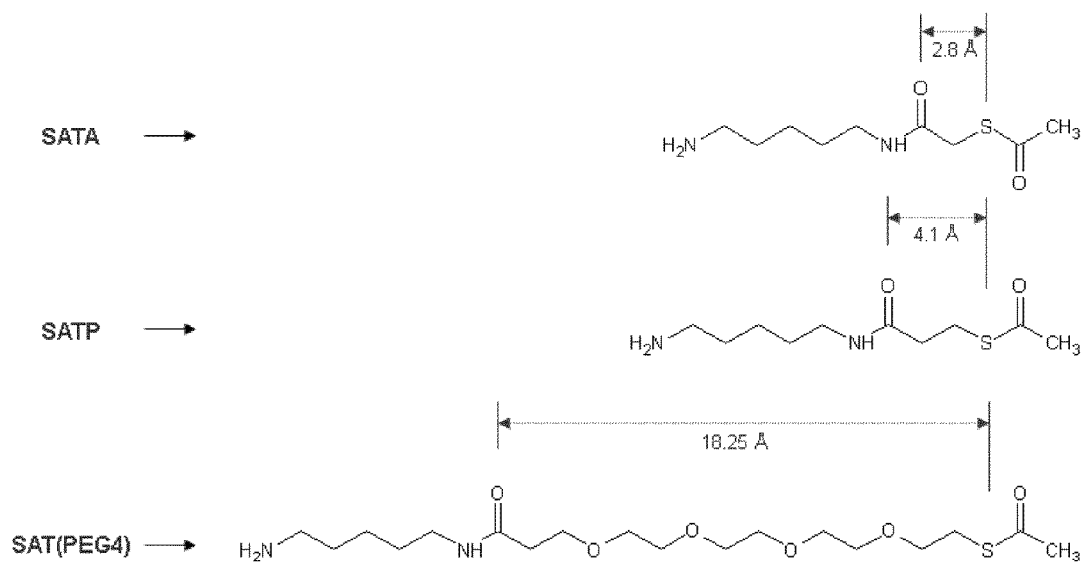
FIG. 4 illustrates the preparation of various exemplary linking reagents, according to various embodiments, with a single S-acetyl protected thiol reactive group that can be prepared from an N-succinimidyl-S-acetylthioester reagent.

The preparation of an exemplary linking reagent, according to one embodiment, and its conjugation with a protein is illustrated in FIG. 3, where: V and Y are absent, R is a thiol (sulfhydryl) reactive group that is ultimately generated from the S-acetyl protected thiol, $SC(O)CH_3$; r is 1; q is 1; z is 1; L is the two carbon comprising framework $C(O)CH_2$; X is NH; $(C)_n$ is $(CH_2)_5$; and G is transformed from the $(H_3C)_3COC(O)$ protecting group to H and ultimately to the amide upon conjugation of a glutamine residue of a protein. FIG. 4 illustrates the preparation of various exemplary linking reagents, according to various embodiments, with a single S-acetyl protected thiol reactive group that can be prepared from an N-succinimidyl-S-acetylthioester reagent. In addition to S-acetyl, other S-protecting groups can be employed, including p-hydroxyphenylacyl, 2-quinoline, or Hqm and Hgm groups that can be deprotected by the addition of hydrazine.

Figure 5:
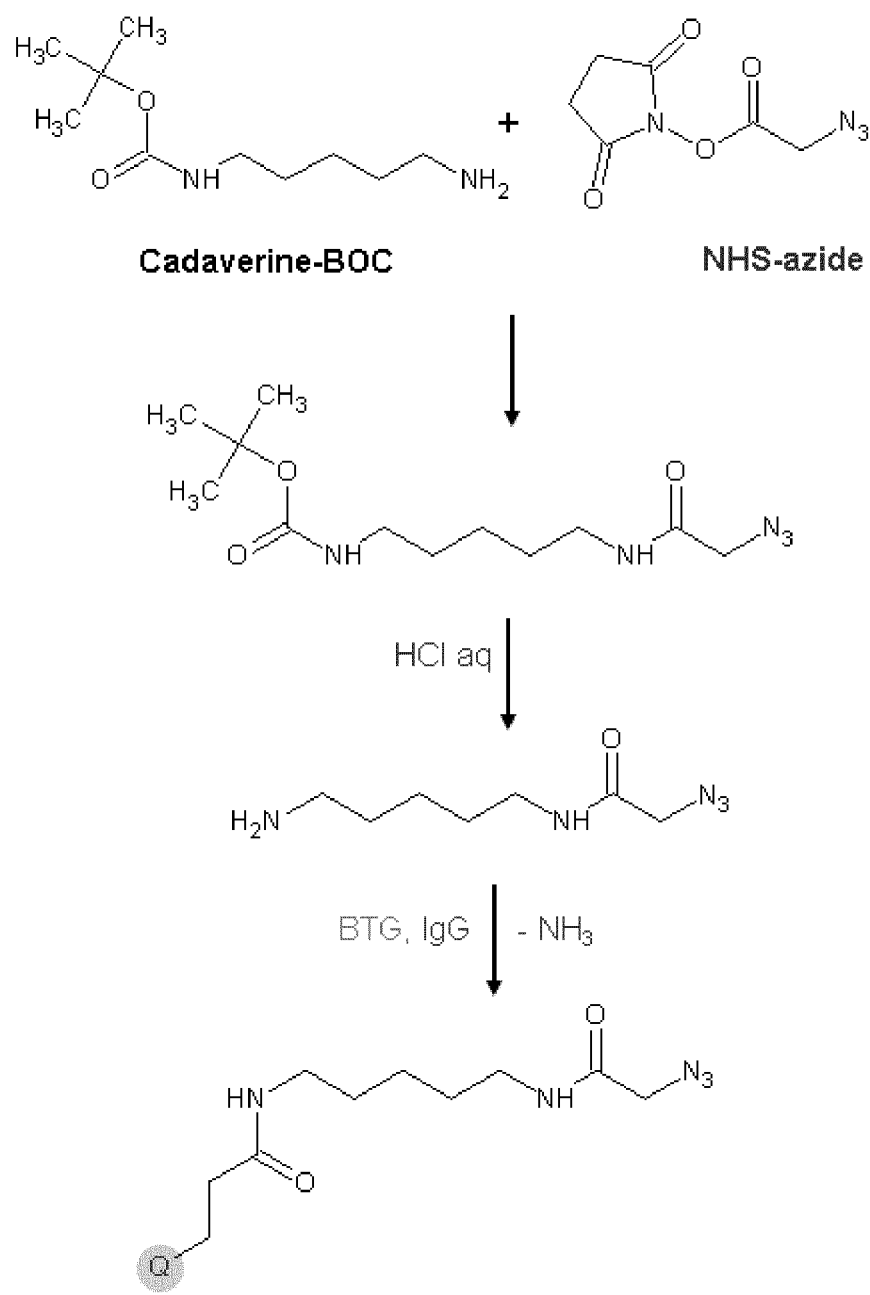
FIG. 5 illustrates the preparation of an exemplary linking reagent, and its conjugation with a protein, where: V and Y are absent, R is an azide reactive group; r is 0; q is 0; z is 1; L is the two carbon comprising framework $C(O)CH_2$; X is NH; $(C)_n$ is $(CH_2)_5$; and G is transformed from the $(H_3C)_3COC(O)$ protecting group to H and ultimately to the amide upon conjugation of a glutamine residue of a protein.
Figure 6:
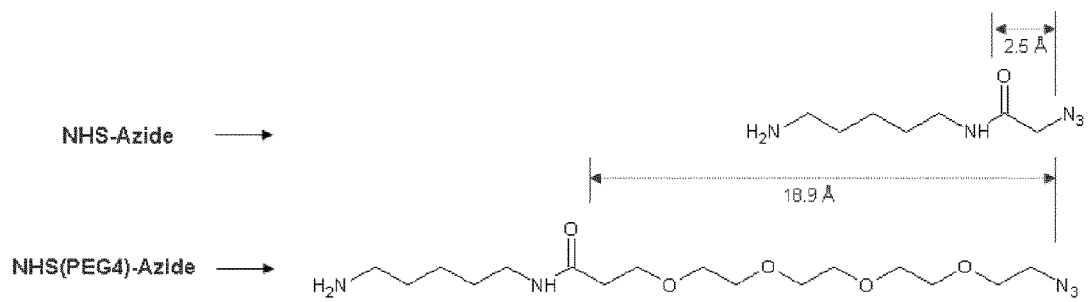
FIG. 6 illustrates the preparation of various exemplary linking reagents, with a single azide reactive group that can be prepared from an N-succinimidyl-azide reagent.

FIG. 5 illustrates the preparation of an exemplary linking reagent, according to one embodiment, and its conjugation with a protein, where: V and Y are absent, R is an azide reactive group; r is 1; q is 1; z is 1; L is the two carbon comprising framework $C(O)CH_2$; X is NH; $(C)_n$ is $(CH_2)_5$; and G is transformed from the $(H_3C)_3COC(O)$ protecting group to H and ultimately to the amide upon conjugation of a glutamine residue of a protein. FIG. 6 illustrates the preparation of various exemplary linking reagents, with a single azide reactive group that can be prepared from an N-succinimidyl-azide reagent.

Figure 7:
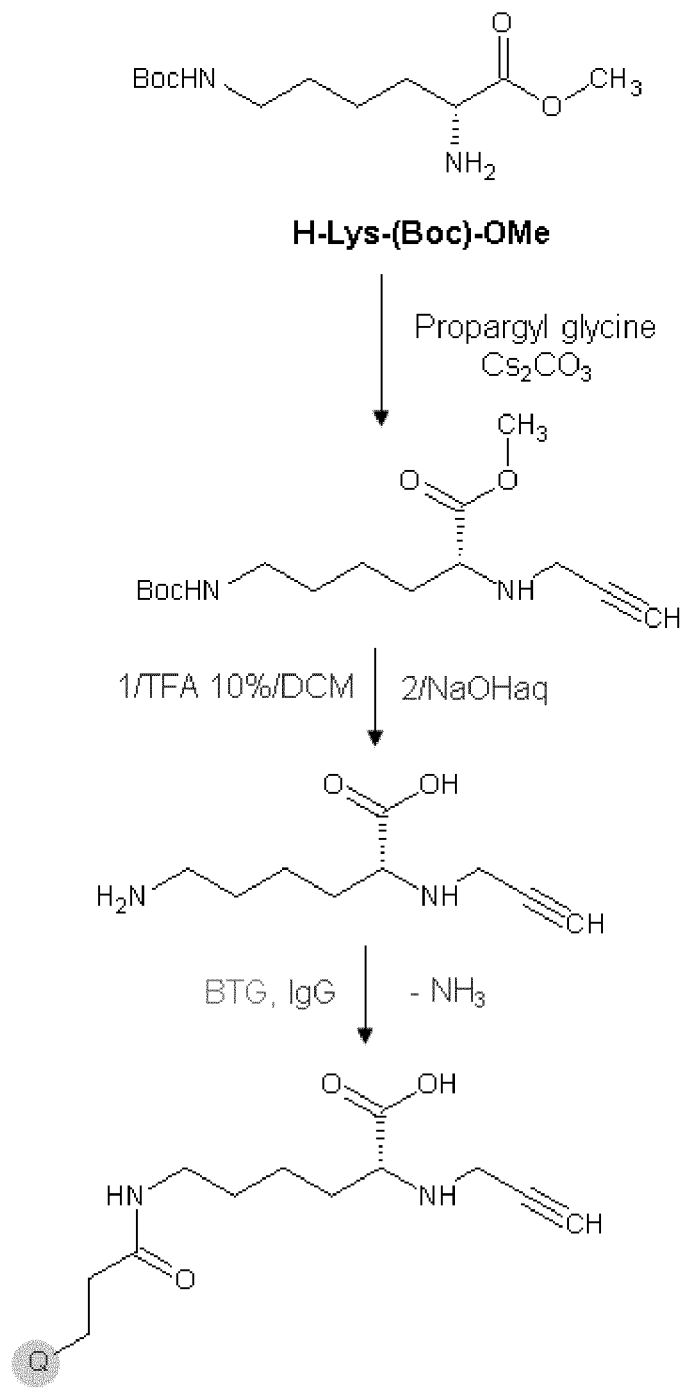
FIG. 7 depicts the preparation of an exemplary linking reagent, and its conjugation with a protein, where: V and Y are absent, R is an alkyne reactive group; r is 0; q is 0; z is 1; L is a one carbon comprising framework $CH_2$; X is NH; $(C)_n$ is $(CH_2)_4CH(CO_2H)$; and G is transformed from the $(H_3C)_3COC(O)$ protecting group to H and ultimately to the amide upon conjugation of a glutamine residue of a protein.
Figure 8:
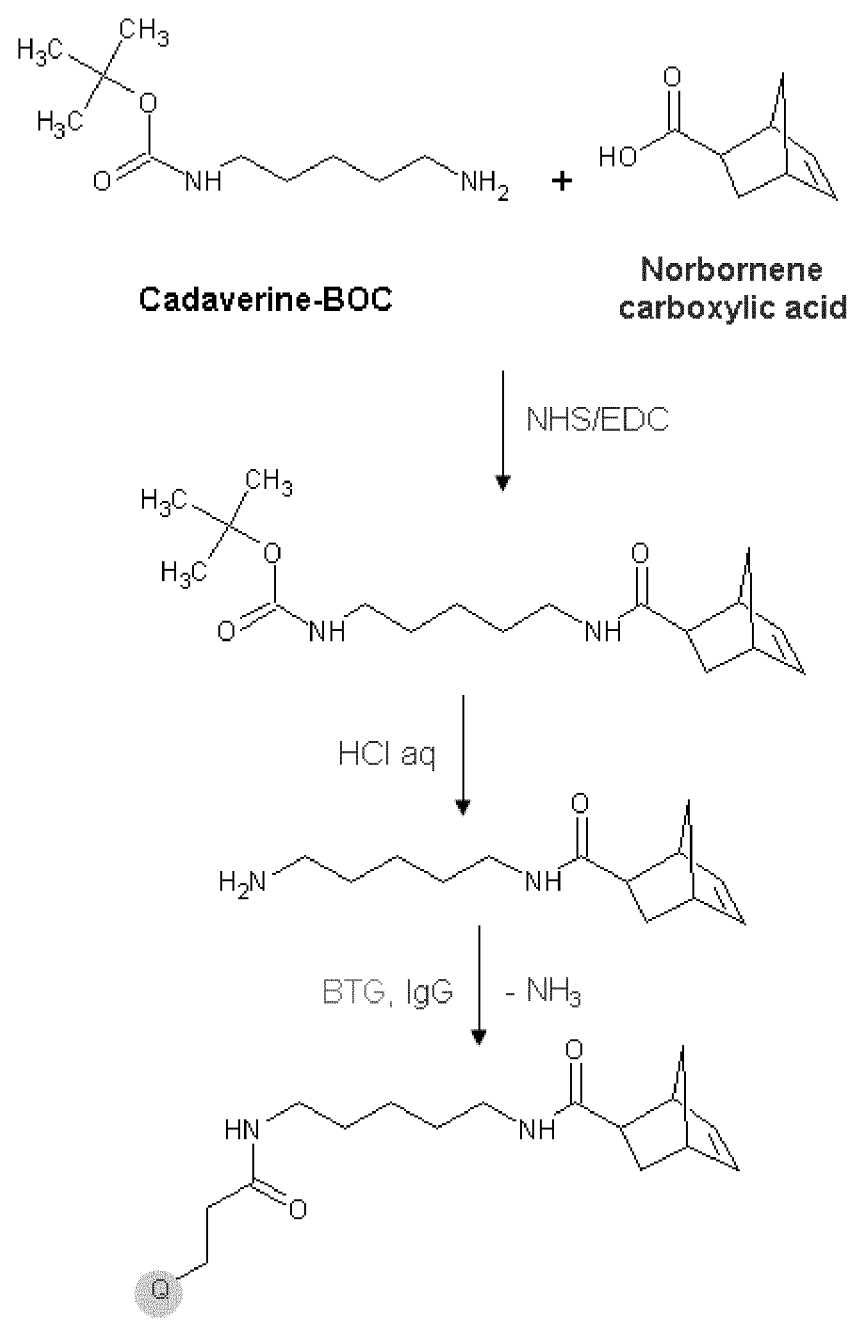
FIG. 8 shows the preparation of an exemplary linking reagent, and its conjugation with a protein, where: R is a norbornene reactive group; r is 0; q is 0; z is 1; L is the one carbon comprising framework C(O); X is NH; $(C)_n$ is $(CH_2)_4CH(CO_2H)$; and G is transformed from the $(H_3C)_3COC(O)$ protecting group to H and ultimately to the amide upon conjugation of a glutamine residue of a protein.

FIG. 7 depicts the preparation of an exemplary linking reagent, and its conjugation with a protein, where: V and Y are absent, R is an alkyne reactive group; r is 1; q is 1; z is 1; L is a one carbon comprising framework $CH_2$; X is NH; $(C)_n$ is $(CH_2)_4CH(CO_2H)$; and G is transformed from the $(H_3C)_3COC(O)$ protecting group to H and ultimately to the amide upon conjugation of a glutamine residue of a protein. FIG. 8 shows the preparation of an exemplary linking reagent, and its conjugation with a protein, where: R is a norbornene reactive group; r is 1; q is 1; z is 1; L is the one carbon comprising framework $C(O)$; X is NH; $(C)_n$ is $(CH_2)_4CH(CO_2H)$; and G is transformed from the $(H_3C)_3COC(O)$ protecting group to H and ultimately to the amide upon conjugation of a glutamine residue of a protein.

The selective and very high conversion addition reaction that can be carried out with the linking reagents, can be uncatalyzed or catalyzed reactions. For example, the 2+4 Diels-Alder cycloadditions, thio-maleimide (or -haloacetamide) additions, and Staudinger ligations can be carried out without a catalyst. Other very high conversion addition reactions, for example any of the click reactions, can be catalyzed with metal salts, such as Cu, Ru, Ni, Pd, and Pt salts.

The linking group (RR') in M of compounds of Formula IV represents the remainder of R when the reactive moiety R of Formula II has reacted with a reactive moiety R' in a compound of Formula III. This group (RR') then links the moiety Z (e.g. comprised in the compound of formula IV) with L, V or Y. The group that remains may be a bond.

Figure 9:
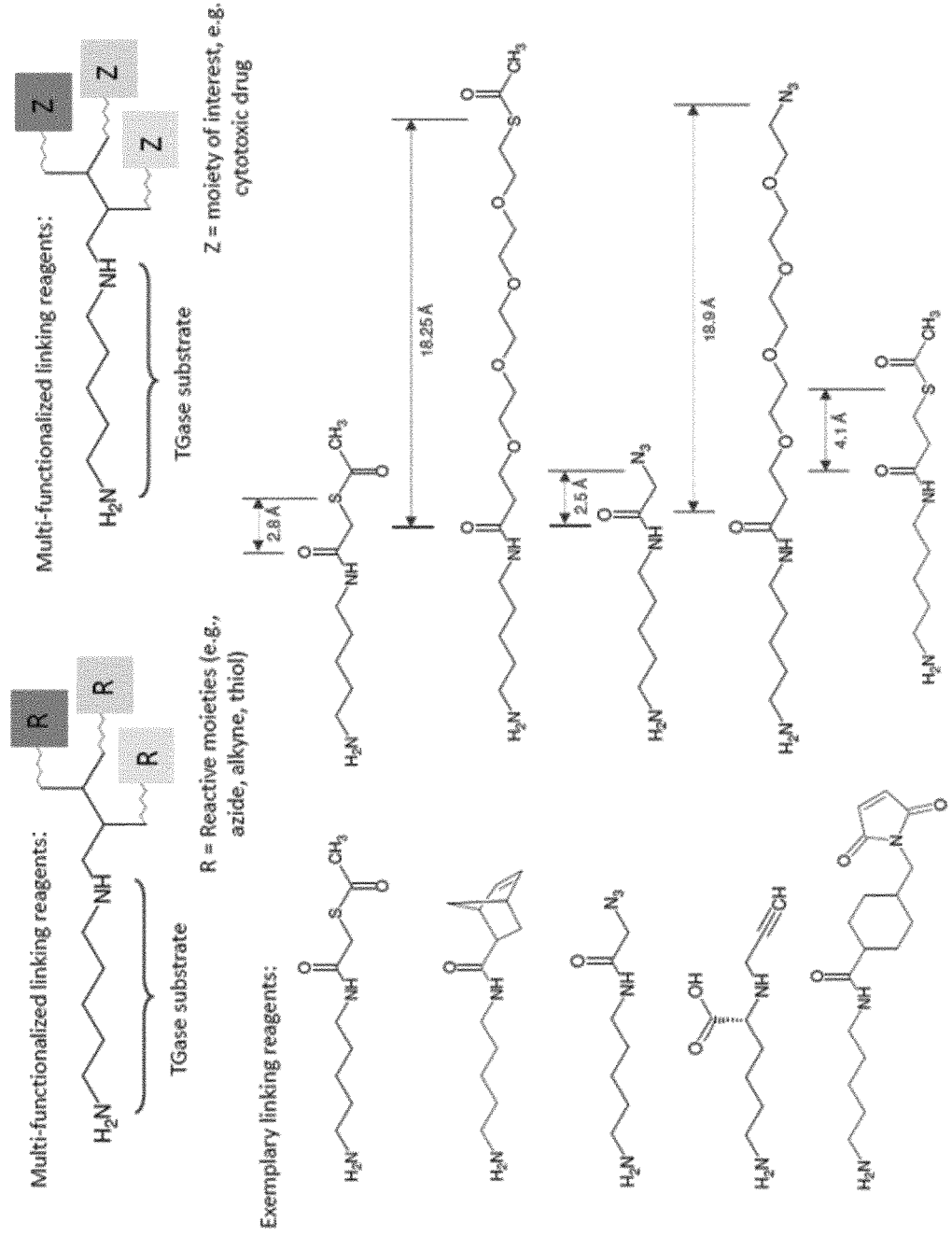
FIG. 9 shows various examples of linking reagents.
Figure 10:
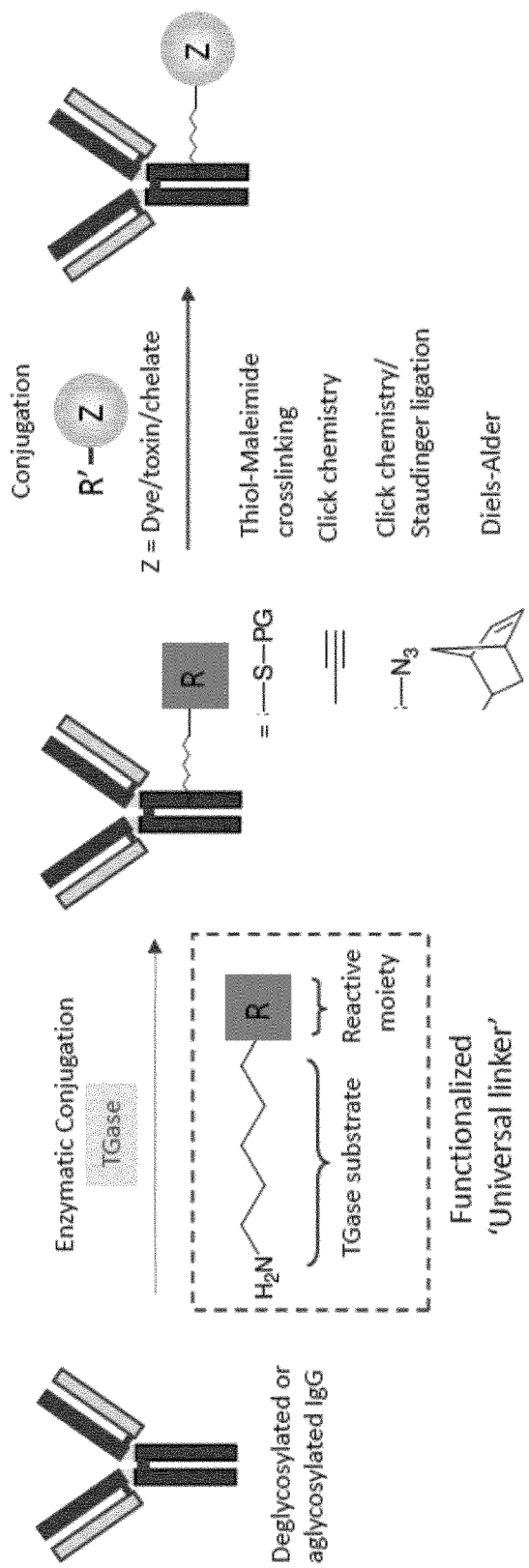
FIG. 10 shows a general scheme for preparing conjugated antibodies.
Figure 11:
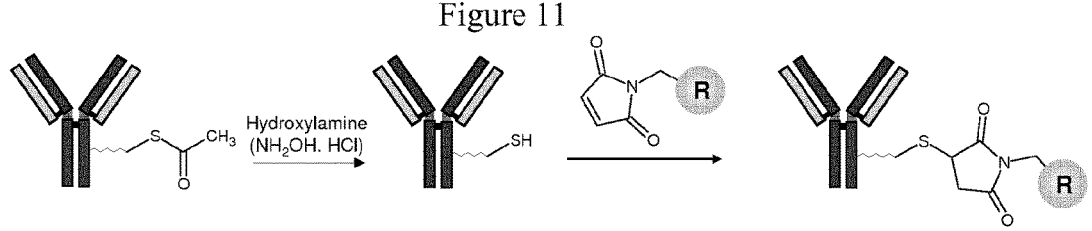
FIG. 11 shows a scheme for preparing an antibody conjugate from a S-acetyl-cadaverine linker of FIG. 3, where "R" in the figure is a moiety-of-interest Z.
Figure 12:
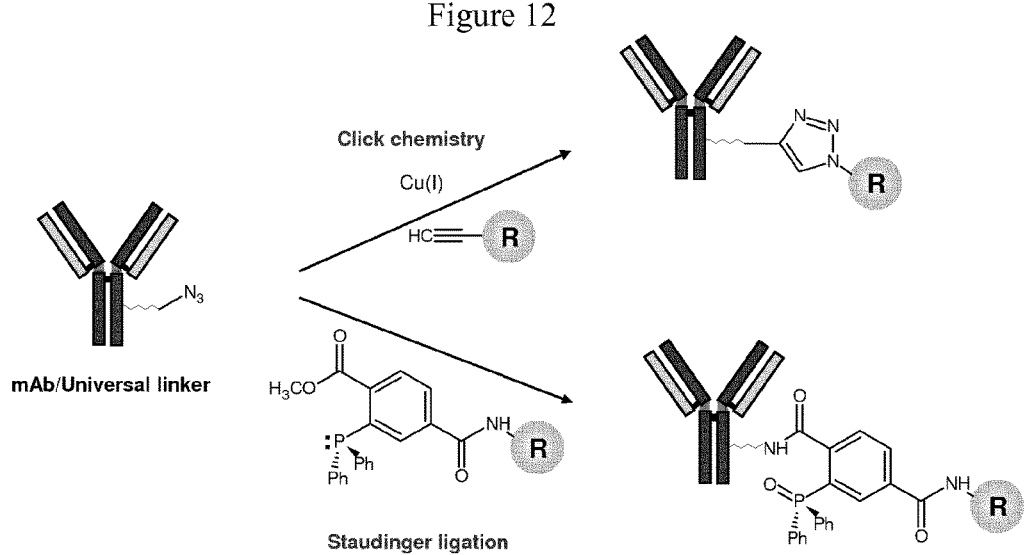
FIG. 12 shows a scheme for preparing an antibody conjugate from an azide-cadaverine linker of FIG. 5, where "R" in the figure is a moiety-of-interest Z.
Figure 13:
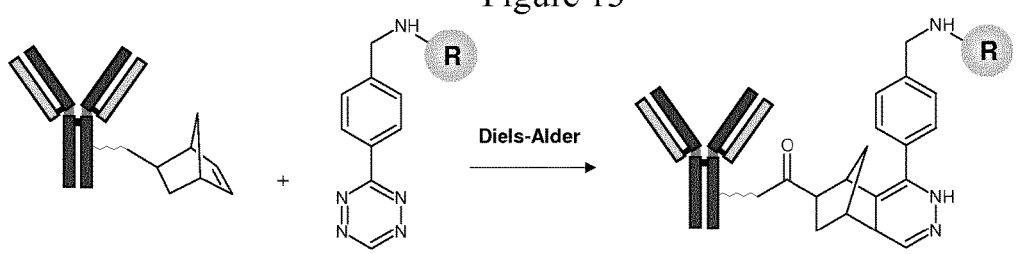
FIG. 13 shows a scheme for preparing an antibody conjugate from a norbornyl-cadaverine linker of FIG. 8, where "R" in the figure is a moiety-of-interest Z.
Figure 14:
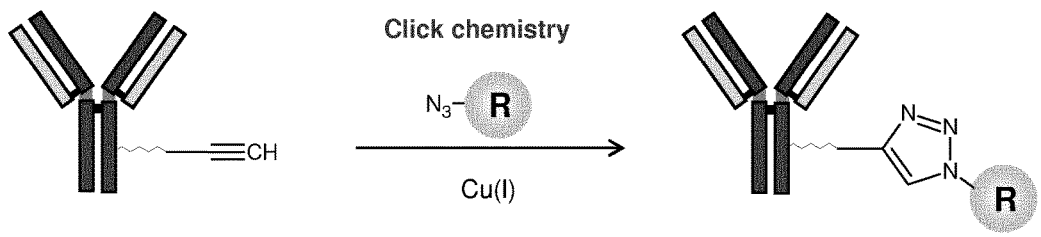
FIG. 14 shows a scheme for preparing an antibody conjugate from a glycan-lysine derivative linker of FIG. 7, where "R" in the figure is a moiety-of-interest Z.

Examples of lysine-based linkers are shown in FIG. 9.

The V Moiety

The V moiety may be incorporated in the lysine-based linker (e.g. connected to L, optionally through Y). However, the V moiety may instead or in addition be incorporated in a compound comprising a moiety-of-interest Z (e.g. a compound R'—V—Y—Z of formula III) that will be reacted with an antibody conjugated with a lysine-based linker to form an antibody conjugated to the moiety-of-interest Z. Any V' moiety can be defined in the same way as a V moiety.

The V moiety is a group that is either non-cleavable or conditionally cleavable, optionally after prior conditional transformation. In the latter case, it is designed to be transformed and/or cleaved from Y, or Z when Y is absent, by a chemical, photochemical, physical, biological, or enzymatic process, e.g. in certain conditions. This condition may for example comprise bringing a compound in an aqueous environment, which leads to hydrolysis of V, or bringing a compound in an environment that contains an enzyme that recognizes and cleaves V, or bringing a compound under reducing conditions, which leads to reduction of V, or bringing a compound in contact with radiation, e.g., UV light, which leads to transformation and/or cleavage, or bringing a compound in contact with heat, which leads to transformation and/or cleavage, or bringing a compound of the invention under reduced pressure or bringing a compound under elevated or high pressure, which leads to transformation and/or cleavage. This condition may further be met after administrating a compound to an animal, e.g., a mammal: the condition may be met when the compound localizes to for example a specific organ, tissue, cell, subcellular target, or microbial target, for example by the presence of internal factors (e.g., target-specific enzymes or hypoxia) or application of external factors (e.g., radiation, magnetic fields) or the condition may already be met directly upon administration (e.g., enzymes). In general, transformation of V will directly or indirectly lead to cleavage of V from Y, or Z when Y is absent. It may occur that two or more separate transformations and/or cleavages, requiring the same or different conditions, are required in order to cleave V completely from Y or Z. In this way, increased selectivity may be obtained. A compound may contain more than one V moiety. These V moieties may or may not be the same and may or may not require the same conditions for transformation and/or cleavage.

In one aspect of this invention, a compound is used to target one or more therapeutic and/or diagnostic moieties Z to target cells. In this instance, V may for example contain a substrate molecule that is cleaved by an enzyme present in the vicinity of the target cells or inside the target cells, for example tumor cells. V can for example contain a substrate that is cleaved by an enzyme present at elevated levels in the vicinity of or inside the target cells as compared to other parts of the body, or by an enzyme that is present only in the vicinity of or inside the target cells.

If target cell specificity is achieved solely based upon the selective transformation and/or cleavage of V at the target site, the condition (eventually) causing the cleavage should preferably, at least to a certain degree, be target cell-specific, whereas the presence of another target-specific moiety in the compound, for instance when the antibody recognizes an antigen present on a target cell with a degree of specificity, reduces or takes away this requirement. For example, when an antibody causes specific internalization into a target cell, an enzyme also present in other cells may transform and/or cleave V. In one embodiment, transformation and/or cleavage of V occurs intracellularly. In another embodiment, transformation and/or cleavage of V occurs extracellularly.

In one embodiment, the V moiety is a conditionally cleavable moiety.

In one embodiment, V contains a di-, tri-, tetra-, or oligopeptide which consists of an amino acid sequence recognized by a protease, for example plasmin, a cathepsin, cathepsin B, prostate-specific antigen (PSA), urokinase-type plasminogen activator (u-PA), or a member of the family of matrix metalloproteinases, present in the vicinity of or inside the target cells, for example tumor cells. In one embodiment V is a dipeptide, tripeptide, tetrapeptide, or oligopeptide moiety comprised of natural L amino acids, unnatural D amino acids, or synthetic amino acids, or a peptidomimetic, or any combination thereof. In one embodiment, V is a peptide. In another embodiment, V is a dipeptide. In another embodiment, V is a tripeptide. In another embodiment, V is a tetrapeptide. In yet another embodiment, V is a peptidomimetic.

In one embodiment, V contains a substrate for an enzyme.

In another embodiment, V contains a beta-glucuronide that is recognized by beta-glucuronidase present in the vicinity of or inside tumor cells.

In one embodiment, V contains a substrate for an extracellular enzyme. In another embodiment, V contains a substrate for an intracellular enzyme.

In yet another embodiment, V contains a substrate for a lysosomal enzyme.

In yet another embodiment, V contains a substrate for the serine protease plasmin.

In yet another embodiment, V contains a substrate for one or more of the cathepsins, for example cathepsin B. When V is cleaved extracellularly, the one or more Z moieties may be released extracellularly. This may provide the advantage that these Z moieties are not only able to affect or detect the cell(s) directly surrounding the site of activation, but also cells somewhat further away from the site of activation due to diffusion (bystander effect).

In one embodiment V comprises a tripeptide. The tripeptide may be linked via its C-terminus to Y. In one embodiment, the C-terminal amino acid residue of the tripeptide is selected from arginine, citrulline, and lysine, the middle amino acid residue of the tripeptide is selected from alanine, valine, leucine, isoleucine, methionine, phenylalanine, cyclohexylglycine, tryptophan and proline, and the N-terminal amino acid residue of the tripeptide is selected from any natural or unnatural amino acid.

In another embodiment V comprises a dipeptide. The dipeptide may be linked via its C-terminus to Y. In one embodiment, the C-terminal amino acid residue of the dipeptide is selected from alanine, arginine, citrulline, and lysine, and the N-terminal amino acid residue of the dipeptide is selected from any natural or unnatural amino acid. In one embodiment, V is selected from phenylalanyllysme and valylcitrulline.

In another aspect, a compound is used to improve the pharmacokinetic properties of Z. V may in this case for example be or contain a group that is cleaved by ubiquitous enzymes, e.g., esterases that are present in the circulation, by pH-controlled intramolecular cyclization, or by acid-catalyzed, base-catalyzed, or non-catalyzed hydrolysis, or V may for example be or contain a disulfide. V may therefore, optionally together with the connecting atom of L and/or Y (or Z if Y is absent), for example form a carbonate, carbamate, ureum, ester, amide, imine, hydrazone, oxime, disulfide, acetal, or ketal group. It is understood that V can also be or contain such a moiety and/or be transformed and/or cleaved in the same or a similar way when a compound of this invention is used for other purposes than solely improving the pharmacokinetic properties of Z.

When the compounds are used for other purposes, e.g., an ex vivo diagnostic assay, V may be or contain any of the moieties mentioned above and transformation and/or cleavage of V may occur by any one of the processes mentioned above or by any other functional transformation or cleavage process known to a person skilled in the art. For example, in a diagnostic assay, V may be cleaved or transformed by an enzyme, by reduction, or below, above, or at a certain pH.

When V is conditionally cleavable, the compounds are designed to eventually release at least one Z after cleavage and optional prior transformation of V. Release of Z from a compound via another mechanism is however not excluded.

In any embodiment, V may contain a blocking group to prevent premature transformation and/or cleavage of V before the condition is met under which V is designed to be transformed and/or cleaved.

In another aspect, V is a moiety that is non-cleavable. This means that V cannot be cleaved from Y, or Z when Y is absent, under the conditions the compound containing such a V moiety is designed to be applied, meaning that Z cannot be released in this way. Release of Z from a compound via another mechanism is however not excluded. When V is a non-cleavable moiety, Y may optionally be absent. A non-cleavable V moiety may be any moiety that cannot be cleaved, or that can be cleaved only very slowly, under the conditions the compound containing such a V moiety is designed to be applied, e.g. in vivo or in vitro. For example, when applied in vivo, V will not or only very slowly be cleaved by enzymes present in the in vivo model used or by hydrolysis or as a consequence of other biological processes that may occur in said model. Such V may therefore, optionally together with the connecting atom of L and/or Z, for example, be a carbonyl group, an amide group, an ureum group, an ester group, a carbonate group, a carbamate group, or an optionally substituted methyleneoxy or methyleneamino group V may be preferred to be non-cleavable when it is not required that the one or more moieties Z are released. This may for example be the case when Z does not require to become released before it can exert its therapeutic or diagnostic properties.

In one embodiment V is connected to L via a functional group in the side chain of one of the natural or unnatural amino acids. In another embodiment, the N-terminal amino acid of V is connected via its alpha amino group to L.

The Spacer System Y

The spacer system Y, when present, links V and optionally L to one or more moieties R, and following reaction with a compound of Formula III, a moiety-of-interest Z. In one embodiment, Y is absent. In another embodiment, Y is a self-elimination spacer system. A spacer system Y may be incorporated in a compound to for example improve the properties of Z or the compound in general, to provide suitable coupling chemistries, or to create space between V and Z. Any Y' moiety can be defined in the same way as a Y moiety.

A compound may contain more than one spacer system Y. These moieties Y may or may not be the same. When a self-elimination spacer is connected to one or more other self-elimination spacers via a direct bond, this combination of spacers is referred to as 'spacer system'. Herein, a single self-elimination spacer may also be referred to as a spacer system. A spacer system may be branched or unbranched and contain one or more attachment sites for Z as well as V. Self-elimination spacers that are able to release only a single moiety are called 'single release spacers'. Self-elimination spacers that are able to release two or more moieties are called 'multiple release spacers'. Spacers, may be either branched or unbranched and self-eliminating through a 1,2+2n-elimination (n>/=1), referred to as "electronic cascade spacers". Spacers may eliminate through a cyclization process under formation of a cyclic ureum derivative, referred to as "ω-amino aminocarbonyl cyclization spacers".

The spacer system Y may self-eliminating or non-self-eliminating. A "self-eliminating" spacer unit allows for release of the drug moiety without a separate hydrolysis step. When a self-eliminating spacer is used, after cleavage or transformation of V, the side of Y linked to V becomes unblocked, which results in eventual release of one or more moieties Z. The self-elimination spacer systems may for example be those described in WO 02/083180 and WO 2004/043493, which are incorporated herein by reference in their entirety, as well as other self-elimination spacers known to a person skilled in the art. In certain embodiments, a spacer unit of a linker comprises a p-aminobenzyl unit. In one such embodiment, a p-aminobenzyl alcohol is attached to an amino acid unit via an amide bond, and a carbamate, methylcarbamate, or carbonate is made between the benzyl alcohol and a cytotoxic agent. In one embodiment, the spacer unit is p-aminobenzyloxycarbonyl (PAB). Examples of self-eliminating spacer units further include, but are not limited to, aromatic compounds that are electronically similar to p-aminobenzyl alcohol (see, e.g., US 2005/0256030 A1), such as 2-aminoimidazol-5-methanol derivatives (Hay et al. (1999) Bioorg. Med. Chem. Lett. 9:2237) and ortho- or para-aminobenzylacetals. Spacers can be used mat undergo cyclization upon amide bond hydrolysis, such as substituted and unsubstituted 4-aminobutyric acid amides (Rodrigues et al., Chemistry Biology, 1995, 2, 223) and 2-aminophenyl-propionic acid amides (Amsberry, et al., J. Org. Chem., 1990, 55. 5867). Elimination of amine-containing drugs that are substituted at the a-position of glycine (Kingsbury, et al., J. Med. Chem., 1984, 27, 1447) are also examples of self-immolative spacers.

A "non-self-eliminating" spacer unit is one in which part or all of the spacer unit remains bound to the moiety Z upon enzymatic (e.g., proteolytic) cleavage of the antibody-moiety-of-interest conjugate. Examples of non-self-eliminating spacer units include, but are not limited to, a glycine spacer unit and a glycine-glycine spacer unit. Other combinations of peptidic spacers susceptible to sequence-specific enzymatic cleavage are also contemplated. For example, enzymatic cleavage of an antibody-moiety-of-interest conjugate containing a glycine-glycine spacer unit by a tumor-cell associated protease would result in release of a glycine-glycine-drug moiety from the remainder of the antibody-moiety-of-interest conjugate. In one such embodiment, the glycine-glycine-drug moiety is then subjected to a separate hydrolysis step in the tumor cell, thus cleaving the glycine-glycine spacer unit from the drug moiety.

A spacer system Y may be connected to more than one V moiety. In this case, transformation and/or cleavage of one of these V moieties may trigger the release of one or more Z moieties. When V moieties that are transformed or cleaved under different conditions are connected to the same Y, release of one or more Z moieties may occur when a compound is brought under one of several different conditions.

Conjugation of Lysine-Based Linkers to an Antibody

Enzymes of the TG-family catalyze covalent protein crosslinking by forming proteinase resistant isopeptide bonds between a lysine donor residue of one protein and an acceptor glutamine residue of another protein, and is accompanied by the release of ammonia. The antibodies that are to be conjugated to the lysine-based linker may or may not be free of N-linked glycosylation (e.g. an antibody which does not comprise glycosylation sites or a modified full-length antibody). For conjugation onto the acceptor glutamines within the CH2 domain, and particularly at residue Q295, antibodies will be free of N-linked glycosylation. Full-length wild-type IgG antibodies naturally comprise N-linked glycosylation at residue 297 of the heavy chain which interferes and prevents with TGase-mediated conjugation onto glutamine residues in the CH2 domain. Deglycosylation can be carried out according to any suitable method. For example, antibody in PBS buffer (PBS (10×): Weight 2.1 g $KH_2PO_4$, 90 g NaCl, 4.8 g $Na_2HPO_4 \times 2H_2O$ is transferred to a 1 L glass bottle, to which is added water to a volume of 1 L. To get PBS 1×, use 100 mL PBS (10×) and add water to a volume of 900 mL. pH is adjusted to 7.2 and filled to 1 L with water), and incubated with 6 Units/mg protein of N-glycosidase F (PNGase F) from *Flavobacterium meningosepticum* (Roche, Switzerland) overnight at 37° C. The enzyme is then removed by centrifugation-dialysis (Vivaspin MWCO 50 kDa, Vivascience, Winkel, Switzerland). The product can be analyzed by LC/MS. Alternatively, an antibody will be naturally free of N-linked glycosylation, for example as a result of an amino acid modification, e.g. at residues 297, 298 and/or 299 (EU numbering). For conjugation onto the acceptor glutamines within the CH3 domain (including on a TGase recognition tag fused to a CH3 domain) antibodies need not be free of (may comprise) N-linked glycosylation.

Once antibody and lysine-based linker substrates are prepared they can be reacted by bringing them into contact with one another in a reaction vessel in the presence of a bacterial transglutaminase (BTG) (see, e.g. EC 2.3.2.13, protein-glutamine-γ-glutamyltransferase). The BTG will capable of causing, under suitable conditions, the formation of a covalent bond between the acceptor glutamine residue of the antibody and the linking reagent (at the primary amine of the linking reagent) In one embodiment, the TGase is from *S. mobaraense*. In another embodiment, the TGase is a mutant TGase having 1, 2, 3, 4, 5, 10 or more amino acid modifications (e.g. substitutions, insertions, deletions), optionally the TGase has at least 80% sequence identity with native TGase, e.g. a TGase from *S. mobaraense*. A preferred example is recombinant bacterial transglutaminase derived from *streptomyces mobaraensis* (available from Zedira, Darmstadt, Germany).

The TGase-catalyzed reaction can be carried out under mild conditions, from several hours to a day (e.g. overnight). Recombinant BTG (EC 2.3.2.13) from *streptomyces mobaraensis* (Zedira, Darmstadt, Germany) are typically used at a concentration of between 1 and 20 U/mL. The lysine-based linker substrates are reacted with antibody (1 mg/mL) at ligand concentrations between 400 and 600 mol/L, providing a 60 to 90-fold excess of the substrates over the antibody, or optionally at lower excess of substrates, e.g. 1- to 20-fold, or 10-20 fold excess over acceptor glutamines. The reactions are performed in potassium-free phosphate buffered saline (PBS; pH 8) at 37° C. After 4 h to several days (depending on the antibody and the ligand), steady-state conditions are achieved. Excess ligand and enzyme are then removed using centrifugation-dialysis (Vivaspin MWCO 50 kDa, Vivascience, Winkel, Switzerland).

An acceptor glutamine present on an antibody (e.g. part of the antibody's primary structure, including for example an antibody fragment with a peptide tag) will, under suitable conditions, be recognized by a TGase and covalently bound to a lysine-based linker (e.g., compound of Formula I). The results is an antibody of Formula II (the acceptor glutamine is functionalized with the compound of Formula I). Resulting antibody conjugates can be analyzed using any suitable method. Preferably, the stoichiometry of the conjugated antibodies can be characterized by liquid chromatography mass spectrometry (LC/MS) using a top-down approach in order to assess the number of lysine-based linker and/or where applicable moieties-of-interest conjugated to antibodies, and in particular the homogeneity of the composition. Conjugates can be reduced before LC/MS analysis and light chains and heavy chains are measured separately.

Reaction Partners Comprising a Moiety-of-Interest Z and Reactive Group R'

Once a lysine-based linker (e.g., compound of Formula I) comprising a reactive moiety R is conjugated to an antibody (e.g., resulting in an antibody of Formula II) the antibody can be reacted with a compound comprising a moiety Z and a reactive group R', thereby forming an antibody-moiety-of-interest conjugate. Typically, the conjugated antibody (e.g. the antibody of Formula II) is subjected to a deprotection step to provide an unprotected reactive group (R) and the antibody is then reacted with a compound comprising a reaction partner R'.

R' can be, for example, a moiety comprising an unprotected or protected thiol, maleimide, halo-acetamide (e.g. bromo-acetamide, iodo-acetamide, cloro-acetamide), o-phoshenearomatic ester, azide, fulminate, alkyne, cyanide, anthracene, 1,2,4,5-tetrazine, norbornene, other stained or otherwise electronically activated alkene or, optionally, a protected or unprotected amine, so long as such group when unprotected is reactive with R (when R is unprotected).

The compounds of (e.g. Formula III) to be used in reaction with an antibody can be reacted with antibody (e.g., 1 mg/mL) at ligand concentrations between 2 and 20 (or between 4 and 20) molar equivalents to the antibody, optionally between 2 and 10 (or between 4 and 10) molar equivalents to the antibody, optionally at a less than, or about, 20, 10, 5, 4 or 2 molar equivalents to the antibody. However it will be appreciated that higher excesses (equivalents of reaction partner (e.g. Formula III) to antibody (40 to 80 fold, 60 to 90-fold) can also be used.

The compounds of Formula III to be used in reaction with an antibody conjugated to a lysine-based linker (but without a moiety-of-interest), e.g, an antibody of Formula II, as well as the resulting antibody conjugates therefore comprise one or more moieties-of-interest Z. The compounds of Formula III may additionally comprise a moiety V and/or Y, typically depending on which elements are included in the lysine-based linker.

The compounds of Formula III to be used in reaction with an antibody conjugated to a lysine-based linker (e.g. an antibody of Formula II) will comprise moieties Z connected to linker L' when Y' and V' are absent, connected to the spacer system Y' or, when Y' is absent, connected to V'. Consequently, a compound of Formula III may comprise a moiety Z connected to or comprising a reactive group R', optionally the moiety Z connected to a reactive group R' via a spacer system Y' or, when Y' is absent, to a reactive group R' via V', or to a reactive group R' via a V'—Y', wherein Z is preferably connected to Y' and V' is connected to R' and Y'.

A compound of Formula III may contain one, two or more Z moieties that are the same or that differ from one another, e.g. different therapeutic moieties, and/or diagnostic moieties.

In one embodiment, the antibody of Formula II is reacted with a compound of Formula III comprising a moiety of interest Z comprising and a reactive group R' capable of forming a bond with reactive group R of Formula I or II, optionally wherein the compound further comprises a V' and/or Y' group. The compound comprising a moiety of interest Z comprising and a reactive group R' preferably comprises a structure of Formula III, below,

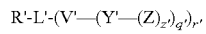

R'-L'-(V'—(Y'—(Z)$_{z'}$)$_{q'}$)$_{r'}$     Formula III where:

R' is a reactive group, e.g. a reactive group complementary for forming at least one bond with reactive group R of Formula I or II;

L' is independently absent, a bond or a continuation of a bond, or a carbon comprising framework of 5 to 200 atoms substituted at one or more atoms, optionally, wherein the carbon comprising framework comprises a linear framework of 5 to 30 carbon atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

V' is independently absent, a non-cleavable moiety or a conditionally-cleavable moiety, optionally following prior conditional transformation, which can be cleaved or transformed by a chemical, photochemical, physical, biological, or enzymatic process, cleavage of V ultimately leading to release of one or more Z moieties. In some embodiments, V is, preferably, a di-, tri-, tetra-, or oligopeptide as described below in the section entitled "The V Moiety", Y' is independently absent or a spacer system (e.g., a self-eliminating spacer system or a non-self-elimination spacer system) which is comprised of 1 or more spacers, Z is independently a reactive group (optionally protected) other than a complementary reactive group for reaction with R', a moiety that improves the pharmacokinetic properties, a therapeutic moiety, or diagnostic moiety;

q' and r' are an integer selected from among 1, 2, 3 or 4, representing degree of branching; and z' is an integer selected from among 1, 2, 3 or 4.

Where Z is a reactive group, it can be a moiety comprising an unprotected or protected thiol, maleimide, haloacetamide, o-phoshenearomatic ester, azide, fulminate, alkyne, cyanide, anthracene, 1,2,4,5-tetrazine, norbornene, other stained or otherwise electronically activated alkene or, optionally, a protected or unprotected amine when X is absent and L, V, or Y is other than a bond or a continuation of a bond. In an alternative embodiment Z can be a reactive moiety, preferably a moiety comprising an unprotected or protected thiol, an unprotected or protected amine, maleimide, haloacetamide, o-phoshenearomatic ester, azide, fulminate, alkyne, cyanide, anthracene, 1,2,4,5-tetrazine, norbornene, other stained or otherwise electronically activated alkene. Preferably R is not an amine when n=5 and X, L, V and Y are absent. Preferably R is not an amine when n=4 and X, L, V and Y are absent.

The moiety R' is connected to Z, or optionally to Z via V' and/or Y' and is able to react with a suitable functional group R on a reaction partner, e.g. group R on the lysine-based linker of formula I or II. As discussed above, when the reactive moiety R' is designed to react with a reactive group R, a compound of Formula Ib or IV is formed.

The L' group can be a carbon comprising framework, where L is a symmetrically or asymmetrically branched hydrocarbon, monosaccharide, disaccharide, oligosaccharide, other natural oligomer, dimer, trimer, or higher oligomer resulting from any chain-growth or step-growth polymerization process, wherein L' has r', q', and/or z' sites of attachment for the respective V', Y', and R' groups, where r' and q' represent the degree of branching or polymerization. The sites of attachment can comprise a bond or comprise a functional group selected from an alkene, alkyne, ether, thioether, ester, thioester, amine, amide, alkylamide, or other functional group readily generated by a condensation or addition reaction.

The linking group (RR') in M of compounds of Formula (Ib) and (IV) represents the R' addition product of a reactive moiety R' and a reactive moiety R. This group then links the moiety Z (e.g. comprised in the compound of Formula II) with L, V or Y, preferably via (RR') of M is L', V', and/or Y'. The group that remains may be a bond. Typically, however, L', V', and/or Y' is a linking group. RR' can be an addition product of a: thio-maleimide (or haloacetamide) addition, for example, a N,S-disubstituted-3-thio-pyrrolidine-2,5-dione; Staudinger ligation, for example, a N,3- or N,4-substituted-5-dipenylphosphinoxide-benzoic amide; Huisgen 1,3-cycloaddition (click reaction), for example, a N,S-disubstituted-3-thio-pyrrolidine-2,5-dione, 1,4-disubstituted-1,2,3-triazole, 3,5-disubstituted-isooxazole, or 3,5-disubstituted-tetrazole; Diels-Alder cycloaddition adduct, for example the 2,4-cycloaddition product between an O or N-substituted-5-norbornene-2-carboxylic ester or amide, N-substituted-5-norbornene-2,3-dicarboxylic imide, O or N-substituted-7-oxonorbornene-5-carboxylic ester or amide, or N-substituted-7-oxonorbornene-5,6-dicarboxylic imide and a 9-substituted anthracene or 3-substituted 1,2,4,5-tetrazine; or any high yield selective amidation or imidization reaction. Some reactions and the RR' reaction products are illustrated in FIGS. 1 and 2. A compound of Formula II can be reacted with a compound for Formula III to obtain a compound of Formula IV.

The step of reacting an antibody having a lysine-based linker (e.g., compound of Formula I) comprising a reactive moiety R conjugated thereto with a compound comprising a moiety Z and a reactive group R' to form an antibody-moiety-of-interest conjugate can advantageously be carried out by binding the antibody onto a solid support. Use of a solid support for this step can allow for antibody samples of different initial concentrations and amounts to be reacted and then compared for activity. Use of a solid support also permits improved purification of functionalized antibodies. Finally, use of a solid support for this step allows an increase in efficiency in production and/or increase in completion of reactions because the compound comprising a moiety Z and a reactive group R' can be recovered and then reintroduced to the solid support; this may reduce loss of expensive reagents such as cytotoxic drugs.

The amount of antibody used in solid-support based methods may be small amounts (e.g., 1 to 500 μg) of antibody.

Generally, the solid support may be any suitable insoluble, functionalized material to which the antibodies can be reversibly attached, either directly or indirectly, allowing them to be separated from unwanted materials, for example, excess reagents, contaminants, and solvents. Examples of solid supports include, for example, functionalized polymeric materials, e.g., agarose, or its bead form Sepharose®, dextran, polystyrene and polypropylene, or mixtures thereof; compact discs comprising microfluidic channel structures; protein array chips; pipet tips; membranes, e.g., nitrocellulose or PVDF membranes; and microparticles, e.g., paramagnetic or non-paramagnetic beads. In some embodiments, an affinity medium will be bound to the solid support and the antibody will be indirectly attached to solid support via the affinity medium. In one aspect, the solid support comprises a protein A affinity medium or protein G affinity medium. A "protein A affinity medium" and a "protein G affinity medium" each refer to a solid phase onto which is bound a natural or synthetic protein comprising an Fc-binding domain of protein A or protein G, respectively, or a mutated variant or fragment of an Fc-binding domain of protein A or protein G, respectively, which variant or fragment retains the affinity for an Fc-portion of an antibody.

The present methods can comprise a step of immobilizing an antibody comprising a lysine-based linker (e.g., compound of Formula I) comprising a reactive moiety R conjugated thereto on a solid support to provide an immobilized antibody. In some embodiments, the solid support will have the capacity to bind more antibody than the amount present in the antibody-containing sample or, in other words, the amount of antibody bound to the solid support following the immobilization step will be less than the capacity of the solid support. Because the samples generally vary with respect to antibody quantity, there will be corresponding variability in the amount of immobilized antibody from one sample as compared to another.

It will be possible to optionally limit the quantity of bound antibody and the solid support will only have the capacity to bind up to a certain amount of antibody (e.g., up to 5 μg, up to 10 μg, or up to 15 μg of protein). In these embodiments, although there will be a limit as to the maximum amount of antibody that can be bound to the solid support, there may still be variability in the amount of immobilized antibody in one sample as compared to another. This is because one or more of the samples might contain a small quantity of antibody, less than the maximum loading capacity of the solid support. One approach for preparing a solid support that has limited capacity for binding antibody is to make a very low-capacity resin such that a larger volume of resin slurry (20 uL for example) contains only enough capacity to bind 5 ug of antibody. An alternative approach is to reduce the effective capacity of a resin by diluting the resin with an appropriate volume of non-functionalized resin. For example, a protein G-sepharose resin with a binding capacity of 20 ug/uL could be converted to a mixed resin with an effective binding capacity of 0.5 ug/uL by mixing 1 part of protein G-sepharose with 40 parts unfunctionalized sepharose. In performing such a resin dilution, in some embodiments, the diluent will be a resin which is constructed from the same base material as the affinity resin, has pore sizes small enough to exclude antibodies, and lacks any surface functionality which may interact with antibodies or the chemical reagents used to prepare antibody conjugates.

Antibodies are generally immobilized on a solid support by the step of applying an antibody-containing sample to a solid support. If desired, a washing step can be performed following immobilization to separate the immobilized antibodies from the cell culture supernatant or other components of the antibody-containing samples.

Once the antibodies are immobilized on the solid support, the conjugated antibody (e.g. the antibody of Formula II) is typically subjected to a deprotection step to provide an unprotected reactive group (R) and the antibody is then reacted with a compound comprising a reaction partner R'. A reaction step is then performed comprising applying a compound comprising a moiety Z and a reactive group R' (e.g. a compound of Formula III) to a solid support to generate an antibody-moiety-of-interest conjugate (e.g., antibody of Formula IV).

In some embodiments, the compound comprising a moiety Z and a reactive group R' will be provided in molar excess (molar excess as to the reactive groups (R)).

After contacting the reduced antibodies with the appropriate amount compound comprising reactive group (R'), a washing step can be performed to remove any unreacted materials. Optionally, unreacted compound comprising a moiety Z and a reactive group R' is recovered; optionally, unreacted compound is re-applied to the solid support to provide for higher completion of the reaction between antibody comprising reactive group (R) and compound comprising reactive group (R').

Subsequently, the immobilized antibody conjugates can be eluted from the solid support to provide antibody conjugate compositions. Methods of eluting proteins from solid supports are known in the art and the skilled practitioner will be able to select an appropriate buffer for elution. For example, in embodiments, where the solid support comprises protein A or protein G resin, the antibody conjugates can be eluted with standard low pH buffers for elution from protein A or protein G columns.

The Moiety Z

The moiety Z can be connected to Y or Y' or, when absent, to V or V', optionally via R or RR', with any suitable atom. In one embodiment, Z is coupled via oxygen (from for example a hydroxyl group or carboxyl group), carbon (from for example a carbonyl group), nitrogen (from for example a primary or secondary amino group), or sulfur (from for example a sulfhydryl group). In one embodiment, Z is coupled via a group such that its therapeutic abilities or diagnostic characteristics are, at least partly, blocked or masked. In case a compound is to be used for treating or preventing disease in an animal, e.g., a mammal, the Z moieties are generally therapeutic moieties. In case a compound is used to make a diagnosis or used in an ex vivo or in vivo diagnostic assay, the Z moieties are generally diagnostic moieties, for example chromogenic, fluorogenic, phosphorogenic, chemiluminescent, or bio luminescent compounds.

In one embodiment, the Z moiety is compound, preferably an organic compound, having a molecular weight of at least 300 g/mol, 400 g/mol, 500 g/mol, 600 g/mol, 700 g/mol, 800 g/mol, 900 g/mol, 1,000-g/mol or 2,000 g/mol.

In one embodiment, the Z moiety is a chemical compound displaying hydrophobic properties, optionally additionally having a molecular weight of at least 300 g/mol, 400 g/mol, 500 g/mol, 600 g/mol, 700 g/mol, 800 g/mol, 900 g/mol. 1,000 g/mol or 2,000 g/mol. Hydrophobic character may be determined, for example, by decreased water solubility, decreased polarity, decreased potential for hydrogen bonding, and/or an increased oil/water partition coefficient. The presently disclosed methods produce antibody conjugates with hydrophobic drugs (the latter being the Z moiety). As used herein, the term "hydrophobic" is a physical property of a molecule that is repelled from a mass of water. Hydrophobic compounds can be solubilized in nonpolar solvents, including but not limited to, organic solvents. Hydrophobicity can be conferred by the inclusion of apolar or nonpolar chemical groups that include, but are not limited to, saturated and unsaturated aliphatic hydrocarbon groups and such groups substituted by one or more aromatic, cycloaliphatic or heterocyclic group(s). Conversely, "hydrophilic" molecules are capable of hydrogen bonding with a water molecule and are therefore soluble in water and other polar solvents. The terms "hydrophilic" and "polar" can be used interchangeably. Hydrophilic characteristics derive from the presence of polar or charged groups, such as carbohydrates, phosphate, carboxylic, sulfato, amino, sulfhydryl, nitro, hydroxy and other like groups.

Hydrophobic molecules are poorly water soluble, for example, having a solubility of less than about 10 mg/ml. In some embodiments, the hydrophobic compound can have a solubility of less than about 1 mg/ml in water. In other embodiments, the hydrophobic compound has a solubility in water of less than about 50, μg/ml, 10 μg/ml, and in particular embodiments, about 1 μg/ml or 2.5 μg/ml. In other embodiments, the hydrophobic compound can have a solubility of about 0.001 μg/ml to about 10 mg/ml, including but not limited to 0.001 μg/ml, 0.01 μg/ml, 0.1 μg/ml, 1 μg/ml, 2 μg/ml, 5 μg/ml, 10 μg/ml, 50 μg/ml, 100 μg/ml, 500 μg/ml, 1 mg/ml, 5 mg/ml, and 10 mg/ml, and any other concentration between 0.001 μg/ml and 10 mg/ml.

Representative, non-limiting examples of drugs that can be formulated using the presently disclosed methods include taxanes, e.g. paclitaxel (PTX), and camptothecin (CPT), maytansanoids, duocarmycins, dolastatins and auristatins. Such drugs are poorly soluble in water, e.g. PTX has a solubility in water of less than about 1 μg/ml, CPT has a water solubility of about 2.5 μg/ml.

In one embodiment, the Z moiety is a chemical compound having a negative charge, optionally additionally displaying hydrophobic properties and/or having a molecular weight of at least 300 g/mol, 400 g/mol, 500 g/mol, 600 g/mol, 700 g/mol, 800 g/mol, 900 g/mol, 1,000 g/mol or 2,000 g/mol.

When more than one Z moiety is connected to a self-elimination spacer system Y or Y', at least one Z should be released upon self-elimination of Y or Y'. The moiety Z initially released may be a moiety that is not a fully active moiety itself. In other words, Z may be a moiety that has limited diagnostic or therapeutic abilities, e.g. a moiety that acts as a prodrug. Such a Z moiety may require further processing or metabolism, e.g., hydrolysis, enzymatic cleavage, or enzymatic modification (for example phosphorylation, reduction, or oxidation) in order to become fully active. In one embodiment, such further processing is intentionally designed for Z to for example allow Z to reach its final target or cross a biological barrier, e.g., a cell membrane or a nuclear membrane, before it is fully activated. Z may for example contain a hydrophobic moiety that enables Z to cross a cell membrane. This hydrophobic moiety may then be hydrolyzed or removed in any other way intracellularly.

In one aspect, a Z moiety may be a backbone (e.g. polymer) to which a plurality of drugs or diagnostic moieties are linked. For example, Z may be a polyacetal- or polyacetal derivative-based polymer comprising a plurality of drug molecules, see, e.g., Yurkovetskiy et al. (2004) Mol. Pharm. 1(5): 375-382 and WO 2011/120053, the disclosures of which are incorporated herein by reference; for example Z may be a polymer compound of Formula I of WO 2011/120053 comprising a plurality of cytotoxic anti-cancer agents.

In one aspect, one or more moieties Z are each selected from a therapeutic or diagnostic agent.

In another embodiment, one or more moieties Z are each a therapeutic agent. In another embodiment, all moieties Z are each a therapeutic agent.

In yet another embodiment, the moieties Z each are the same therapeutic moiety.

In yet another embodiment, the moieties Z comprise at least two different therapeutic moieties.

The moiety Z includes, for example, antineoplastic agents, drugs, toxins (such as enzymatically active toxins of bacterial or plant origin and fragments thereof e.g. ricin and fragments thereof) biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

In one embodiment, the one or more moieties Z are each independently chosen from an antibiotic, an anti-bacterial agent, an antimicrobial agent, an anti-inflammatory agent, an anti-infectious disease agent, an anti-autoimmune disease agent, an anti-viral agent, or an anticancer agent, preferably a cytotoxic anti-cancer agent.

In another embodiment, the one or more moieties Z are each an anticancer agent. In a further embodiment, the one or more moieties Z are each a hydroxyl-containing anticancer agent.

In one embodiment, Z is an alkylating agent, preferably a DNA alkylating agent. An alkylation agent is a compound that can replace a hydrogen atom with an alkyl group under physiological conditions (e.g. pH 7.4, 37 C, aqueous solution). Alkylation reactions are typically described in terms of substitution reactions by N, O and S heteroatomic nucleophiles with the electrophilic alkylating agent, although Michael addition reactions are also important. Examples of alkylating agents include nitrogen and sulfur mustards, ethylenimines, methanosulfonates, CC-1065 and duocarmycins, nitrosoureas, platinum-containing agents, agents that effectuate Topoisomerase II-mediated site dependent alkylation of DNA (e.g. psorospermin and related bisfuranoxanthones), ecteinascidin and other or related DNA minor groove alkylation agents.

In one embodiment, Z is a DNA minor groove binding and/or alkylating agent, e.g., a pyrrolobenzodiazepine, a duocarmycin, or derivatives thereof.

In a further embodiment, the one or more moieties Z are each independently selected from the group consisting of taxanes, anthracyclines, camptothecins, epothilones, mytomycins, combretastatins, vinca alkaloids, nitrogen mustards, maytansinoids, calicheamycins, duocarmycins, tubulysmes, dolastatins and auristatins, enediynes, pyrrolobenzodiazepines, ethylenimines, radioisotopes, therapeutic proteins and peptides, and toxins or fragments thereof.

In a further embodiment, the one or more moieties Z are each independently selected from cyclophosphamide, ifosfamide, chlorambucil, 4-(bis(2-chloroethyl)amino)phenol, 4-(bis(2-fluoroethyl)amino)phenol, N,N-bis(2-chloroethyl)-p-phenylenediamine, N,N-bis(2-fluoro-ethyl)-p-phenylenediamine, carmustine, lomustine, treosulfan, dacarbazine, cisplatin, carboplatin, vincristine, vinblastine, vindesine, vinorelbine, paclitaxel, docetaxel, etoposide, teniposide, topotecan, inirotecan, 9-aminocamptothecin, 9-nitrocamptothecin, 10-hydroxycamptothecin, lurtotecan, camptothecin, crisnatol, mitomycin C, mitomycin A, methotrexate, trimetrexate, mycophenolic acid, tiazofurin, ribavirin, hydroxyurea, deferoxamine, 5-fluorouracil, floxuridine, doxifluridine, raltitrexed, cytarabine, cytosine arabinoside, fludarabine, 6-mercaptopurine, thioguanine, raloxifen, megestrol, goserelin, leuprolide acetate, flutamide, bicalutamide, vertoporfin, phthalocyanine, photosensitizer Pc4, demethoxy-hypocrellin A, interferon-alpha, interferon-gamma, tumor necrosis factor, lovastatin, staurosporine, actinomycin D, bleomycin A2, bleomycin B2, peplomycin, daunorubicin, doxorubicin, N-(5,5-diacetoxypentyl)doxorubicin, morpholino doxorubicin, idarubicin, epirubicin, pirarubicin, zorubicin, mitoxantrone, thapsigargin, $N^8$-acetyl-spermidine, tallysomycin, esperamycin, butyric acid, retinoic acid, 1,8-dihydroxybicyclo[7.3.1]trideca-4-ene-2,6-diyne-13-one, anguidine, podophyllotoxin, combretastatin A-4, pancratistatin, carminomycin, streptonigrin, elliptmium acetate, maytansine, maytansinol, calicheamycin, mertansine (DM1), N-acetyl-$\gamma_1^I$-calicheamycin, calicheamycin-$\gamma_1^I$, calicheamycin-$\alpha_2^I$, calicheamycin-$\alpha_3^I$, duocarmycin SA, duocarmycin A, CC-1065, CBI-TMI, duocarmycin C2, duocarmycin B2, centanamycin, dolastatin, auristatin E, monomethylauristatin E (MMAE), monomethylauristatin F (MMAF), and derivatives thereof.

Chelated metals include chelates of di- or tripositive metals having a coordination number from 2 to 8 inclusive. Particular examples of such metals include technetium (Tc), rhenium (Re), cobalt (Co), copper (Cu), gold (Au), silver (Ag), lead (Pb), bismuth (Bi), indium (In), gallium (Ga), yttrium (Y), terbium (Tb), gadolinium (Gd), and scandium (Sc). In general the metal is preferably a radionuclide. Particular radionuclides include $^{99m}$Tc, $^{186}$Re, $^{188}$Re, $^{58}$Co, $^{60}$Co, $^{67}$Cu, $^{195}$Au, $^{199}$Au, $^{110}$Ag, $^{203}$Pb, $^{206}$Bi, $^{207}$Bi, $^{111}$In, $^{67}$Ga, $^{68}$Ga, $^{88}$Y, $^{90}$Y, $^{160}$Tb, $^{153}$Gd and $^{47}$Sc.

The chelated metal may be for example one of the above types of metal chelated with any suitable polydentate chelating agent, for example acyclic or cyclic polyamines, polyethers, (e.g. crown ethers and derivatives thereof); polyamides; porphyrins; and carbocyclic derivatives.

In general, the type of chelating agent will depend on the metal in use. One particularly useful group of chelating agents in conjugates, however, are acyclic and cyclic polyamines, especially polyaminocarboxylic acids, for example diethylenetriaminepentaacetic acid and derivatives thereof, and macrocyclic amines, e.g. cyclic tri-aza and tetra-aza derivatives (for example as described in PCT publication no. WO 92/22583); and polyamides, especially desferriox-amine and derivatives thereof.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

Synthetic or naturally occurring polymers for use as effector molecules include, for example optionally substituted straight or branched chain polyalkylene, polyalkenylene, or polyoxyalkylene polymers or branched or unbranched polysaccharides, e.g. a homo- or hetero-polysaccharide such as lactose, amylose, dextran or glycogen.

Particular optional substituents which may be present on the above-mentioned synthetic polymers include one or more hydroxy, methyl or methoxy groups. Particular examples of synthetic polymers include optionally substituted straight or branched chain poly(ethyleneglycol), poly(propyleneglycol), poly(vinylalcohol) or derivatives thereof, especially optionally substituted poly(ethyleneglycol) such as methoxypoly(ethyleneglycol) or derivatives thereof. Such compounds, when used as a moiety Z can be employed as a moiety that improves the pharmacokinetic properties of the antibody.

The size of the polymer may be varied as desired, but will generally be in an average molecular weight range from 500 Da to 50,000 Da, preferably from 5,000 to 40,000 Da and more preferably from 10,000 to 40,000 Da and 20,000 to 40,000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumor, it may be advantageous to use a small molecular weight polymer, for example with a molecular weight of around 5,000 Da. For applications where the product remains in the circulation, it may be advantageous to use a higher molecular weight polymer, for example having a molecular weight in the range from 20,000 Da to 40,000 Da.

Particularly preferred polymers include a polyalkylene polymer, such as a poly(ethyleneglycol) or, especially, a methoxypoly(ethyleneglycol) or a derivative thereof, and especially with a molecular weight in the range from about 10,000 Da to about 40,000 Da.

In another embodiment, z' equals 1, each V, Y or V—Y (including whether any V and Y is a V' or Y') moiety contains a single attachment site for a functional group of Z.

In another embodiment, a one V (or V'), Y, (or Y') or V—Y (or V'—Y', V—Y') moiety is attached to more than one Z moiety via multiple functional groups R on the said V, Y or V—Y moiety. Optionally, the one or more V (or V') moieties comprise a polymer, optionally an oligoethylene glycol or a polyethylene glycol or a derivative thereof.

Antibody-Z Conjugates

The antibody conjugates resulting from the reaction of the compounds of Formula Ib or III with an antibody conjugated to a lysine-based linker will yield an antibody conjugate in which a moiety Z is connected to linker L (or L') when Y (or Y') and V (or V') are absent, to the spacer system Y (or Y') or, when Y (or Y') is absent, to V (or V). Optionally said connections are via linking group (RR') of M.

The conjugates resulting from the reaction yield an antibody (Ab) which is conjugated (i.e., covalently attached) via an acceptor glutamine residue (Q) present on the antibody to a NH group of a lysine-based linker, and one or more moieties (Z) through optional linking group (RR'), optional linker (V or V') and/or optional spacer (Y or Y').

In one embodiment, the (RR') remain present in a conjugated antibody, in which case a Formula IVa will comprise an M moiety. Such an antibody comprises a functionalized glutamine residue (Q) of Formula IV, below,

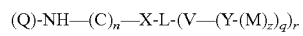

$$(Q)\text{-NH}—(C)_n—X\text{-}L\text{-}(V—(Y\text{-}(M)_z)_q)_r \qquad \text{Formula IVa}$$

where:
Q is glutamine residue present in an antibody;
$(C)_n$ is a substituted or unsubstituted alkyl or heteroalkyl chain, optionally wherein any carbon of the chain is substituted with an alkoxy, hydroxyl, alkylcarbonyloxy, alkyl-S—, thiol, alkyl-C(O)S—, amine, alkylamine, amide, or alkylamide;
n is an integer selected from among the range of 2 to 20;
X is NH, O, S, or absent;
L is independently absent, a bond or a continuation of a bond, or a carbon comprising framework of 5 to 200 atoms substituted at one or more atoms, optionally, wherein the carbon comprising framework comprises a linear framework of 5 to 30 carbon atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;
r is an integer selected from among 1, 2, 3 or 4;
q is an integer selected from among 1, 2, 3 or 4;
z is an integer selected from among 1, 2, 3 or 4; and
V is independently absent, a non-cleavable moiety or a conditionally-cleavable moiety, optionally following prior conditional transformation, which can be cleaved or transformed by a chemical, photochemical, physical, biological, or enzymatic process (e.g. cleavage of V ultimately leading to release of one or more moieties subsequently or ultimately linked to V, for example a Z moiety). In some embodiments, V is, preferably, a di-, tri-, tetra-, or oligopeptide as described below in the section entitled "The V Moiety";
Y is independently absent or a spacer (e.g., a self-eliminating spacer system or a non-self-elimination spacer system) which is comprised of 1 or more spacers; and
M is independently: R or (RR')-L'-(V'—(Y'—(Z)$_{z'}$)$_{q'}$)$_{r'}$, wherein each of L', V', Y', z', q', and r' are as defined in Formula III (or are defined as L, V, Y, z, q and r, respectively, Z is a moiety-of-interest, optionally a moiety that improves the pharmacokinetic properties, or a therapeutic moiety or a diagnostic moiety, R is as defined in Formula I and wherein each (RR') is an addition product between an R of Formula I and its complementary R' of Formula III (see, for example, FIG. 1 and FIG. 2).

Thus, RR' can be for example an addition product of a thio-maleimide (or haloacetamide) addition, for example, a N,S-disubstituted-3-thio-pyrrolidine-2,5-dione; Staudinger ligation, for example, a N,3- or N,4-substituted-5-dipenyl-phosphinoxide-benzoic amide; Huisgen 1,3-cycloaddition (click reaction), for example, a N,S-disubstituted-3-thiopyrrolidine-2,5-dione, 1,4-disubstituted-1,2,3-triazole, 3,5-disubstituted-isooxazole, or 3,5-disubstituted-tetrazole; Diels-Alder cycloaddition adduct, for example the 2,4-cycloaddition product between an O or N-substituted-5-norbornene-2-carboxylic ester or amide, N-substituted-5-norbornene-2,3-dicarboxylic imide, O or N-substituted-7-oxonorbornene-5-carboxylic ester or amide, or N-substituted-7-oxonorbornene-5,6-dicarboxylic imide and a 9-substituted anthracene or 3-substituted 1,2,4,5-tetrazine; or any high yield selective amidation or imidization reaction. Some reactions and the corresponding RR' reaction products are illustrated in FIGS. 1 and 2.

While the use of Formula Ia linkers with reactive groups is convenient, in one variation of Formula IV, a linker can be constructed in which the (RR') are not present by reacting an antibody comprising an acceptor glutamine with a linking reagent of Formula Ic. Such an antibody may comprise a functionalized glutamine residue (Q) of Formula IVb, below,

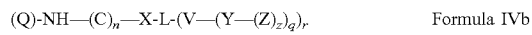

(Q)-NH—(C)$_n$—X-L-(V—(Y—(Z)$_z$)$_q$)$_r$,  Formula IVb where:

Q is glutamine residue present in an antibody;

(C)$_n$ is a substituted or unsubstituted alkyl or heteroalkyl chain, optionally wherein any carbon of the chain is substituted with an alkoxy, hydroxyl, alkylcarbonyloxy, alkyl-S—, thiol, alkyl-C(O)S—, amine, alkylamine, amide, or alkylamide;

n is an integer selected from among the range of 2 to 20;

X is NH, O, S, or absent;

L is independently absent, a bond or a continuation of a bond, or a carbon comprising framework of 5 to 200 atoms substituted at one or more atoms, optionally, wherein the carbon comprising framework comprises a linear framework of 5 to 30 carbon atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

r an integer selected from among 1, 2, 3 or 4;

q an integer selected from among 1, 2, 3 or 4;

z an integer selected from among 1, 2, 3 or 4; and

V is independently absent, a non-cleavable moiety or a conditionally-cleavable moiety, optionally following prior conditional transformation, which can be cleaved or transformed by a chemical, photochemical, physical, biological, or enzymatic process (e.g. cleavage of V ultimately leading to release of one or more moieties subsequently or ultimately linked to V, for example a Z moiety). In some embodiments, V is, preferably, a di-, tri-, tetra-, or oligo-peptide as described below in the section entitled "The V Moiety";

Y is independently absent or a spacer (e.g., a self-eliminating spacer system or a non-self-elimination spacer system) which is comprised of 1 or more spacers; and Z is a moiety-of-interest, optionally a moiety that improves the pharmacokinetic properties, or a therapeutic moiety or a diagnostic moiety. Preferably, Z is a cytotoxic anti-cancer agent, e.g. a compound selected from the group consisting of taxanes, anthracyclines, camptothecins, epothilones, mytomycins, combretastatins, vinca alkaloids, nitrogen mustards, maytansinoids, calicheamycins, duocarmycins, tubulysmes, dolastatins and auristatins, enediynes, radioisotopes, therapeutic proteins and peptides, and toxins or fragments thereof.

Generally, each Z is directly coupled to either Y or V when Y is absent, or L when both Y and V are absent.

Optionally, the antibody conjugate comprises a group (RR') representing the remainder of a reactive moiety R when R has reacted with a reactive moiety R', wherein the group (RR') connects (a) an L to a Z, a V or a Y, (b) a V to a Z or a Y, or (c) a Y to a Z. For example, any V, Y and/or Z may be characterized as comprising a (RR') group. Any L, V, Y may be an L', V' or Y', respectively.

It will be appreciated that Formula IVa or IVb can for convenience also be expressed as (Ab)-NH—(C)$_n$—X-L-(V—(Y-(M/Z)$_z$)$_q$)$_r$, where (Ab) is an immunoglobulin (Ab) is conjugated via a glutamine (Q) residue to an NH of the linking reagent (e.g the compound of Formula I).

Evaluating the Antibodies

Once antibody conjugates (i.e. as antibody samples comprising antibody conjugates) have been obtained, they will generally be assessed for a characteristic of interest. In some embodiments, activity assays and/or other assays will be performed in order to characterize the antibody conjugates. In some embodiments, cell binding, affinity, and/or cytotoxicity assays will be performed. The characteristic that is assessed can be a property mediated by the variable region of the antibody, the constant region of the antibody and/or by the moiety-of-interest (Z).

In one example, the antibody conjugates can be assessed (e.g. compared) for their ability to inhibit the proliferation of, or, preferably, kill, target cells, e.g. using a cytotoxicity assay. Particularly, where moiety Z is a cytotoxic drug, the efficacy of the antibody as antibody-drug conjugates can be evaluated, e.g. as the ability of the antibodies to cause the death of tumor cells, infected cells, or generally any suitable target cells that express the antigen for which the antibody is specific.

In other example, moiety Z is a moiety that improves the pharmacokinetic properties of the antibody, and the pharmacokinetic properties of the antibody can be evaluated. In one embodiment, the pharmacokinetic property evaluated is stability of the antibody in a suitable environment, e.g. blood, pharmaceutical formulation, etc.

It will be appreciated that the antibodies conjugated to a moiety Z can be evaluated for any suitable pharmacokinetic property, irrespective of whether the moiety Z is a moiety that improves the pharmacokinetic properties of the antibody. For example, conjugation to an antibody of a large drug will affect the pharmacokinetic properties of the antibody. Thus, antibodies may be screened for any suitable pharmacokinetic property evaluated, e.g. aggregation of antibodies in formulation, stability of the antibody conjugate in an environment of interest, e.g. blood, pharmaceutical formulation, etc. In one embodiment, the method of evaluating antibodies is a method of evaluating and/or selecting antibodies conjugated to a moiety (Z) having a lower propensity to aggregate in solution, e.g. a pharmaceutical formulation.

Irrespective of the particular moiety Z, the antibody conjugates can be assessed (e.g. compared) for their ability to interact with and/or affect the activity of a target molecule (e.g. a predetermined antigen, a polypeptide). For example the antibody conjugates can be assessed for their ability to act as an agonist or antagonist of a target molecule. Exemplary target molecules include cell surface or soluble (poly) peptides. Binding, agonist or antagonist activity can be assessed by directly monitoring such binding or signaling activity, or can be assessed by any suitable indirect assay (e.g. effects on a cell or organism).

In general, well-known assays for detecting antibody binding to antigens, including competition-based assays, ELISAs, radioimmunoassays, Western blotting, BIACORE-based assays, and flow cytometry assays, can be equally applied to detect the interaction of antibodies, such as cytotoxic antibodies, with their target cells. Typically, target cells will be tumor or cancer cells. Assessing the ability of the antibodies to inhibit the proliferation of, or, preferably, kill, target cells can be carried out using methods known in the art. For example, cell viability assays can be used to determine the cytotoxic effect of an ADC on a cell. See, for example, U.S. Pat. Nos. 7,659,241 and 7,498,298, each of which is incorporated herein in its entirety. In one embodiment, target cells (e.g. tumor or cancer cells, cells made to express a polypeptide specifically bound by an antibody) are introduced into plates, e.g., 96-well plates, and exposed to various amounts of the relevant antibodies. By adding a vital dye, i.e. one taken up by intact cells, such as AlamarBlue (BioSource International, Camarillo, Calif.), and washing to remove excess dye, the number of viable cells can be measured by virtue of the optical density (the more cells killed by the antibody, the lower the optical density). (See, e.g., Connolly et al. (2001) J Pharm Exp Ther 298:25-33, the disclosure of which is herein incorporated by reference in its entirety). Any other suitable in vitro cytotoxicity assay, assay to measure cell proliferation or survival, can equally be used, as can in vivo assays, e.g. administering the antibodies to animal models, e.g., mice, containing target cells expressing the relevant polypeptide bound by the antibody, and detecting the effect of the antibody administration on the survival or activity of the target cells over time. Also, where the antibody cross-reacts with a non-human polypeptide, e.g., a primate or murine ortholog, the antibodies can be tested on polypeptides or cells from such organism, for example to assess the ability of the antibody to bind to and/or kill target cells from the animal that expresses the relevant polypeptide, or to assess the ability of the antibody to cause side effects or other undesired biological effects in the animal that expresses the relevant polypeptide.

Any antibody, preferably a human-suitable antibody, e.g. a cytotoxic antibody, can be selected that can detectably kill, slow, stop, or reverse the proliferation of target cells, in vitro or in vivo. Preferably, the antibody is capable of stopping the proliferation (e.g., preventing an increase in the number of cells in vitro or in vivo expressing the relevant polypeptide), and most preferably the antibody can reverse the proliferation, leading to a decrease in the total number of such cells. In certain embodiments, the antibody is capable of producing a 10%, 20%, 30%, 40%, 50%, 60%, 70%, 80%, 90%, 95%, 96%, 97%, 98%, 99%, or 100% decrease in the number of cells expressing the targeted polypeptide.

In some embodiments, it will be desirable to determine the quantity of antibody conjugate in the antibody conjugate compositions, e.g. the actual quantity or relative quantity of antibody conjugate in a plurality of samples. Many methods for determining protein quantity are known in the art and can be used herein. In some embodiments, an absorbance assay will be used to determine antibody concentration. In embodiments where a fluorophore is part of the antibody conjugate, antibody concentration can be determined using a fluorescence assay. In embodiments where fluorescence is used for protein quantitation, a standard may be necessary to convert the raw fluorescence values into a concentration. Methods of using fluorescence and generating standard curves to determine protein concentration are known in the art.

The methods described herein for making antibody conjugates allow for comparisons to be made between a plurality of antibodies, including antibodies of varying concentration and optionally unknown quantity. The methods described herein for making antibody conjugates allow for a selection of antibodies with desirable characteristics when starting with, for example, a panel of antibodies resulting from a hybridoma fusion. Preferably, the antibody samples evaluated in the methods have narrow distributions of numbers of conjugates per antibody that result from the method for conjugating a moiety of interest (Z) to an antibody. In particular, provided are tetrameric (e.g. full-length) antibody compositions having a well defined distribution of number of conjugates per antibody, and in particular, a narrow Drug-Antibody Ratio (DAR) distribution. Stiochiometrically uniform drug loading between samples that allows for relevant comparisons to be made between samples. Failure to ensure stiochiometrically uniform loading levels, could, for example, lead to erroneous results from a screen of a panel of antibodies for use as ADCs since it would not be known if an ADC sample exhibited greater cytotoxicity because of the characteristics of the antibody as an ADC or because the sample contains more drug per antibody. Similarly, the ability to determine the actual or relative quantity of antibody or antibody conjugate in the samples also allows for relevant comparisons to be made between samples. Without knowledge of actual or relative quantity of antibody or antibody conjugate in the sample, it would not be known if an ADC exhibited greater cytotoxicity because of the particular antibody or simply because there is more antibody or ADC in the sample.

Preferably, in any the methods or compositions, a composition of a plurality of antibody conjugates is obtained wherein the antibodies have a uniform ratio of functionalized acceptor glutamines:antibody. In particular, the methods described herein permit substantially complete conjugation of antibodies, for are range of moieties Z, including large, charged and/or hydrophobic drugs. In one aspect provided is a composition wherein a high portion of antibodies in the composition (e.g. at least 80%, 85%, 90%, 95% of the antibodies) comprise at least one moiety of interest, wherein the composition is substantially free of antibodies comprising a number of moieties of interest that is greater than 2 times, optionally 1.5 times, the mean number of conjugates per antibody (e.g., the mean DAR). In one embodiment provided is a composition comprising a plurality of antibodies of Formula II or IV, wherein at least 70%, 80%. 85%, 90%, 95%, 98% or 99% of the antibodies in the composition have the same number of functionalized acceptor glutamine residues (Q) (e.g., a functionalized acceptor glutamine of Formula II or IV) per antibody. Preferably at least 70%, 80%. 85%, 90%, 95%, 98% or 99% of the antibodies in said first antibody composition have no more or no less than (m) functionalized acceptor glutamine residues (Q) per antibody, wherein m is an integer, e.g. m=1, 2, 3 or 4. Optionally, at least 70%, 80%, 90%, 95%, 98% or 99% of the antibodies in the composition have the same q, r and z values. It can optionally be specified that the antibodies will share the same —NH—$(C)_n$—X, L, V, V', Y, Y', R, RR' and/or Z moieties.

When the antibody samples are wild-type human antibodies they will possess one conserved acceptor glutamine at residue 295 of the heavy chain which when in non-glycosylated form will be accessible to a TGase. Murine antibodies of IgG1 isotype will comprise one conserved acceptor glutamine at residue 295 of the heavy chain and one conserved one acceptor glutamine at residue 288 or 290 of the heavy chain and will thus be conjugated to a moiety Z (or R) on two acceptor glutamines in each heavy chain. Murine antibodies of IgG2a and IgG2b isotypes will comprise one conserved acceptor glutamine at residue 288 or 290 of the heavy chain and will thus be conjugated to a moiety Z (or R) on one acceptor glutamines in each heavy chain. When screening murine antibody samples of different isotypes, it will therefore be useful, depending on the analysis to be made, to measure the number of conjugates per antibody or determine the isotype of each antibody sample to permit comparisons of activity (e.g. cytotoxicity) between different appropriate isotypes.

Typically, a high portion of antibodies in an antibody sample (e.g. at least 80%, 85%, 90%, 95% of the antibodies) comprise at least one moiety of interest, wherein antibody sample compositions are preferably also free of antibodies having conjugated light chains. For example, an antibody sample may comprise tetrameric antibodies covalently linked to a moiety of interest (Z), wherein the composition is characterized by a mean DAR of close to 2 (e.g., between 1.5 and 2.0, or between 1.7 and 2.0, between 1.8 and 2.0, or between 1.9 and 2.0), and wherein less than 10%, less than 5%, less than 2% or less than 1% of the antibodies in the composition comprise more than two moieties of interest (Z) per antibody. Preferably, less than 25%, 20%, 15% or preferably 10% of the antibodies in the composition comprise less than two moieties of interest (Z) per antibody. Optionally antibodies in an antibody sample are covalently linked to a moiety of interest (Z), wherein the composition is characterized by a mean DAR of close to 4 (e.g., between 3.0 and 4.0, or between 3.4 and 4.0, or between 3.6 and 4.0), wherein less than 10%, less than 5%, or less than 2% of the antibodies comprise more than four functionalized acceptor glutamines per antibody. Preferably, the composition is substantially free of antibodies having more than 4 moieties of interest (Z) per antibody.

The antibodies and antibody-conjugates identified using the evaluation methods can then be used for the manufacture of a pharmaceutical preparation and/or for the treatment or diagnosis of a mammal being in need thereof. In one embodiment, of the compounds defined above can be used for the manufacture of a pharmaceutical composition and/or for the treatment of a tumor or cancer in a mammal.

Also provided are any of the compounds defined above as a medicament or an active component or active substance in a medicament. In a further aspect the disclosure relates to a method for preparing a pharmaceutical composition containing a compound as defined above, to provide a solid or a liquid formulation for administration orally, topically, or by injection. Such a method or process at least comprises the step of mixing the compound with a pharmaceutically acceptable carrier.

In one aspect, the disclosure relates to a method to affect or prevent a predefined condition by exerting a certain effect, or detect a certain condition using a compound described herein, or a (pharmaceutical) composition comprising a compound described herein.

In a further embodiment, the disclosure relates to a method of treating a mammal being in need thereof, whereby the method comprises the administration of a pharmaceutical composition to the mammal in a therapeutically effective dose.

In a further embodiment, the disclosure relates to a method of treating a mammal having an illness characterized by undesired (cell) proliferation with a compound described herein. In another embodiment the disclosure relates to a method of treating a mammal carrying a tumor with a compound described herein. In yet another embodiment the disclosure relates to a method of treating a mammal having an inflammatory disease with a compound described herein. In yet another embodiment this invention relates to a method of treating a mammal having an autoimmune disease with a compound described herein. In yet another embodiment the disclosure relates to a method of treating a mammal having a bacterial or viral infection with a compound described herein.

In one embodiment, provided is a method of treating cancer in a mammal, whereby the method comprises the administration of a pharmaceutical composition to the mammal in a therapeutically effective dose.

In one embodiment, the compound is capable of being internalized into cells that express an antigen to which the antibody binds (e.g. a tumor or viral antigen) and/or induces internalization of the antigen on said antigen-expressing cells. In one embodiment, the compound described herein is toxic to a cell upon internalization (i.e. the compound comprises a moiety Z that is toxic to a cell). Preferably such compounds can be used in methods of killing or eliminating cells, preferably wherein said cells are tumor cells.

Also provided are pharmaceutical compositions comprising the compounds described herein may be administered in purified form together with a pharmaceutical carrier as a pharmaceutical composition. The preferred form depends on the intended mode of administration and therapeutic or diagnostic application. The pharmaceutical carrier can be any compatible, nontoxic substance suitable to deliver the compounds to the patient. Pharmaceutically acceptable carriers are well known in the art and include, for example, aqueous solutions such as (sterile) water or physiologically buffered saline or other solvents or vehicles such as glycols, glycerol, oils such as olive oil or injectable organic esters, alcohol, fats, waxes, and inert solids. A pharmaceutically acceptable carrier may further contain physiologically acceptable compounds that act for example to stabilize or to increase the absorption of the compounds described herein. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition. Pharmaceutically acceptable adjuvants, buffering agents, dispersing agents, and the like, may also be incorporated into the pharmaceutical compositions.

EXAMPLES

Example 1: BTG-Mediated Coupling of Substrates to Murine Antibodies

Methods

Antibodies having different variable and constant regions were evaluated for their suitability for enzymatic conjugation using translgutaminase. Experiments included deglycosylation, coupling and characterization of the antibodies via LC/MS. The antibodies used were antibodies generated in mice having different isotypes, with specificity for the same antigen: IgG2a (murine), IgG2b (murine), IgG1 (murine), and IgG1 (chimeric with human constant regions).

Complete deglycosylation for all four mAbs was achieved. Biotin-cadaverine was used as commercially available model substrate for all coupling experiments. For deglycosylation, antibody (1 mg) in PBS buffer (0.1 mol/L NaCl and 0.05 mol/L sodium phosphate buffer, pH 7.4) was incubated with 100 units (0.2 µL) of N-glycosidase F (PNGase F) from *Flavobacterium meningosepticum* (New England BioLabs, Ipswich, UK) at 37° C. overnight. The enzyme was then removed by centrifugation-dialysis (Vivaspin MWCO 50 kDa, Vivascience, Winkel, Switzerland). Recombinant BTG (EC 2.3.2.13) from *streptomyces mobaraensis* (Zedira, Darmstadt, Germany) was used at a concentration of 1 U/mL. The substrates are reacted with antibody (1 mg/mL) at ligand concentrations between 400 and 600 mol/L, providing a 60 to 90-fold excess of the substrates over the antibody. The reactions were performed in potassium-free phosphate buffered saline (PBS; pH 8) at 37° C. After 4 h to several days (depending on the antibody and the ligand), steady-state conditions are achieved. Excess ligand and enzyme were removed using centrifugation-dialysis (Vivaspin MWCO 50 kDa, Vivascience, Winkel, Switzerland).

Results

The chimeric human IgG1 has a glutamine at position 295 in the heavy chain which is expected to serve as an acceptor glutamine. However, upon conjugation, chimeric human IgG1 has only 1 biotin coupled to each heavy chain, while the murine IgG1 antibody has two glutamine sites per heavy chain which can be coupled with a suitable substrate using transglutaminase. The murine IgG2a and IgG2b isotype antibodies were coupled with 1 biotin per heavy chain, which is unexpected because the glutamine at the site of modification (residue 295, EU numbering as in Kabat) is not conserved in IgG2a and IgG2b. Alignment of the sequences of the heavy chain of human IgG1, mouse IgG1, IgG2a and IgG2b shows that only the mouse IgG1 has a conserved glutamine at position 295 (EU numbering), while murine IgG2a and IgG2b isotypes have an aspartic acid in this position. As mouse IgG1 were coupled to two and IgG2a and IgG2b coupled to one biotin-cadaverine per heavy chain, there must be another glutamine (accessible for the transglutaminase) in the heavy chains of those murine IgGs.

Structural comparison of human and murine in the region of the flexible loop where the human IgG1 bears the modifiable glutamine revealed two other possible glutamine candidates for enzymatic coupling which are also present in IgG2a and IgG2b but not in human IgG1 (residues 288 and 290 in the D-strand of the CH2 domain). Tryptic fragment analysis indicates that this site (288 or 290) is the coupling site. The D-strand (typically referred to as Kabat residues 286-293) is usually referred to as a beta strand. However the D-strand can assume a configuration where it is not packed into a sheet and is particularly solvent accessible. Analysis of the non-glycosylated constant region from crystal structures shows that when in non-glycosylated form, only about residues NAK (Kabat 286-288) are in the beta strand and the remaining residues, e.g., through 297 are in a random coil. The residues of the D-strand 286-297 are particularly exposed at the surface, even if 295 appears only partially exposed. The E-strand, by way of comparison, is not (or is barely) solvent accessible.

Example 2: BTG-Mediated Coupling of Substrates to Human Antibodies

Materials and Methods

Dansyl-cadaverine, biotin-cadaverine and bacterial TGase (recombinant bacterial transglutaminase, gene derived from *streptomyces mobaraensis*, BTG) were purchased from Zedira, Darmstadt, Germany. Polyclonal antibody (from serum Human AB Male) was purchased from Biowest.

Deglycosylation of Antibody

Antibody in PBS buffer (1 mg/mL) was incubated with 100 Units/mg protein of N-glycosidase F (PNGase F) from *Elizabethkingia meningosepticum* (Sigma) overnight at 37° C. The enzyme was then removed by centrifugation-dialysis (Vivaspin MWCO 50 kDa, Sigma).

General Coupling Reaction Conditions

Antibody (1 mg/mL), substrate (dansyl-cadaverin 400 µM or biotin-cadaverin 530 µM) and bacterial transglutaminase (6 U/mL; Zedira, Darmstadt, Germany) were mixed in PBS buffer (pH 7.4). The reaction was heated at 37° C. until steady-state conditions were achieved. Excess ligand and enzyme were then removed using centrifugation-dialysis (Vivaspin MWCO 50 kDa, Sigma-Aldrich). Reactions are monitored by HIC or LC/MS.

Western Blot Analysis

Western blot analysis: Enzymatically modified antibodies were subjected to SDS-PAGE and were transferred to polyvinylidene difluoride (PVDF) membranes (Immobilon P, Millipore). After blocking with 2% bovine serum albumine (BSA) in TBST (20 mM Tris-HCl, pH 7.5, 140 mM NaCl, 0.05% Tween-20) for 2 hour at room temperature (RT), membrane was incubated with Strepavidin-horseradish peroxidase conjugate (High Sensitivity Strepavidin-HRP diluted 1:20000; Beckman Coulter) for 30 min. Membrane was washed three times with TBST for 15 min and antibodies were detected with Immune-Star Western C Kit chemiluminescence substrate from Biorad.

Results

The selectivity of BTG coupling with respect to labeling of the heavy and light chain of a diverse range of antibodies of various isotypes was studied by reacting human polyclonal antibodies with biotin-cadaverine as substrate in the presence of BTG. All human gamma isotypes have a glutamine at residue 295 (Kabat EU Index) of the heavy chain constant region and thus can potentially have an acceptor glutamine in each heavy chain.

In order to assess unwanted labeling onto variable regions of antibodies, including at higher concentrations of BTGase (6 U/mL BTGase), polyclonal human antibody was reacted without prior PNGaseF deglycosylation which will serve to mask conjugation onto acceptor glutamines located in CH2 domains but not variable regions, and results were observed on SDS-PAGE. SDS-PAGE analysis of the conjugates revealed lack of substantial labeling of the heavy chain of the antibodies. Thus, BTG does not functionalize glutamines present within the variable regions of the antibodies. In order to assess labeling onto constant region acceptor glutamines of antibodies, polyclonal human antibody was deglycosylated using PNGaseF deglycosylation, and results were observed on SDS-PAGE. SDS-PAGE analysis of the conjugates revealed that the enzymatic reaction resulted in an substantially exclusive labeling of the heavy chain of the antibodies. Thus, BTG functionalizes glutamines present within the variable regions of the antibodies throughout the mixture of different antibodies and gamma isotypes.

Example 3: Synthesis of TGase Substrates with Reactive Groups

Materials and Methods

All solvents used for reactions were purchased as anhydrous grade from Acros Organics (puriss., dried over molecular sieves, $H_2O<0.005\%$) and were used without further purification unless otherwise stated. Solvents for extractions, column chromatography and thin layer chromatography (TLC) were purchased as commercial grade. All non aqueous reactions were performed under an argon atmosphere using flame-dried glassware and standard syringe/septa techniques. Commercially available reagents were used without further purification. In general, reactions were magnetically stirred and monitored by TLC performed on Merck TLC glass sheets (silica gel 60 $F_{254}$). Spots were visualized with UV light (λ=254 nm) or by staining with anisaldehyde solution or $KMnO_4$ solution and subsequent heating. Chromatographic purification of products was performed using Fluka silica gel 60 for preparative column chromatography.

Nuclear magnetic resonance (NMR) spectra were recorded in $CDCl_3$, $CD_3OD$ or $D_2O$ either on a Bruker Av-400 or a Bruker Av-500 spectrometer at room temperature. The measured chemical shifts are reported in δ (ppm) and the residual signal of the solvent was used as the internal standard ($CDCl_3$ $^1H$: δ=7.26 ppm, $^{13}C$: δ=77.0 ppm, $CD_3OD$ $^1H$: δ=3.31 ppm, $^{13}C$: δ=49.1 ppm, $D_2O$ $^1H$: δ=4.81 ppm). All $^{13}C$ NMR spectra were measured with complete proton decoupling. Data of NMR spectra are reported as follows: s=singlet, d=doublet, t=triplet, m=multiplet, dd=doublet of doublets, dt=doublet of triplets, br=broad signal. The coupling constant J is reported in Hertz (Hz). High resolution mass spectrometry (HRMS) was performed on a Bruker Daltonics maxis ESI-QTOF or a Varian HiResMALDI instrument.

The analytical and preparative HPLC system used was a Merck-Hitachi D-7000 system. The columns used for chromatography were either an Ultimate XB-C18 (4.6×150 mm, 3 μm) or an Xbridge C18 (4.6×150 mm, 5 μm) for analytical separations operated with a flow of 1 ml/min. For preparative purifications, either an Ultimate XB-C18 (21.2×150 mm, 5 μm) or an Xbridge C18 (10×150 mm, 5 μm) column was used operated with a flow of 15 ml/min and 4 ml/min respectively.

Figure 15:
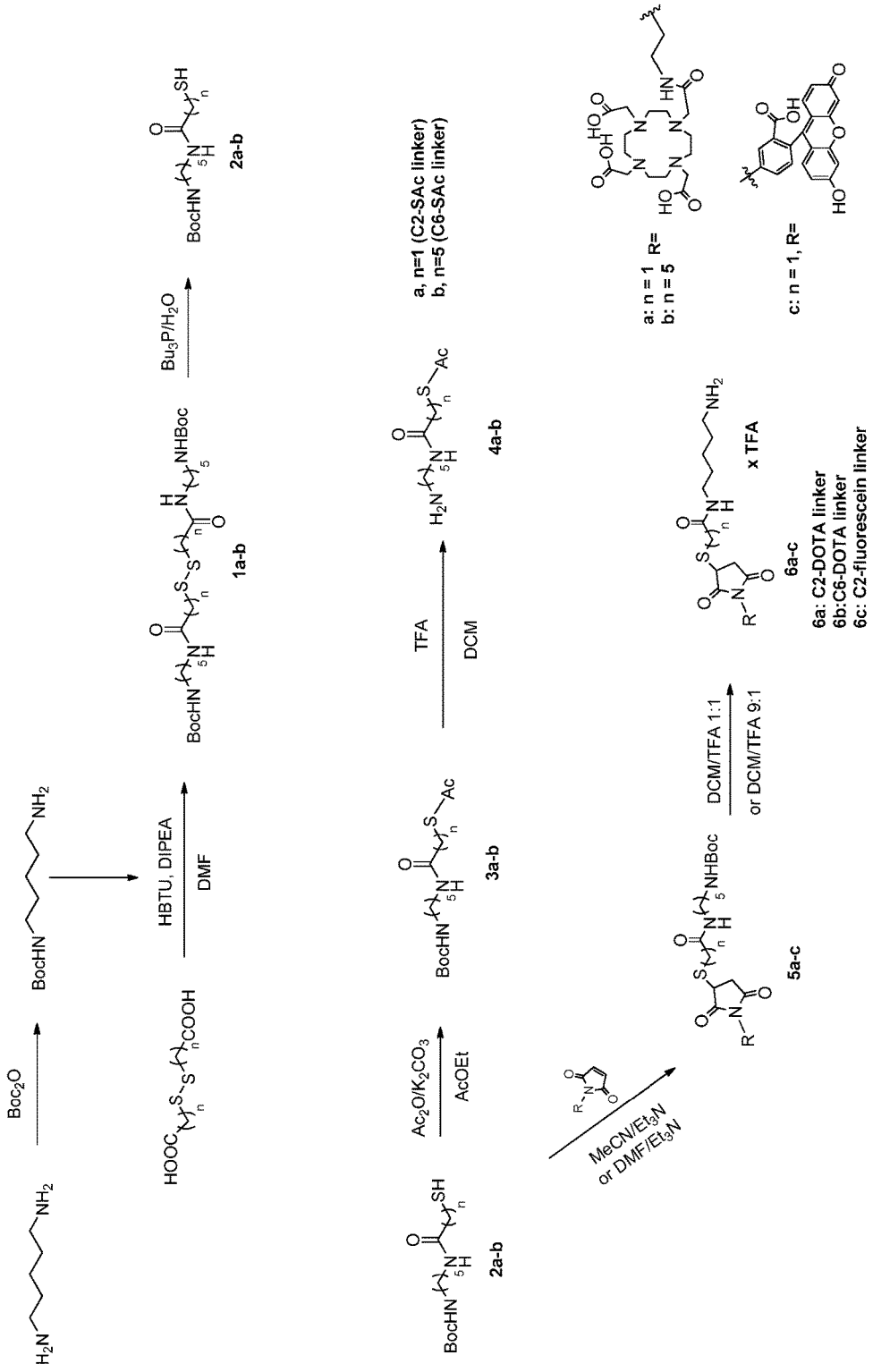
FIG. 15 shows a scheme for preparing S-acetyl-protected cadaverin linkers of different lengths (either n=1 or 5 carbons) as well as a short thiol linker coupled to maleimide-DOTA.
Figure 16A:
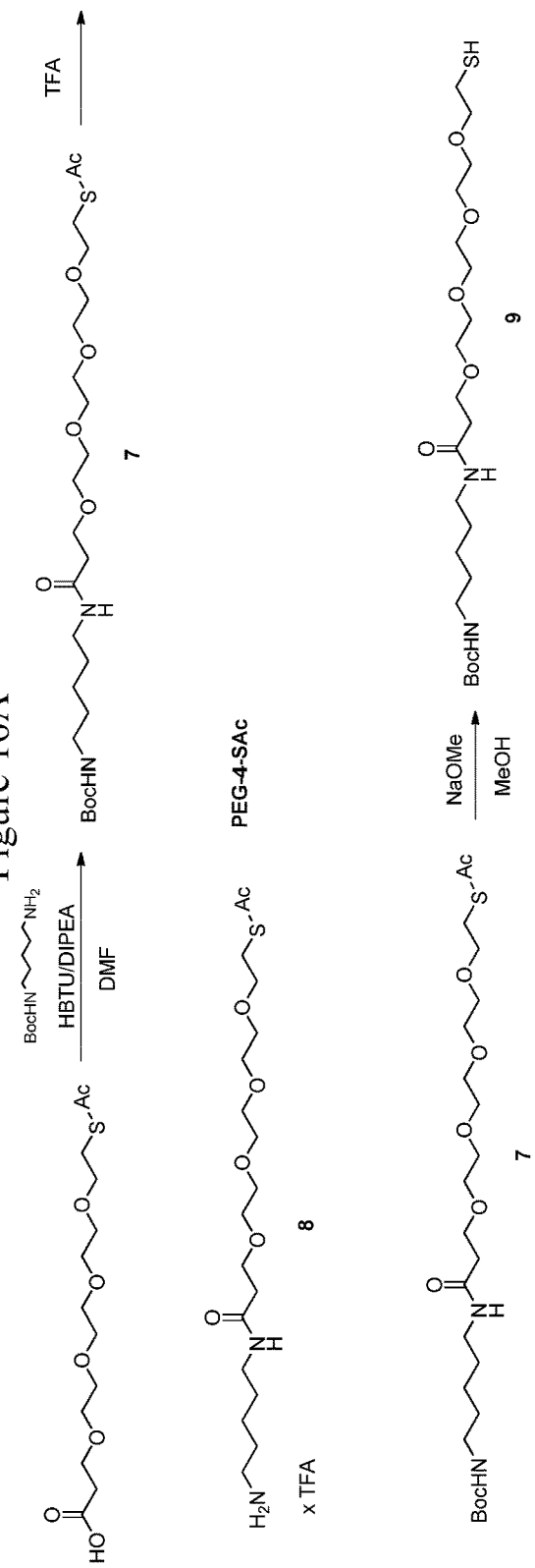
FIGS. 16A, 16B and 16C show schemes for preparing linkers

Compounds 1-6 and reaction schemes are shown in FIG. 15. Compounds 7-9 and reaction schemes are shown in FIG. 16A. For Compounds 10-13 and reaction schemes, see FIG. 16B.

di-tert-butyl (((2,2'-disulfanediylbis(acetyl))bis (azanediyl))bis(pentane-5,1-diyl))dicarbamate (1a)

In a solution of 2,2'-disulfanediyldiacetic acid (160 mg, 0.878 mmol), tert-butyl (5-amino-pentyl)carbamate (391 mg, 1.932 mmol) and DIPEA (920 μl, 5.27 mmol) in DMF (4.9 ml), HBTU (1.33 g, 3.51 mmol) was added portionwise at room temperature. After stirring for 5 hours, the brownish solution was diluted with ethyl acetate (80 ml) and washed with water (3×30 ml) and brine (1×30 ml). The organic layer was dried under sodium sulfate, filtered and evaporated to dryness. The crude was purified by flash column chromatography on silica using $CHCl_3$/EtOH 95:5 to yield 420 mg (87%) of a yellow oil which solidified upon standing at room temperature. $^1H$ NMR (400 MHz, $CDCl_3$): δ 6.91 (br, 2H), 4.68 (br, 2H), 3.44 (s, 4H), 3.29 (dt, $J_1$=7.2 Hz, $J_2$=6.8 Hz, 4H), 3.10 (dt, $J_1$=7.7 Hz, $J_2$=6.3 Hz, 4H), 1.64-1.31 (m, 30H). $^{13}C$ NMR (100 MHz, $CDCl_3$): δ 168.5, 156.1, 79.1, 42.6, 40.2, 39.8, 29.7, 28.8, 28.4, 23.9. ESI-QTOF MS m/z calculated for $C_{24}H_{46}N_4O_6S_2$ $[M+H]^+$ 551.2932, measured 551.2921.

di-tert-butyl(((6,6'-disulfanediylbis(hexanoyl))bis (azanediyl))bis(pentane-5,1-diyl))dicarbamate (1b)

In a solution of 6,6'-disulfanediyldihexanoic acid (250 mg, 0.849 mmol), tert-butyl (5-amino-pentyl)carbamate (412 mg, 2.038 mmol) and DIPEA (0.890 ml, 5.09 mmol) in DMF (4.7 ml), HBTU (1.29 g, 3.40 mmol) was added portionwise at room temperature. After stirring for 20 hours, the yellowish reaction mixture was diluted with ethyl acetate (70 ml) and washed with cold HCl 0.1N (3×50 ml), $NaHCO_3$ (sat) (1×50 ml) water (1×50 ml) and brine (1×50 ml). The organic layer was dried under sodium sulfate, filtered and evaporated to dryness. The crude was purified by flash column chromatography on silica using $CHCl_3$/EtOH 95:5 to yield 525 mg (93%) of compound as a yellow sticky solid. $^1H$ NMR (400 MHz, $CDCl_3$): δ 5.87 (br, 2H), 4.64 (br, 2H), 3.22 (dt, $J_1$=7.3 Hz, $J_2$=6.8 Hz, 4H), 3.09 (dt, $J_1$=8.1 Hz, $J_2$=6.7 Hz, 4H), 2.65 (t, J=7.2 Hz, 4H), 2.16 (t, J=7.2 Hz, 4H), 1.73-1.59 (m, 8H), 1.55-1.45 (m, 8H), 1.42 (s, 18H), 1.37-1.28 (m, 4H). $^{13}C$ NMR (100 MHz, $CDCl_3$): δ 172.9, 156.1, 79.0, 40.2, 39.2, 38.8, 36.5, 29.7, 29.1, 28.8, 28.4, 28.0, 25.3, 23.9. ESI-QTOF MS m/z calculated for $C_{32}H_{62}N_4O_6S_2$ $[M+H]^+$ 663.4184, measured 663.4185.

tert-butyl (5-(2-mercaptoacetamido)pentyl)carbamate (2a)

To a solution of Di-tert-butyl((((2,2'-disulfanediylbis (acetyl))bis(azanediyl))bis(pentane-5,1-diyl))di-carbamate (390 mg, 0.478 mmol) in a mixture of tetrahydrofuran (7 ml) and water (0.74 ml), tributylphosphine (528 mg, 2.48 mmol) was added dropwise at room temperature, within 1 min. The reaction mixture was stirred for 1 h and then the volatiles were removed under reduced pressure at 33° C. The crude was azeotroped once with 50 ml benzene to remove traces of water and the residue was purified with flash column chromatography on silica with $CHCl_3$/EtOH 95:5 to yield a slightly yellow clear oil. The product was re-purified with flash column chromatography with hexane/ethyl acetate 2:8 to remove oxidized tributylphosphine byproducts. Final yield was 180 mg (91%) of product as a colorless oil which solidified to a white solid after storage at −25° C. $^1H$ NMR (400 MHz, $CDCl_3$): δ 6.73 (br, 1H), 4.57 (br, 1H), 3.28 (dt, $J_1$=7.6 Hz, $J_2$=6.9 Hz, 2H), 3.23 (d, J=9.0 Hz, 2H), 3.11 (dt, $J_1$=8.1 Hz, $J_2$=6.6 Hz, 2H), 1.87 (t, $^3J$=9.0 Hz, 1H), 1.61-1.47 (m, 4H), 1.43 (s, 9H), 1.40-1.30 (m, 2H). $^{13}C$ NMR (100 MHz, $CDCl_3$): δ 169.1, 156.1, 79.1, 40.2, 39.7, 29.7, 29.0, 28.4, 28.3, 23.9. ESI-QTOF MS m/z calculated for $C_{12}H_{24}N_2O_3S$ $[M+Na]^+$ 299.1400, measured 299.1408.

tert-butyl (5-(6-mercaptohexanamido)pentyl)carbamate (2b)

To a solution of di-tert-butyl((((6,6'-disulfanediylbis (hexanoyl))bis(azanediyl))bis(pentane-5,1-diyl))di-carbamate (196 mg, 0.296 mmol) in a mixture of tetrahydrofuran (3 ml) and water (0.31 ml, 17.21 mmol), tributylphosphine (272 μl, 1.035 mmol) was added dropwise at room temperature, within 1 min. The reaction mixture was stirred for 1 h and then the volatiles were removed under reduced pressure at 33° C. The crude was azeotroped once with 50 ml benzene to remove traces of water and the residue was purified with flash column chromatography on silica with chloroform/ ethanol 95:5 to yield a slightly yellow clear oil. NMR revealed that the compound was contaminated with tributylphosphine oxidized byproducts so the crude was purified again with flash column chromatography with hexane/ethyl acetate 2:8 to yield 180 mg (91%) of product as a colorless oil which solidified after storage at −25° C. $^1H$ NMR (400 MHz, $CDCl_3$): δ 5.88 (br, 1H), 4.57 (br, 1H), 3.23 (dt, $J_1$=7.3 Hz, $J_2$=6.9 Hz, 2H), 3.09 (dt, $J_1$=7.8 Hz, $J_2$=6.5 Hz, 2H), 2.52 (dt, $J_1$=8.0 Hz, $J_2$=7.6 Hz, 2H), 2.16 (t, J=7.5 Hz, 4H), 1.69-1.57 (m, 4H), 1.56-1.46 (m, 4H), 1.43 (s, 9H), 1.36-1.28 (m, 3H). $^{13}C$ NMR (100 MHz, $CDCl_3$): δ 172.8, 156.1, 79.1, 40.2, 39.2, 36.5, 33.6, 29.7, 29.1, 28.4, 27.9, 25.1, 24.4, 23.9. ESI-QTOF MS m/z calculated for $C_{16}H_{32}N_2O_3S$ [M+H]$^+$ 333.2206, measured 333.2198.

S-(2-((5-((tert-butoxycarbonyl)amino)pentyl)amino)-2-oxoethyl)ethanethioate (3a)

To a mixture of tert-butyl (5-(2-mercaptoacetamido)pentyl)carbamate (189 mg, 0.684 mmol) and dry potassium carbonate (189 mg, 1.368 mmol) in degassed (freeze-pump-thaw) ethyl acetate (2.7 ml), acetic anhydride (77 mg, 0.821 mmol) was added and the reaction was stirred for 16 h. The reaction was then diluted with ethyl acetate (30 ml), filtered and washed with cold water (1×15 ml) and brine (1×15 ml), dried under sodium sulfate and evaporated to dryness. The crude was purified by flash column chromatography on silica with CHC$_3$/EtOH 96:4 to yield 192 mg (88%) of product as a white solid. $^1$H NMR (400 MHz, CDCl$_3$): δ 6.22 (br, 1H), 4.56 (br, 1H), 3.51 (s, 2H), 3.21 (dt, $J_1$=7.1 Hz, $J_2$=6.9 Hz, 2H), 3.09 (dt, $J_1$=7.6 Hz, $J_2$=6.6 Hz, 2H), 2.40 (s, 3H), 1.54-1.45 (m, 4H), 1.43 (s, 9H), 1.35-1.26 (m, 2H). $^{13}$C NMR (100 MHz, CDCl$_3$): δ 190.5, 168.0, 156.0, 79.1, 40.3, 39.6, 33.1, 30.3, 29.6, 29.0, 28.4, 23.8. ESI-QTOF MS m/z calculated for $C_{14}H_{26}N_2O_4S$ [M+Na]$^+$ 341.1505, measured 341.1506.

S-(6-((5-((tert-butoxycarbonyl)amino)pentyl)amino)-6-oxohexyl)ethanethioate (3b)

To a solution of tert-butyl (5-(6-mercaptohexanamido)pentyl)carbamate (180 mg, 0.541 mmol) and dry potassium carbonate (150 mg, 1.083 mmol) in degassed (freeze-pump-thaw) ethyl acetate (2.2 ml), acetic anhydride (61 μl, 0.650 mmol) was added and the reaction was stirred for 16 h. The reaction was then diluted with ethyl acetate (20 ml), filtered and washed with cold water (1×10 ml) and brine (1×10 ml), dried under sodium sulfate and evaporated to dryness. The crude was purified by flash column chromatography using chloroform/ethanol 96:4 to yield 182 mg (90%) of a white solid. $^1$H NMR (400 MHz, CDCl$_3$): δ 5.68 (br, 1H), 4.61 (br, 1H), 3.21 (dt, $J_1$=7.3 Hz, $J_2$=0.9 Hz, 2H), 3.09 (dt, $J_1$=7.7 Hz, $J_2$=6.4 Hz, 2H), 2.83 (t, J=7.2 Hz, 2H), 2.30 (s, 1H), 2.14 (t, J=7.2 Hz, 2H), 1.67-1.44 (m, 8H), 1.42 (s, 9H), 1.40-1.27 (m, 4H). $^{13}$C NMR (100 MHz, CDCl$_3$): δ 196.0, 172.8, 156.1, 79.3, 40.2, 39.2, 36.4, 30.6, 29.7, 29.2, 29.1, 28.8, 28.4, 28.3, 25.1, 23.9. ESI-QTOF MS m/z calculated for $C_{18}H_{34}N_2O_4S$ [M+H]$^+$ 375.2312, measured 375.2312.

S-(2-((5-aminopentyl)amino)-2-oxoethyl) ethanethioate (4a) (C2-SAc Linker)

To a solution of S-(2-((5-((tert-butoxycarbonyl)amino)pentyl)amino)-2-oxoethyl)ethanethioate (189 mg, 0.594 mmol) in dichloromethane (7.9 ml), trifluoroacetic acid (0.92 ml, 11.87 mmol) was added dropwise at 0° C. After stirring for 10 min, the reaction mixture was allowed to reach room temperature where it was stirred for 1 h. Toluene was then added (20 ml), volatiles were removed under reduced pressure and the residue was dried under high vacuum for 30 min to yield quantitatively a slightly yellow oil which was sufficiently pure when analyzed by NMR. The oil was dissolved in water and lyophilized to give a white solid. $^1$H NMR (400 MHz, CD$_3$OD): 3.60 (s, 2H), 3.20 (t, J=6.9 Hz, 2H), 2.91 (t, J=7.6 Hz, 2H), 2.37 (s, 3H), 1.72-1.61 (m, 2H), 1.59-1.50 (m, 2H), 1.45-1.35 (m, 2H). $^{13}$C NMR (100 MHz, CDCl$_3$): δ 196.3, 170.8, 40.7, 40.4, 33.9, 30.1, 29.9, 28.2, 24.6. ESI-QTOF MS m/z calculated for $C_9H_{18}N_2O_2S$ [M+H]$^+$ 219.1162, measured 219.1171.

S-(6-((5-aminopentyl)amino)-6-oxohexyl)ethanethioate (4b) (C6-SAc Linker)

To a solution of S-(6-((5-((tert-butoxycarbonyl)amino)pentyl)amino)-6-oxohexyl)ethanethioate (187 mg, 0.5 mmol) in dichloromethane (6.6 ml), trifluoroacetic acid (0.77 ml, 5.34 mmol) was added dropwise at 0° C. After stirring for 10 min, the reaction mixture was allowed to reach room temperature where it was stirred for 1 h. The volatiles were removed under reduced pressure at 30° C. and the residue was azeotroped with toluene and dried under high vacuum for 30 min. Lyophilization yielded a white solid (185 mg) which was sufficiently pure by NMR. $^1$H NMR (400 MHz, CD$_3$OD): δ 3.18 (t, J=7.0 Hz, 2H), 2.92 (t, J=7.8 Hz, 2H), 2.86 (t, J=7.3 Hz, 2H), 2.30 (s, 3H), 2.17 (t, J=7.3 Hz, 2H), 1.72-1.50 (m, 8H), 1.45-1.33 (m, 4H). $^{13}$C NMR (100 MHz, CD$_3$OD): 197.7, 176.2, 40.7, 40.0, 37.0, 30.64, 30.61, 30.0, 29.8, 29.4, 28.3, 26.6, 24.8. ESI-QTOF MS m/z calculated for $C_{13}H_{26}N_2O_2S$ [M+H]$^+$ 275.1788, measured 275.1785.

2,2',2"-(10-(2-((2-(3-((2-((5-((tert-butoxycarbonyl)amino)pentyl)amino)-2-oxoethyl)thio)-2,5-dioxopyrrolidin-1-yl)ethyl)amino)-2-oxoethyl)-1,4,7,10-tetraazacyclododecane-1,4,7-triyl)triacetic Acid (5a)

DOTA-maleimide (25 mg, 0.032 mmol) was suspended in acetonitrile (1 ml) and triethylamine was added (22.59 μl, 0.162 mmol) and after 5 min of stirring, a clear colorless solution was formed. A solution of tert-butyl (5-(2-mercaptoacetamido)pentyl)-carbamate (10.54 mg, 0.038 mmol) in 0.5 ml acetonitrile was then added and the reaction was stirred for 1 h at which point HPLC confirmed complete consumption of starting material. The solvent system used for reaction monitoring is as follows: water/0.1% TFA (solvent A), acetonitrile (solvent B); 0-5 min: 0% B, 5-20 min: 0-50% B, 20-25 min: 50% B, 25-30 min 50-0% B; UV=214 nm; $t_R$=18.3 min. The reaction was then diluted with 3 ml water and was purified by preparative HPLC with the following solvent system: water/0.1% TFA (solvent A), acetonitrile (solvent B); 0-5 min: 0% B, 5-20 min: 0-50% B. The product eluted approximately at 17 min; XB-C18 column; UV=214 nm. The product was obtained as a white solid after lyophilization (19.7 mg, 77% yield). ESI-MS m/z calculated for $C_{34}H_{58}N_8O_{12}S$ [M+H]$^+$ 803.39, measured 803.40.

2,2',2"-(10-(2-((2-(3-((6-((5-((tert-butoxycarbonyl)amino)pentyl)amino)-6-oxohexyl)thio)-2,5-dioxopyrrolidin-1-yl)ethyl)amino)-2-oxoethyl)-1,4,7,10-tetraazacyclododecane-1,4,7-triyl)triacetic Acid (5b)

To a solution of DOTA-maleimide (80 mg, 0.102 mmol) and triethylamine (52.5 mg, 0.519 mmol) in acetonitrile (3.5 ml) was added a solution of tert-butyl(5-(6-mercaptohexanamido)pentyl)carbamate (40.6 mg, 0.122 mmol) in acetonitrile (1.5 ml) and the reaction mixture was stirred for 6 h at room temperature. Approximately half of the solvent was then removed under reduced pressure, water was added (3 ml) and the mixture was purified with preparative RP HPLC with the following solvent system: water/0.1% TFA (solvent A), acetonitrile (solvent B); 0-5 min: 0% B, 5-20 min: 0-50% B; $t_R$=17.4 min; UV=214 nm; XB-C18 column. The product was obtained as a white solid after lyophilization (58 mg, 57% yield). ESI-MS m/z calculated for $C_{38}H_{66}N_8O_{12}S$ [M+H]$^+$ 859.46, measured 859.39.

5-(3-((2-((5-tert-butoxycarbonyl)amino)pentyl)
amino)-2-oxoethyl)thio)-2,5-dioxopyrrolidin-1-yl)-
2-(6-hydroxy-3-oxo-3H-xanthen-9-yl)benzoic Acid
(5c)

A solution of tert-butyl(5-(2-mercaptoacetamido)pentyl) carbamate (14.22 mg, 0.051 mmol) in DMF (0.3 ml) was added to a solution of 5-(2,5-dioxo-2,5-dihydro-1H-pyrrol-1-yl)-2-(6-hydroxy-3-oxo-3H-xanthen-9-yl)benzoic acid (18.32 mg, 0.043 mmol) and triethylamine (4.29 µmol) and the clear yellow solution was stirred for 3 h at room temperature. After this time, the reaction was diluted with water (3 ml) and purified with preparative RP HPLC with the following solvent system: water/0.1% HCOOH (solvent A), acetonitrile (solvent B); 0-5 min: 30% B, 5-20 min: 30-80% B; UV=254 nm; $t_R$=15.4 min; XB-C18 column. The product was obtained as a bright yellow solid after lyophilization (22 mg, 73% yield). ESI-MS m/z calculated for $C_{36}H_{37}N_3O_{10}S$ [M+H]$^+$ 704.23, measured 704.05.

2,2',2''-(10-(2-((2-(3-((2-((5-aminopentyl)amino)-2-
oxoethyl)thio)-2,5-dioxopyrrolidin-1-yl)ethyl)-
amino)-2-oxoethyl)-1,4,7,10-tetraazacyclododecane-
1,4,7-triyl)triacetic Acid (6a) (C2-DOTA Linker)

2,2',2''-(10-(2-((2-(3-((2-((5-((tert-butoxycarbonyl) amino)pentyl)amino)-2-oxoethyl)thio)-2,5-dioxo-pyrrolidin-1-yl)ethyl)amino)-2-oxoethyl)-1,4,7,10-tetraazacyclododecane-1,4,7-triyl)triacetic acid (18 mg, 0.022 mmol) was dissolved in a mixture of dichloromethane/TFA 1:1 (2.7 ml) at 0° C. The reaction mixture was stirred for 10 min at this temperature and was then allowed to reach room temperature where it was stirred for 1 h at which point HPLC confirmed complete consumption of the starting material. The volatiles were removed under reduced pressure at 20° C. and the crude was dried under high vacuum for 30 min. The residue was dissolved in 1 ml water and was purified with preparative HPLC to provide 12.7 mg (81%) of a white solid after lyophilization. The solvent systems that were used were the same as in the case of 5a ($t_R$=12.8 min and $t_R$=11.6 min for analytical and preparative HPLC respectively). $^1$H NMR (500 MHz, D$_2$O): δ 4.26-2.89 (br, 28H), 4.07 (dd, $J_1$=9.1 Hz, $J_2$=4.1 Hz, 1H), 3.58 (d, J=15.3 Hz, 1H), 3.42 (d, J=15.3 Hz, 1H), 3.31 (dd, $J_1$=19.1 Hz, $J_2$=9.1 Hz, 1H), 3.22, (t, J=7.1 Hz, 2H), 2.99 (t, J=7.5 Hz, 2H), 2.74 (dd, $J_1$=19.1 Hz, $J_2$=4.1 Hz, 1H), 1.72-1.64 (m, 2H), 1.60-1.52 (m, 2H), 1.44-1.36 (m, 2H). $^{13}$C NMR (100 MHz, D$_2$O): δ 178.8, 178.1, 171.3, 163.0, 162.7, 117.4, 115.1, 54.7, 40.3, 39.4, 39.3, 38.3, 37.1, 35.5, 34.5, 27.7, 27.6, 26.3, 22.9 ESI-MS m/z calculated for $C_{29}H_{51}N_8O_{10}S$ [M+H]$^+$ 703.34, measured 703.32.

2,2',2''-(10-(2-((2-(3-((6-((5-aminopentyl)amino)-6-
oxohexyl)thio)-2,5-dioxopyrrolidin-1-yl)ethyl)-
amino)-2-oxoethyl)-1,4,7,10-tetraazacyclododecane-
1,4,7-triyl)triacetic Acid (6b) (C6-DOTA Linker)

Compound 5b (45 mg, 0.045 mmol) was dissolved in a mixture of dichloromethane/TFA 1:1 (5.4 ml) at 0° C. and after stirring for 10 min at this temperature, the reaction mixture was allowed to reach room temperature where it was stirred for 2 h. The volatiles when then removed under reduced pressure at 30° C. and traces of TFA were removed with drying under high vacuum for 30 min. The residue was dissolved in water (4 ml) and was purified with preparative RP HPLC using the method described for 5b; $t_R$=13.5 min. ESI-MS m/z calculated for $C_{33}H_{58}N_8O_{10}S$ [M+H]$^+$ 759.41, measured 759.40.

5-(3-((2-((5-aminopentyl)amino)-2-oxoethyl)thio)-2,
5-dioxopyrrolidin-1-yl)-2-(6-hydroxy-3-oxo-3H-
xanthen-9-yl)benzoic Acid (6c) (C2-Fluorescein
Linker)

To an ice cold suspension of 5c (10 mg, 0.014 mmol) in dichloromethane (2 ml), TFA (200 µl, 2.60 mmol) was added dropwise and the clear bright yellow solution was stirred for 10 min at 0° C. for 10 min before allowing it to reach room temperature where it was stirred for 40 min. Toluene was then added and the volatiles were removed under reduced pressure. The crude was purified with semi-preparative RP HPLC with the following system: water/0.1% TFA (solvent A), acetonitrile (solvent B); 0-3 min: 5% B, 3-10 min: 5-25% B, 10-20 min: 25% B; UV=254 nm; $t_R$=15.3 min; Xbridge column. The product was obtained as a bright yellow solid after lyophilization (6.7 mg, 78% yield). ESI-MS m/z calculated for $C_{31}H_{29}N_3O_8S$ [M+H]$^+$ 604.18, measured 604.04.

Synthesis of PEG Linkers
For Compounds 7-9 and reaction schemes, see FIG. 16A.

S-(2,2-dimethyl-4,12-dioxo-3,15,18,21,24-pentaoxa-
5,11-diazahexacosan-26-yl) ethanethioate (7)

HBTU (421 mg, 1.11 mmol) was slowly added to a solution of 2-oxo-6,9,12,15-tetraoxa-3-thiaocta-decan-18-oic acid (300 mg, 0.925 mmol) and DIPEA (0.32 ml, 1.85 mmol) in DMF (4.5 ml) and the resulting solution was stirred for 15 min. A solution of tert-butyl (5-aminopentyl) carbamate (225 mg, 1.11 mmol) in DMF (0.6 ml) was then added dropwise and the reaction was stirred for 14 h. The reaction was then diluted with 60 ml ethyl acetate and was washed with water (2×25 ml) and brine (1×25 ml). The organic layer was dried under sodium sulfate, filtered and evaporated under reduced pressure. The crude was purified by flash column chromatography on silica using chloroform/ethanol 95:5 to afford 380 mg (81%) of product as a slight yellow oil. $^1$H NMR (400 MHz, CDCl$_3$): δ 6.51 (br, 1H), 4.66 (br, 1H), 3.70 (t, J=5.8 Hz, 2H), 3.65-3.59 (m, 12H), 3.57 (t, J=6.6 Hz, 2H), 3.21 (dt, $J_1$=7.3 Hz, $J_2$=6.9 Hz, 2H), 3.12-3.02 (m, 4H), 2.44 (t, J=5.8, 2H), 2.31 (s, 3H), 1.53-1.43 (m, 4H), 1.41 (s, 9H), 1.36-1.27 (m, 2H). $^{13}$C NMR (100 MHz, CDCl$_3$): δ 195.4, 171.5, 156.0, 78.9, 70.6, 70.5, 70.3, 70.2, 70.1, 69.7, 67.3, 40.3, 39.0, 36.9, 30.5, 29.6, 29.2, 28.7, 28.4, 24.0. ESI-QTOF MS m/z calculated for $C_{23}H_{44}N_2O_8S$ [M+H]$^+$ 509.2891, measured 509.2884.

S-(21-amino-15-oxo-3,6,9,12-tetraoxa-16-azaheni-
cosyl) ethanethioate (8) (PEG-4-SAc Linker)

To an ice cold solution of S-(2,2-dimethyl-4,12-dioxo-3, 15,18,21,24-pentaoxa-5,11-diazahexacosan-26-yl)ethanethioate (370 mg, 0.73 mmol) in dichloromethane (9.7 ml) was added trifluoroacetic acid (1.1 ml, 14.55 mmol). After stirring for 10 min, the reaction mixture was allowed to reach room temperature and stirred for 2 h. The volatiles were then removed under reduced pressure, followed by drying under high vacuum. A light yellow oil resulted which was sufficiently pure as revealed by NMR (quantitative yield). $^1$H NMR (400 MHz, CDCl$_3$): δ 7.79 (br, 1H), 7.23 (br, 3H), 2.33 (t, J=5.3 Hz, 2H), 3.69-3.56 (m, 14H), 3.31

(dt, J₁=7.5 Hz, J₂=6.1 Hz, 2H), 3.06 (t, J=6.7 Hz, 2H), 3.03-2.92 (m, 2H), 2.58 (t, J=5.3 Hz, 2H), 2.32 (s, 3H), 1.77-1.65 (m, 2H), 1.64-1.51 (m, 2H), 1.49-1.38 (m, 2H). $^{13}$C NMR (100 MHz, CDCl₃): δ 195.7, 174.0, 70.2, 69.99, 69.97, 69.9, 69.8, 69.6, 67.2, 40.0, 38.8, 35.8, 30.4, 28.1, 27.2, 26.0, 22.5. ESI-QTOF MS m/z calculated for C₁₈H₃₆N₂O₆S [M+H]⁺ 409.2367, measured 409.2381.

Tert-butyl (1-mercapto-15-oxo-3,6,9,12-tetraoxa-16-azahenicosan-21-yl)carbamate (9)

A solution of sodium methoxide 0.5 M in methanol (1.8 ml, 0.904 mmol) was added dropwise to a solution of 7 (92 mg, 0.181 mmol) in degassed (freeze-pump-thaw) methanol and the reaction was stirred at room temperature for 3 h. After neutralization with Amberlite 120, the solution was filtered and evaporated to dryness. The crude was purified by flash column chromatography on silica using chloroform/ethanol 95:5 to yield a clear colorless oil (75 mg, 89%). $^1$H NMR (400 MHz, CDCl₃): δ 6.48 (br, 1H), 4.64 (br, 1H), 3.71 (t, J=5.7 Hz, 2H), 3.66-3.61 (m, 12H), 3.60 (t, J=6.4 Hz, 2H, partially overlapped by the previous multiplet), 3.22 (q, J₁≈J₂=7.0, 2H), 3.09 (dt, J₁=6.4 Hz, J₂=7.8 Hz, 2H), 2.68 (td, J₁=6.4 Hz, J₂=8.2 Hz, 2H), 2.45 (t, J=5.7 Hz, 2H), 1.59 (t, J=8.2 Hz, 1H), 1.55-1.46 (m, 4H), 1.43 (s, 9H), 1.37-1.30 (m, 2H). $^{13}$C NMR (100 MHz, CDCl₃): δ 171.5, 156.0, 79.0, 72.8, 70.6, 70.5, 70.3, 70.2, 67.3, 40.3, 39.1, 37.0, 29.6, 29.2, 28.4, 24.2, 24.0.

Synthesis of Azide Linkers

Figure 16B:
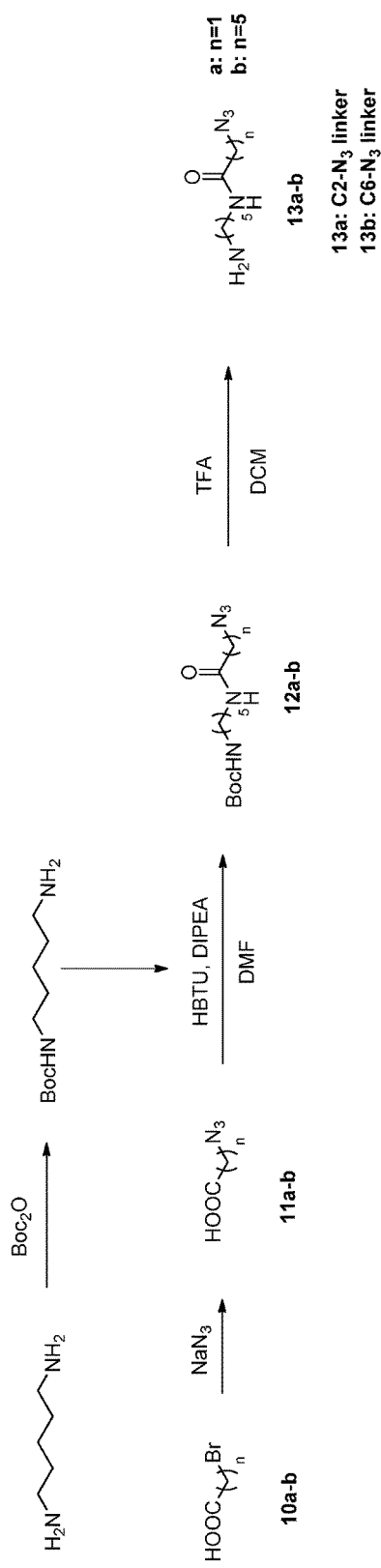

For Compounds 10-13 and reaction schemes, see FIG. 16B.

Compounds 11a and 11b were synthesized by following procedures already published in the literature (Brabez N. et al, Journal of Medicinal Chemistry, 2011, 54(20), 7375-7384 for 11a and Kuil J. et al, Organic and Biomolecular Chemistry, 2009, 7, 4088-4094 for 11b)

tert-butyl (5-(2-azidoacetamido)pentyl)carbamate (12a)

In a solution of 2-azidoacetic acid (50 mg, 0.495 mmol), tert-butyl (5-amino-pentyl)carbamate (120 mg, 0.594 mmol) and DIPEA (128 mg, 0.989 mmol) in DMF (2.7 ml), HBTU (225 mg, 0.594 mmol) was added slowly at room temperature. After stirring for 3 hours, the slight yellow solution was diluted with ethyl acetate (30 ml) and was washed with HCl 0.5 M (3×15 ml) and sat. NaHCO₃ (1×15 ml) solutions, water (1×15 ml) and brine (1×15 ml). The organic layer was dried under sodium sulfate, filtered and evaporated to dryness. The crude was purified by flash column chromatography on silica using chloroform/EtOH 95:5 to yield a clear colorless oil (128 mg, 91%). $^1$H NMR (400 MHz, CDCl₃): δ 6.35 (br, 1H), 4.55 (br, 1H), 3.97 (s, 2H), 3.28 (dt, J₁=7.2 Hz, J₂=6.9 Hz, 2H), 3.11 (dt, J₁=7.8 Hz, J₂=6.5 Hz, 2H), 1.61-1.47 (m, 4H), 1.43 (s, 9H), 1.40-1.31 (m, 2H). $^{13}$C NMR (100 MHz, CDCl₃): δ 166.5, 156.0, 79.1, 52.7, 40.2, 39.2, 29.7, 29.0, 28.4, 23.9.

Tert-butyl (5-(6-azidohexanamido)pentyl)carbamate (12b)

HBTU (290 mg, 0.764 mmol) was slowly added to a solution of 6-azidohexanoic acid (100 mg, 0.636 mmol) and DIPEA (164 mg, 1.273 mmol) in DMF (3 ml) and the resulting solution was stirred for 15 min. A solution of tert-butyl (5-aminopentyl)carbamate (154 mg, 0.764 mmol) in DMF (0.5 ml) was then added dropwise and the reaction was stirred for 3 h. After this time, the reaction mixture was diluted with ethyl acetate (40 ml) and washed with HCl 0.5 M (3×20 ml) and sat. NaHCO₃ (1×20 ml) solutions, water (1×20 ml) and brine (1×20 ml). The organic layer was dried under sodium sulfate, filtered and evaporated to dryness. The crude was purified by flash column chromatography on silica using chloroform/EtOH 95:5 to yield a clear colorless oil (189 mg, 87%). $^1$H NMR (400 MHz, CDCl₃): δ 5.61 (br, 1H), 4.58 (br, 1H), 3.30-3.20 (m, 4H), 3.10 (dt, J₁=8.0 Hz, J₂=6.8 Hz, 2H), 2.16 (t, J=7.4 Hz, 2H), 1.56-1.45 (m, 4H), 1.56-1.45 (m, 4H), 1.43 (s, 9H), 1.41-1.29 (m, 4H). $^{13}$C NMR (100 MHz, CDCl₃): δ 172.7, 156.1, 79.1, 51.3, 40.2, 39.3, 36.5, 29.8, 29.2, 28.6, 28.4, 26.4, 25.2, 23.9.

N-(5-aminopentyl)-2-azidoacetamide (13a) (C2-N₃ Linker)

To an ice cold solution of 12a (19.2 mg, 0.067 mmol) in dichloromethane (0.9 ml) was added trifluoroacetic acid (153 mg, 1.346 mmol). After stirring for 10 min, the reaction mixture was allowed to reach room temperature and stirred for 2 h. Toluene (4 ml) was then added and the volatiles were removed under reduced pressure. The crude was azeotroped again with toluene to remove traces of TFA and was then dried under HVP for 3 hours to yield a light yellow oil (quantitative yield) which was sufficiently pure for further use, as revealed by NMR. $^1$H NMR (400 MHz, CD₃OD): δ 3.87 (s, 2H), 3.24 (t, J=7.1 Hz, 2H), 2.92 (t, J=7.5 Hz, 2H), 1.72-1.63 (m, 2H), 1.62-1.53 (m, 2H), 1.46-1.36 (m, 2H). $^{13}$C NMR (100 MHz, CD₃OD): δ 170.3, 53.1, 40.7, 40.1, 30.0, 28.3, 24.7.

N-(5-aminopentyl)-6-azidohexanamide (13b) (C6-N₃ Linker)

Compound 13b was synthesized by following a similar procedure as described above for 13a (starting with 22.8 mg, 0.067 mmol of 12b). $^1$H NMR (400 MHz, CD₃OD): δ 3.29 (t, J=6.8 Hz, 2H), 3.19 (t, J=7 Hz, 2H), 2.92 (t, J=7.7 Hz, 2H), 2.20 (t, J=7.3 Hz, 2H), 1.73-1.51 (m, 8H), 1.46-1.35 (m, 4H). $^{13}$C NMR (100 MHz, CD₃OD): δ 176.2, 52.5, 40.7, 40.0, 37.0, 30.1, 29.8, 28.3, 27.5, 26.7, 24.8.

MMAF-6C Thiol Linker Synthesis

Figure 16C:
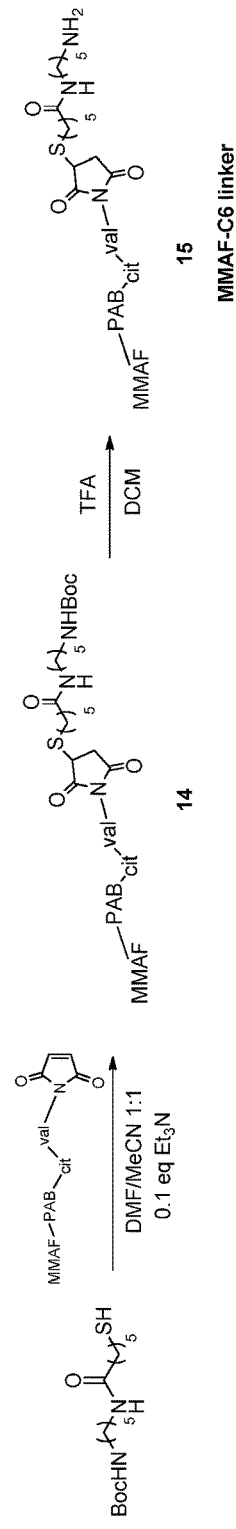

Compounds 14-15 and reaction schemes are shown in FIG. 16C.

Maleimide-Valine-Citrullin-PAB-MMAF+6C Thiol Linker (Boc Protected) (14)

To a solution of maleimide-valine-citrullin-PAB-MMAF (8.8 mg, 6.61 μmol) in DMF (0.6 ml) was added 6.6 μl of a 0.1 M solution of triethylamine in DMF (0.66 μmol Et₃N), followed by the dropwise addition of a solution of tert-butyl (5-(6-mercaptohexanamido)pentyl)carbamate (3 mg, 9.02 μmol) in acetonitrile (0.3 ml). The reaction was stirred for 3 h, diluted with water (2 ml) and purified with semi-preparative RP HPLC with the following system: water/50 mM NH₄HCO₃ (solvent A), acetonitrile (solvent B); 0-5 min: 40% B, 5-20 min: 40-80% B; UV=254 nm; t$_R$=10.3 min; Xbridge column. The product was obtained as a white solid after lyophilization (8.7 mg, 79% yield).

Maleimide-Valine-Citrullin-PAB-MMAF+6C Thiol Linker (MMAF-6C Linker) (15)

Compound 14 (8 mg, 4.81 μm) was dissolved in an ice cold solution of dichloromethane/TFA 95:5 (8 ml). The reaction mixture was allowed to reach room temperature and stirred for 40 min after which time the volatiles were removed under reduced pressure with the addition of toluene. Traces of solvents were removed under high vacuum and the residue was purified by semi-preparative HPLC with the following system: water/50 mM NH$_4$HCO$_3$ (solvent A), acetonitrile (solvent B); 0-5 min: 30% B, 5-20 min: 30-70% B; UV=254 nm; t$_R$=11.7 min; Xbridge column. The product was obtained as a white solid after lyophilization (4.86 mg, 65% yield). ESI-QTOF MS m/z calculated for C$_{79}$H$_{127}$N$_{13}$O$_{17}$S [M+H]$^+$ 781.9670, measured 781.9667.

Example 4: BTG-Mediated Coupling of Substrates to Antibodies

Materials and Methods

Reactions were monitored and the products were analyzed by LC-MS following the protocols reported below.

Deglycosylation of Antibody

Antibody (chimeric antibody generated by immunization of mice and converted to human IgG1 isotype In PBS buffer (PBS (10×): Weigh 2.1 g KH$_2$PO$_4$, 90 g NaCl, 4.8 g Na$_2$HPO$_4$×2H$_2$O was transferred to a 1 L glass bottle. Water was added to a volume of 1 L. To get PBS 1×, 100 mL PBS (10×) was used and water added to a volume of 900 mL. The solution was adjusted pH to 7.2 and filled to 1 L with water, incubated with 6 Units/mg protein of N-glycosidase F (PNGase F) from *Flavobacterium meningosepticum* (Roche, Switzerland) overnight at 37° C. The enzyme was then removed by centrifugation-dialysis (Vivaspin MWCO 50 kDa, Vivascience, Winkel, Switzerland).

Enzymatic Modification of Antibody 1 mg/mL deglycosylated antibody in PBS was incubated with 80 equivalents of ligand and 1 U/mL or >1 U/mL bacterial transglutaminase (TGase, Zedira, Darmstadt, Germany) overnight at 37° C. Excess of ligand and the TGase were removed by centrifugation-dialysis (Vivaspin MWCO 50 kDa, Vivascience, Winkel, Switzerland).

Deprotection of Protected Thiol Linker

The method for deacetylation of the protected thiol linker is adapted from published procedures (Thermo Scientific). 0.5M hydroxylamine, 25 mM EDTA is prepared in phosphate buffered saline (PBS), pH 7.2-8.5. 1 mL of antibody-linker conjugate is combined with 100 μL of prepared 0.5M hydroxylamine. The mixture is incubated for 2 h at room temperature. The reaction mixture is then be purified into PBS containing 10 mM EDTA by using a desalting column (HiTrap Desalting column, 5 mL, GE Healthcare).

Coupling Deprotected Antibody-Linker Conjugate with Maleimide Functionalize Toxin Coupling of deprotected antibody-linker conjugate with maleimide functionalize toxin is carried out as in J. R. Junutula et al., (2008) *Nat Biotechnol* 26, 925. 3 equivalents per SH group of the maleimide functionalized ligand is be combined with the deprotected antibody-linker conjugate. The reaction is incubated at RT for 1.5 h before desalting into PBS.

LC-MS Analysis

LC-MS analysis was performed on a Waters LCT Premier mass spectrometer. Samples were chromatographed on an Aeris WIDEPORE XB-C18 column (3.6 μm, 100 mm×2.1 mm; Phenomenex) heated to 65° C. using a linear gradient from 22 to 55% A in 15 min plus 5% solvent C (solvent A: acetonitrile+0.1% formic acid, solvent B: water+0.1% formic acid, solvent C: 2-propanol) at a flow rate of 0.5 mL/min. The eluent was ionized using an electrospray source. Data were collected with MassLynx 4.1 and deconvolution was performed using MaxEnt1. Before the LC-MS analysis, 10 μg of antibody were mixed with DTT (final concentration should be 20 mM). Guan-buffer (7.5M Guan-HCl, 0.1M Tris-HCl, 1 mM EDTA buffer pH 8.5 (adjusted by addition of concentrated NH$_4$OH (28% aqueous solution) was added to a final volume of 50 μL. Finally, 5 μL of the mixture were injected.

Results

Light Chain

Using the above described enzymatic method to modify antibodies, the light chain remains unaffected (23341 Da found).

Deglycosylation of Antibody

Complete deglycosylation of antibody was accomplished and a mass of 48945 Da for unmodified, deglycosylated heavy chain was determined.

Conjugation of BC and DC with TGase

The reaction did not go to completion when using 1 U/mL TGase. However, reaction conditions were explored and using 6 U/mL TGase permitted the modification of all heavy chains with either exactly one biotin-cadaverine (MW: 328 g/mol; 328-17=311 Da; 48945+311=49256 Da, 49257 Da found) or one dansyl-cadaverine (MW: 335 g/mol; 335-17=318 Da; 48945+318=49263 Da, 49264 Da found) per heavychain.

Conjugation of DOTA Thiol Linker (Short) with BTGase

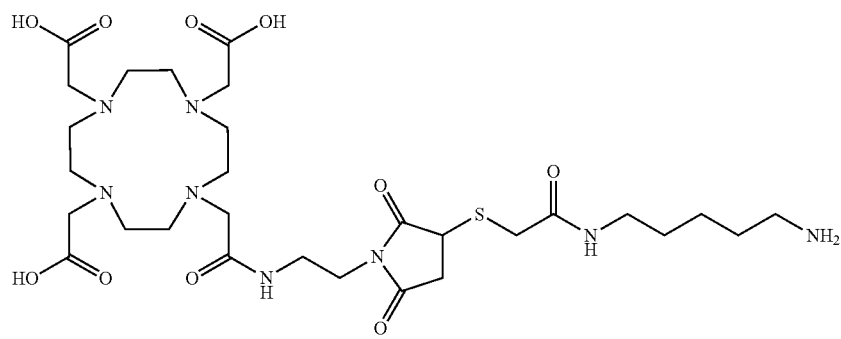

MW: 702.82, 5

The chemical structure of short thiol linker 2 coupled to maleimide-DOTA (1,4,7,10-tetraazacyclododecane-1,4,7,10-tetraacetic acid) is shown above. The molecular weight is indicated below the structure.

Figure 17A:
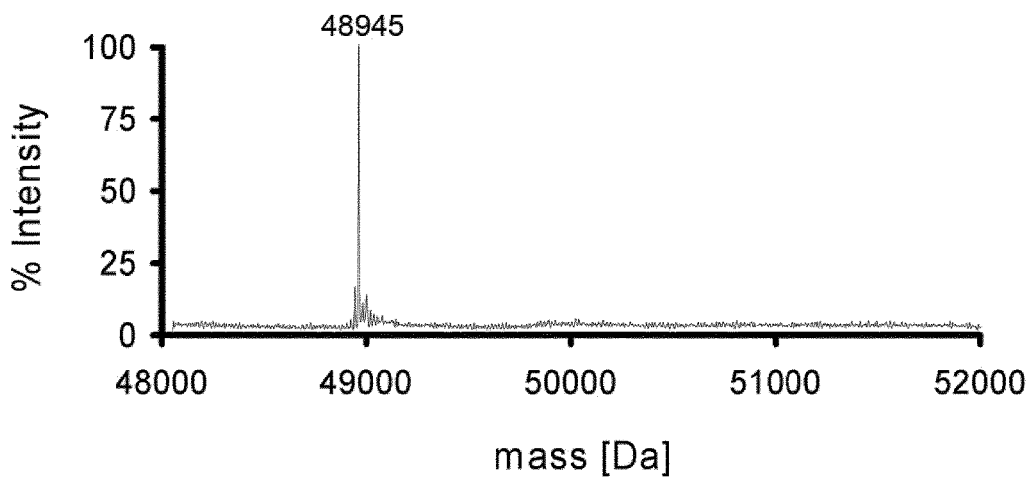
FIGS. 17A and 17B show the deconvoluted mass spectra of chimeric human IgG1 heavy chain coupled to DOTA thiol linker 5 using either 1 U/mL (left) or 6 U/mL BTGase.
Figure 17B:
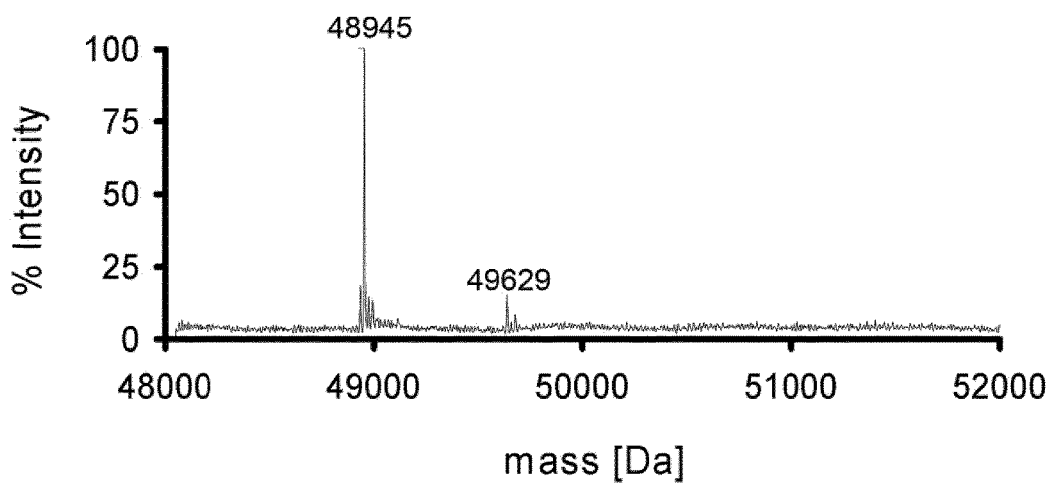

Quantitative enzymatic modification of antibody heavy chain with short DOTA thiol linker shown above by BTGase could not be accomplished (see FIG. 17A: 1 U/mL BTGase, only unmodified heavy chain, 48945 Da found. FIG. 17B: 6 U/mL BTGase, minor peak modified heavy chain with one DOTA thiol linker per heavy chain, MW 702 g/mol, 702-17=685 Da, 48945+685=49630 Da, 49629 Da found). Reaction conditions were explored but neither by using 1 U/mL (expected) nor by using 6 U/mL BTGase could coupling be achieved. Prolonged incubation time could not influence the modification efficiency.

Conjugation of Protected Thiol Linkers (Short and Long Spacer)

Protected long and short thio-linkers of FIG. 15 (compounds 6a and 6b) were coupled using TGase quantitatively and stoichiometrically to antibodies. Using 6 U/mL TGase in reaction conditions it was possible to couple the two different tested thiol linkers quantitatively and stoichiometrically uniform to the heavy chain. The preparation for analysis is shown in scheme 1 below. It is likely that two peaks are appearing in the MS spectra as the basic pH during the sample preparation for the MS measurement (see "LC-MS analysis") can promote deacetylation of the protected thiol group. Partial deprotection occurred for the short thiol linker (n=1) whereas complete deprotection was observed for the long thiol linker (n=5).

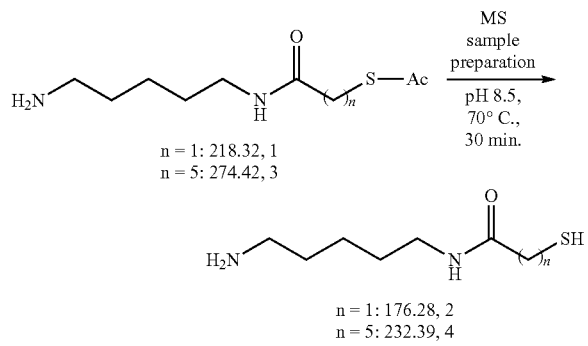

Scheme 1 (above): Deacetylation of protected thiol linkers 1 and 3 during sample preparation for mass spectrometry. Molecular weights for both short (n=1) and long (n=5) protected thiol linker as well as for the corresponding deprotected linkers 2 and 4 are indicated below the structures.

Figure 18A:
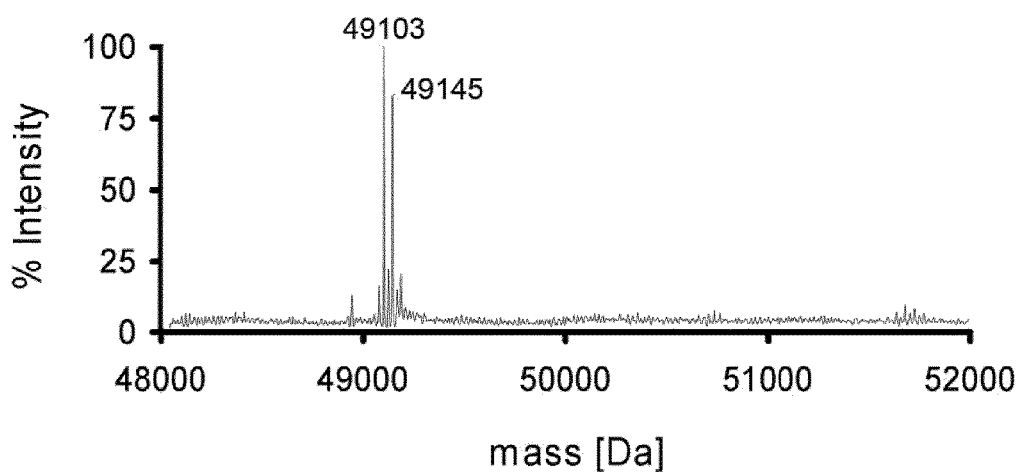
FIGS. 18A and 18B show the deconvoluted mass spectra of c chimeric human IgG1 heavy chain coupled to the short (left) and long (right) thiol linker, compounds 4a and 4b. The FIG. 18A spectrum shows the protected short linker compound 4a and the FIG. 18B spectrum shows deprotected long linker 4b.
Figure 18B:
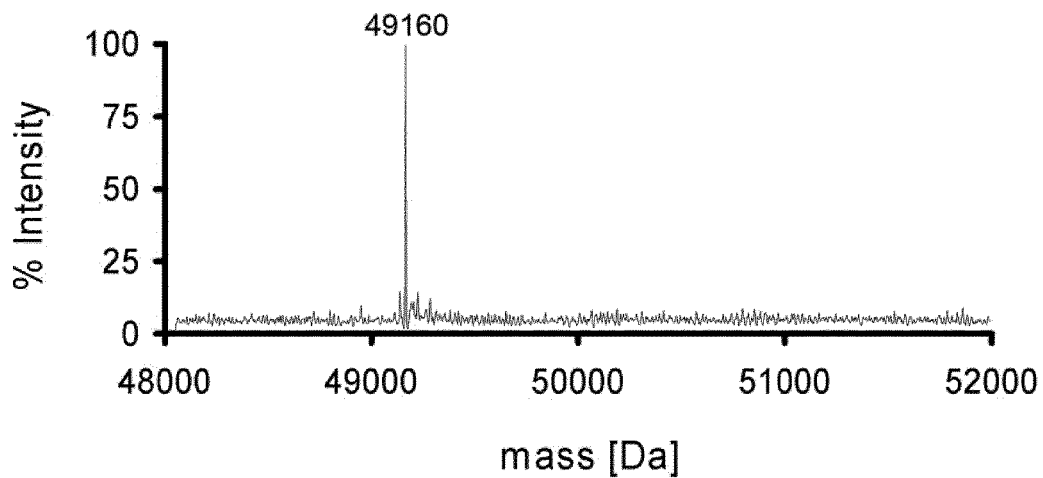

The results are shown in FIGS. 18A and 18B, showing the deconvoluted mass spectra of heavy chain coupled to the short (1A) and long (2B) thiol linker. FIG. 18A spectrum: Protected short linker 1: 218 g/mol, 218-17=201 Da, 48945+201=49146 Da, 49145 Da found; deprotected short linker 2: 176 g/mol, 176-17=159 Da, 48945+159=49104, 49103 found. FIG. 18B spectrum: Deprotected long linker 4: 232 g/mol, 232-17=215 Da, 48945+215=49160 Da, 49160 Da found.

All headings and sub-headings are used herein for convenience only and should not be construed as limiting the invention in any way. Any combination of the above-described elements in all possible variations thereof is encompassed by the invention unless otherwise indicated herein or otherwise clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e. g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents, The description herein of any aspect or embodiment of the invention using terms such as reference to an element or elements is intended to provide support for a similar aspect or embodiment of the invention that "consists of," "consists essentially of" or "substantially comprises" that particular element or elements, unless otherwise stated or clearly contradicted by context (e. g., a composition described herein as comprising a particular element should be understood as also describing a composition consisting of that element, unless otherwise stated or clearly contradicted by context).

All publications and patent applications cited in this specification are herein incorporated by reference in their entireties as if each individual publication or patent application were specifically and individually indicated to be incorporated by reference.

The invention claimed is:

1. A method for evaluating antibodies, comprising:
   a) providing a first and second antibody sample each comprising a plurality of antibodies comprising at least one acceptor glutamine residue (Q) in a constant region, wherein the first and second antibody-containing samples differ from one another with respect to antibody variable region sequence, and wherein substantially all of the antibodies present in the first sample are of the same sequence and substantially all of the antibodies present in the second sample are of the same sequence;
   b) (i) reacting each of said first and second antibody sample with a lysine-based linker comprising a reactive group (R), in the presence of a transglutaminase (TGase), under conditions sufficient such that antibodies in said first and second antibody samples are conjugated to a lysine-based linker comprising the reactive group (R); and (ii) further reacting the resulting antibodies of process (i) with a compound comprising: (a) a reactive group (R') that reacts with reactive group (R) on the lysine-based linker, and (b) a moiety-of-interest (Z), whereby a first and a second antibody sample each conjugated to a lysine-based linker comprising the moiety-of-interest (Z) is obtained; and c) evaluating antibodies of the first and second antibody sample each conjugated to the lysine-based linker comprising a moiety-of-interest (Z) obtained in process (b) for a characteristic of interest, wherein:

(i) the first and second antibody samples are specific for the same antigen, (ii) at least 90% of the antibodies in each of the first and second antibody samples obtained in process (b) have the same number of functionalized acceptor glutamine residues (Q) per antibody, wherein each of the functionalized acceptor glutamines are conjugated to a lysine-based linker comprising a moiety of interest, and (iii) the moiety-of-interest (Z) is selected from the group consisting of a hydrophobic organic compound, an organic compound having an electrically negative charge, an organic compound having a molecular weight of at least 400 g/mol, and any combination thereof.

2. The method of claim 1, wherein the first and second antibody samples in process b) are reacted in separate containers.

3. The method of claim 1, wherein process b) comprises: reacting each of said first and second antibody sample with a lysine-based linker of Formula Ia

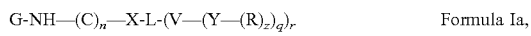
$$G\text{-}NH\text{-}(C)_n\text{-}X\text{-}L\text{-}(V\text{-}(Y\text{-}(R)_z)_q)_r$$ Formula Ia, in the presence of a TGase, under conditions sufficient such that antibodies of Formula II comprising a reactive moiety (R) are obtained

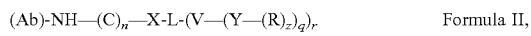
$$(Ab)\text{-}NH\text{-}(C)_n\text{-}X\text{-}L\text{-}(V\text{-}(Y\text{-}(R)_z)_q)_r$$ Formula II, and further reacting the antibodies of Formula II to obtain antibodies of Formula IV

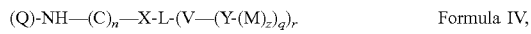
$$(Q)\text{-}NH\text{-}(C)_n\text{-}X\text{-}L\text{-}(V\text{-}(Y\text{-}(M)_z)_q)_r$$ Formula IV, where: G is an H, amine protecting group, or upon conjugation, an immunoglobulin (Ab) or other protein attached via an amide bond;

$(C)_n$ is a substituted or unsubstituted alkyl or heteroalkyl chain, optionally wherein any carbon of the chain is substituted with an alkoxy, hydroxyl, alkylcarbonyloxy, alkyl-S—, thiol, alkyl-C(O)S—, amine, alkylamine, amide, or alkylamide; n, the length of the carbon chain, is an integer selected from among the range of 2 to 20;

X is NH, O, S, or absent;

L and L' are independently absent, a bond or a continuation of a bond, or a carbon comprising framework of 5 to 200 atoms substituted at one or more atoms;

r and r' are independently an integer selected from among 1, 2, 3 or 4;

q and q' are independently an integer selected from among 1, 2, 3 or 4; and z and z' are independently an integer selected from among 1, 2, 3 or 4;

V and V' are independently absent, being a bond or a continuation of a bond if L or L' is a bond, a non-cleavable moiety or a conditionally-cleavable moiety, optionally following prior conditional transformation, which can be cleaved or transformed by a chemical, photochemical, physical, biological, or enzymatic process;

Y and Y' are independently absent, being a bond or a continuation of a bond if V or V' is a bond or continuation of a bond, or a spacer system which is comprised of 1 or more spacers;

R is a reactive moiety;

M is: (RR')-L'-(V'—(Y'—(Z)$_{z'}$)$_{q'}$)$_{r'}$;

(RR') is an addition product between R and a complementary reactive group R'; and Z is a moiety-of-interest, optionally a moiety that improves the pharmacokinetic properties, or a therapeutic moiety or a diagnostic moiety.

4. The method of claim 3, wherein the antibodies of Formula II are reacted with a compound of Formula III

$$R'\text{-}L'\text{-}(V'\text{-}(Y'\text{-}(Z)_{z'})_{q'})_{r'}$$ Formula III to obtain the antibodies of Formula IV comprising a moiety-of-interest (Z).

5. The method of claim 1, wherein said first and second antibody sample differ with respect to isotype.

6. The method of claim 3, wherein the first and second antibody samples obtained in process (b) each comprise a plurality of antibodies of Formula II or IV, wherein at least 90% of the antibodies in each of the samples have the same q, r and z values.

7. The method of claim 3, wherein the first and second antibody samples obtained in process (b) each further share the same —NH—(C)$_n$—X, L, V, V', Y, Y', R, RR' and/or Z moieties.

8. The method of claim 1, wherein said constant region is a human heavy chain constant region.

9. The method of claim 1, wherein the first and second antibody-containing samples differ from one another with respect to antibody quantity.

10. The method of claim 1, wherein said process (c) of evaluating antibodies for a characteristic of interest comprises evaluating antibodies for one or more properties selected from the group consisting of: binding to an antigen of interest, binding to an Fc receptor, Fc-domain mediated effector function(s), agonistic or antagonistic activity at a polypeptide to which the antibody binds, ability to cause the death of a cell expressing an antigen of interest, in vitro stability, in vivo stability, and susceptibility to aggregate in solution.

11. The method of claim 1, wherein the characteristic of interest is suitability for use as an antibody-drug conjugate.

12. The method of claim 11, wherein said process (c) of evaluating antibodies for suitability of the antibodies for use as an antibody-drug conjugate comprises evaluating the antibodies for their ability to cause the death of a cell expressing an antigen of interest.

13. The method of claim 1, wherein said lysine-based linker is a linker comprising a NH—(C)$_n$— moiety, where $(C)_n$ is a substituted or unsubstituted carbon chain, wherein any carbon of the chain is optionally substituted with a O, N or S atom of an ether, ester, thioether, thioester, amine, alkylamine, amide, or alkylamide.

14. The method of claim 3, wherein V' is a conditionally-cleavable moiety following prior conditional transformation, which can be cleaved or transformed by a chemical, photochemical, physical, biological, or enzymatic process.

15. The method of claim 3, wherein Y' is a self-eliminating spacer system.

16. The method of claim 3, wherein Y' is a non-self-elimination spacer system.

17. The method of claim 3, wherein Z is selected from the group consisting of taxanes, anthracyclines, camptothecins, epothilones, mytomycins, combretastatins, vinca alkaloids, nitrogen mustards, maytansinoids, calicheamycins, duocarmycins, tubulysins, dolastatins and auristatins, enediynes, pyrrolobenzodiazepines, and ethylenimines.

18. The method of claim 3, wherein Z is a hydrophobic organic compound.

19. The method of claim 1, wherein said constant region is a murine heavy chain constant region.

20. The method of claim 6, wherein the at least one of the functionalized acceptor glutamine residues is in an antibody heavy chain at position 295 according to EU numbering convention.

21. The method of claim 6, wherein at least one of the functionalized acceptor glutamine residues is a glutamine residue substituted into an antibody heavy chain at position 297 according to EU numbering convention.

22. The method of claim 6, wherein at least 90% of the antibodies in each of the sample have (m) functionalized acceptor glutamine residues (Q) per antibody, wherein m is an integer selected from 2 or 4.

\* \* \* \* \*